US008304409B2

(12) United States Patent
Earl et al.

(10) Patent No.: US 8,304,409 B2
(45) Date of Patent: *Nov. 6, 2012

(54) NITROSATED NONSTEROIDAL ANTIINFLAMMATORY COMPOUNDS, COMPOSITIONS AND METHODS OF USE

(75) Inventors: Richard A. Earl, Westford, MA (US); Maiko Ezawa, Acton, MA (US); Xinqin Fang, Lexington, MA (US); David S. Garvey, Dover, MA (US); Ricky D. Gaston, Malden, MA (US); Subhash P. Khanapure, Clinton, MA (US); L. Gordon Letts, Dover, MA (US); Chia-En Lin, Concord, MA (US); Ramani R. Ranatunge, Lexington, MA (US); Stewart K. Richardson, Tolland, CT (US); Joseph D. Schroeder, Minneapolis, MN (US); Cheri A. Stevenson, Haverhill, MA (US); Shiow-Jyi Wey, Billerica, MA (US)

(73) Assignee: Nicox S.A. (FR)

(*) Notice: Subject to any disclaimer, the term of this patent is extended or adjusted under 35 U.S.C. 154(b) by 174 days.

This patent is subject to a terminal disclaimer.

(21) Appl. No.: 12/636,329

(22) Filed: Dec. 11, 2009

(65) Prior Publication Data

US 2010/0093671 A1    Apr. 15, 2010

Related U.S. Application Data

(62) Division of application No. 11/134,358, filed on May 23, 2005, now Pat. No. 7,754,772, which is a division of application No. 10/612,014, filed on Jul. 3, 2003, now Pat. No. 7,163,958.

(60) Provisional application No. 60/393,111, filed on Jul. 3, 2002, provisional application No. 60/397,979, filed on Jul. 24, 2002, provisional application No. 60/418,353, filed on Oct. 16, 2002, provisional application No. 60/449,798, filed on Feb. 26, 2003, provisional application No. 60/456,182, filed on Mar. 21, 2003.

(51) Int. Cl.
```
A61K 31/54     (2006.01)
A61K 31/44     (2006.01)
A61K 31/445    (2006.01)
A61K 31/425    (2006.01)
A61K 31/42     (2006.01)
A61K 31/415    (2006.01)
A61K 31/335    (2006.01)
A61K 31/24     (2006.01)
A61K 31/12     (2006.01)
```
(52) U.S. Cl. ............ 514/226.2; 514/291; 514/327; 514/365; 514/374; 514/375; 514/378; 514/393; 514/450; 514/539; 514/676

(58) Field of Classification Search ............... 514/327, 514/226.2, 291, 365, 374, 375, 378, 393, 514/450, 539, 676
See application file for complete search history.

(56) References Cited

U.S. PATENT DOCUMENTS

| | | |
|---|---|---|
| 5,360,925 A | 11/1994 | Chabrier de Lassauniere et al. |
| 5,483,426 A | 1/1996 | Lewis et al. |
| 5,607,966 A | 3/1997 | Hellberg et al. |
| 5,621,000 A | 4/1997 | Arena et al. |
| 5,700,947 A | 12/1997 | Soldato et al. |
| 5,703,073 A | 12/1997 | Garvey et al. |
| 5,780,495 A | 7/1998 | Del Soldato et al. |
| 5,811,438 A | 9/1998 | Hellberg et al. |
| 5,844,696 A | 12/1998 | Masia et al. |
| 5,859,053 A | 1/1999 | Lesur et al. |
| 5,861,426 A | 1/1999 | Del Soldato et al. |
| 6,040,341 A | 3/2000 | Del Soldato et al. |
| 6,043,233 A | 3/2000 | Garvey et al. |
| 6,048,858 A | 4/2000 | Garvey et al. |
| 6,051,588 A | 4/2000 | Garvey et al. |

(Continued)

FOREIGN PATENT DOCUMENTS

CN    1305997    8/2001

(Continued)

OTHER PUBLICATIONS

Abadi et al. Arch. Pharm. Med. Chem., 104-106 (2001).

(Continued)

*Primary Examiner* — James O Wilson
*Assistant Examiner* — Ebenezer O Sackey
(74) *Attorney, Agent, or Firm* — Wilmer Cutler Pickering Hale & Dorr LLP.

(57) ABSTRACT

The invention describes novel nitrosated nonsteroidal antiinflammatory drugs (NSAIDs) and pharmaceutically acceptable salts thereof, and novel compositions comprising at least one nitrosated NSAID, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The invention also provides novel compositions comprising at least one nitrosated NSAID, and at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The invention also provides novel kits comprising at least one nitrosated NSAID, and, optionally, at least one nitric oxide donor and/or at least one therapeutic agent. The invention also provides methods for treating inflammation, pain and fever; for treating gastrointestinal disorders; for facilitating wound healing; for treating and/or preventing gastrointestinal, renal and/or respiratory toxicities resulting from the use of nonsteroidal antiinflammatory compounds; for treating inflammatory disease states and/or disorders; and for treating and/or preventing ophthalmic diseases and/or disorders.

6 Claims, No Drawings

U.S. PATENT DOCUMENTS

| | | | |
|---|---|---|---|
| 6,057,347 | A | 5/2000 | Garvey et al. |
| 6,083,515 | A | 7/2000 | Garvey et al. |
| 6,113,301 | A | 9/2000 | Burton |
| 6,143,734 | A | 11/2000 | Garvey et al. |
| 6,244,735 | B1 | 6/2001 | Burton |
| 6,297,260 | B1 | 10/2001 | Bandarage et al. |
| 6,323,234 | B1 | 11/2001 | Garvey et al. |
| 6,355,666 | B1 | 3/2002 | Lai et al. |
| 6,396,260 | B1 | 5/2002 | Reichl et al. |
| 6,429,223 | B1 | 8/2002 | Lai et al. |
| 6,436,990 | B1 | 8/2002 | Ekwuribe et al. |
| 6,482,846 | B1 | 11/2002 | Garvey et al. |
| 6,512,137 | B1 | 1/2003 | Del Soldato et al. |
| 6,525,098 | B1 | 2/2003 | Ekwuribe et al. |
| 6,538,033 | B2 | 3/2003 | Bing |
| 6,552,078 | B2 | 4/2003 | Ekwuribe et al. |
| 6,593,347 | B2 | 7/2003 | Bandarage et al. |
| 6,653,548 | B2 | 11/2003 | Yamashita |
| 6,677,374 | B2 | 1/2004 | Thatcher et al. |
| 2002/0028845 | A1 | 3/2002 | Ekwuribe et al. |
| 2002/0088111 | A1 | 7/2002 | Von Arx et al. |
| 2002/0111370 | A1 | 8/2002 | Bergman et al. |
| 2005/0137191 | A1 | 6/2005 | Thatcher et al. |
| 2011/0098253 | A1* | 4/2011 | Earl et al. ............. 514/120 |

FOREIGN PATENT DOCUMENTS

| | | |
|---|---|---|
| EP | 0 440 098 | 8/1991 |
| EP | 0 676 204 | 10/1995 |
| EP | 0738706 | 10/1996 |
| EP | 0 656 881 | 10/1998 |
| EP | 0 904 110 | 3/1999 |
| WO | WO-94/03421 | 2/1994 |
| WO | WO-94/04484 | 3/1994 |
| WO | WO-95/09831 | 4/1995 |
| WO | WO-95/30641 | 11/1995 |
| WO | WO-96/32946 | 10/1996 |
| WO | WO-97/16405 | 5/1997 |
| WO | WO-97/31654 | 9/1997 |
| WO | WO-98/09948 | 3/1998 |
| WO | WO-98/25981 | 6/1998 |
| WO | WO-99/44595 | 9/1999 |
| WO | WO-99/45004 | 9/1999 |
| WO | WO-00/00200 | 1/2000 |
| WO | WO-00/06585 | 2/2000 |
| WO | WO-00/25776 | 5/2000 |
| WO | WO-00/44705 | 8/2000 |
| WO | WO-00/51988 | 10/2000 |
| WO | WO-00/61537 | 10/2000 |
| WO | WO-00/61541 | 10/2000 |
| WO | WO-00/61604 | 10/2000 |
| WO | WO-0061549 | 10/2000 |
| WO | WO-00/72838 | 12/2000 |
| WO | WO-01/00563 | 1/2001 |
| WO | WO-01/04082 | 1/2001 |
| WO | WO-01/10814 | 2/2001 |
| WO | WO-01/12584 | 2/2001 |
| WO | WO-01/49275 | 7/2001 |
| WO | WO-01/66088 | 9/2001 |
| WO | WO-01/78781 | 10/2001 |
| WO | WO-01/93680 | 12/2001 |
| WO | WO-02/00166 | 1/2002 |
| WO | WO-02/00167 | 1/2002 |
| WO | WO-02/11706 | 2/2002 |
| WO | WO-02/11707 | 2/2002 |
| WO | WO-02/30866 | 4/2002 |
| WO | WO-02/051385 | 7/2002 |
| WO | WO-02/053188 | 7/2002 |
| WO | WO-02/074282 | 9/2002 |
| WO | WO-02/092072 | 11/2002 |
| WO | WO-02/100400 | 12/2002 |
| WO | WO-03/000642 | 1/2003 |
| WO | WO-03/000643 | 1/2003 |
| WO | WO-03/013499 | 2/2003 |
| WO | WO-03/022249 | 3/2003 |
| WO | WO-03/084550 | 10/2003 |
| WO | WO-2004/000215 | 12/2003 |
| WO | WO-2004/000273 | 12/2003 |
| WO | WO-2004/000300 | 12/2003 |
| WO | WO-2004/020384 | 3/2004 |
| WO | WO-2004/020385 | 3/2004 |
| WO | WO-2004/026808 | 4/2004 |

OTHER PUBLICATIONS

Al-Swayeh et al. Br. J. Pharmacol., 129:343-350 (2000).
Aug. 10, 2004. International Search Report from PCT/US03/21026.
Barrachina et al. Eur. J. Pharmacol., 281:R3-R4 (1995).
Bing et al. Biochem. Biophys. Res. Comm., 275:350-353 (2000).
Boughton-Smith et al. Eur. J. Pharmacol., 191:485-488 (1990).
Brown et al. Eur. J. Pharmacol., 103-104 (1992).
Carty et al. Agents Actions, 39:157-165 (1993).
Cena et al. J. Med. Chem., 46:747-754 (2003).
Conforti et al. Agents Action, 40(3):176-180 (1993).
Cuzzolin et al. Pharmacol. Res. 29(1):89-97 (1994).
Cuzzolin et al. Pharmacol. Res. 31:61-65 (1995).
Davies et al. Aliment Pharmacol. Ther., 11:69-79 (1997).
Del Soldato et al. Br. J. Pharmac., 67:33-37 (1979).
Del Soldato et al. Inflammopharmacology, 4:181-188 (1996).
Elliott et al. Gastroenterol., 109:524-530 (1995).
Endres et al. Eur. J. Med. Chem., 34:895-901 (1999).
European Patent Application No. 03763193.4 Supplementary European Search Report (Jan. 22, 2008).
Fiorucci, Stefano et al. Drug Safety, 24(11): 801-811 (2001).
Gilmer et al. Eur. J. Pharm. Sci., 14:221-227 (2001).
Gu et al. Tet. Letts., 27:1763-1766 (1986).
Insel, Paul A. The Pharmacological Basis of Therapeutics, pp. 638-681 (1990).
Johal et al. Br. J. Pharmacol., 130:811-818 (2000).
Kartasasmita et al. Arch. Pharm. Med. Chem. 8:363-366 (2002).
Kitigawa et al. J. Pharmacol. Exp. Ther., 253:1133-1137 (1990).
Konturek et al. Eur. J. Pharmacol., 239:215-217 (1993).
Langford et al. Arterioscler. Thromb. Vasc. Biol., 16:51-57 (1996).
MacNaughton et al. Life Sciences, 45:1869-1876 (1989).
Muscara et al. Br. J. Pharmacol., 129:681-686 (2000).
Muscara et al. Life Sciences, 62:235-240 (1998).
Palmer et al. Nature, 333:664-666 (1998).
Rachmilewitz et al. Gut., 35:1394-1397 (1994).
Rautio et al. J. Pharm. Sci., 87:1622-1628 (1998).
Rautio et al. Pharmacol. Res., 16:1172-1178 (1999).
Reuter et al. Gastroenterol., 106(4), A759 (1994).
Reuter et al. Life Sciences, 55(1):1-8 (1994).
Wallace et al. Eur. J. Pharmacol., 257:249-255 (1994).
Wallace et al. Eur. J. Pharmacol., 63-68 (1995).
Wallace et al. Expert Opinion Investigational Drugs, 4(7):613-619 (1995).
Wallace et al. Gastroenterol., 106(4), Part 2, A208. Abstract (1994).
Wallace et al. Gastroenterol., 107:173-179 (1994).
Wallace et al. J. Clin. Invest., 96:2711-2718 (1995).
Wallace et al. J. Gastroenterol. Hepatol, 9:S40-S44 (1994).
Wallace et al. Novel Molecular Approaches to Anti-inflammatory Theory, 121-129 (1994).
Wallace et al. Trends Pharmacol., Sci., 15(11): 405-406 (1994).
Williams et al. Cancer Research, 61:3285-3289 (Apr. 15, 2001).
Yamamoto et al. Life Sciences, 67:839-846 (2000).

* cited by examiner

NITROSATED NONSTEROIDAL ANTIINFLAMMATORY COMPOUNDS, COMPOSITIONS AND METHODS OF USE

RELATED APPLICATIONS

This application is a divisional of U.S. application Ser. No. 11/134,358, filed May 23, 2005, issued as U.S. Pat. No. 7,754,772, which is a divisional of U.S. application Ser. No. 10/612,014, filed Jul. 3, 2003, issued as U.S. Pat. No. 7,163,958, which claims priority under 35 USC §119 to U.S. Application No. 60/393,111 filed Jul. 3, 2002; U.S. Application No. 60/397,979 filed Jul. 24, 2002; U.S. Application No. 60/418,353 filed Oct. 16, 2002; U.S. Application No. 60/449,798 filed Feb. 26, 2003; and U.S. Application No. 60/456,182 filed Mar. 21, 2003.

FIELD OF INVENTION

The invention describes novel nitrosated nonsteroidal antiinflammatory drugs (NSAIDs) and pharmaceutically acceptable salts thereof, and novel compositions comprising at least one nitrosated NSAID, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one therapeutic agent. The invention also provides novel compositions comprising at least one nitrosated NSAID, and at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The invention also provides novel kits comprising at least one nitrosated NSAID, and, optionally, at least one nitric oxide donor and/or at least one therapeutic agent. The invention also provides methods for treating inflammation, pain and fever; for treating gastrointestinal disorders; for facilitating wound healing; for treating and/or preventing gastrointestinal, renal and/or respiratory toxicities resulting from the use of nonsteroidal antiinflammatory compounds; for treating inflammatory disease states and/or disorders; and for treating and/or preventing ophthalmic diseases and/or disorders.

BACKGROUND OF THE INVENTION

Nonsteroidal anti-inflammatory compounds (NSAIDs) are widely used for the treatment of pain, inflammation, and acute and chronic inflammatory disorders, such as, for example, osteoarthritis arthritis and rheumatoid arthritis. These compounds inhibit the activity of the enzyme cyclooxygenase (COX), also known as prostaglandin G/H synthase, which is the enzyme that converts arachidonic acid into prostanoids. The NSAIDs also inhibit the production of other prostaglandins, especially prostaglandin $G_2$, prostaglandin $H_2$ and prostaglandin $E_2$, thereby reducing the prostaglandin-induced pain and swelling associated with the inflammation process. The chronic use of NSAIDs has been associated with adverse effects, such as gastrointestinal ulceration and renal and respiratory toxicity. The undesirable side effects are also due to the inhibition of prostaglandin in the affected organ.

Recently two isoforms of cyclooxygenase, encoded by two distinct genes (Kujubu et al, *J. Biol. Chem.*, 266, 12866-12872 (1991)), have been identified—a constitutive form, cyclooxygenase-1 (COX-1), and an inductive form, cyclooxygenase-2 (COX-2). It is thought that the antiinflammatory effects of NSAIDs are mediated by the inhibition of COX-2, whereas the side effects seem to be caused by the inhibition of COX-1. The NSAIDs currently on the market either inhibit both isoforms of COX with little selectivity for either isoform or are COX-1 selective.

There is still a need in the art for novel NSAIDs that do not have the adverse side effects associated with prior art compounds. There is also a need for new and improved treatments of inflammatory diseases states and disorders; and ophthalmic diseases and disorders. The invention is directed to these, as well as other, important ends.

SUMMARY OF THE INVENTION

The invention provides novel NSAIDs that are substituted with at least one nitrogen dioxide group ($NO_2$) (i.e., nitrosated). The NSAIDs can be nitrosated through one or more sites such as oxygen (hydroxyl condensation), sulfur (sulfhydryl condensation) and/or nitrogen. These compounds are potent analgesics, have antiinflammatory properties and have an unexpected potential for facilitating wound healing. The novel compounds also have good bioavailability, possess potent analgesic and antiinflammatory properties and have unexpected properties for reducing the formation of gastrointestinal lesions (ulcers). The novel compounds also have unexpected properties in the treatment and/or prevention of ophthalmic diseases and disorders. The invention also provides compositions comprising the novel compounds described herein in a pharmaceutically acceptable carrier.

The invention is also based on the discovery that administering at least one NSAID that is substituted with at least one $NO_2$ group (i.e., nitrosated), and, optionally, at least one nitric oxide donor prevents, reduces, or reverses gastrointestinal, renal and respiratory toxicity induced by the NSAID. Nitric oxide donors include, for example, S-nitrosothiols, nitrites, nitrates, N-oxo-N-nitrosamines, SPM 3672, SPM 5185, SPM 5186 and analogues thereof, and substrates of the various isozymes of nitric oxide synthase. Thus, another embodiment of the invention provides compositions comprising at least one nitrosated NSAID and at least one compound that donates, transfers or releases nitric oxide as a charged species, i.e., nitrosonium ($NO^+$) or nitroxyl ($NO-$), or as the neutral species, nitric oxide ($NO\bullet$), and/or stimulates endogenous production of nitric oxide or EDRF in vivo and/or is a substrate for nitric oxide synthase. The invention also provides for such compositions in a pharmaceutically acceptable carrier.

Yet another embodiment of the invention provides compositions comprising at least one NSAID, that is substituted with at least one $NO_2$ group (i.e., nitrosated), and, optionally, at least one compound that donates, transfers or releases nitric oxide as a charged species, i.e., nitrosonium ($NO^+$) or nitroxyl ($NO-$), or as the neutral species, nitric oxide ($NO\bullet$), and/or stimulates endogenous production of nitric oxide or EDRF in vivo and/or is a substrate for nitric oxide synthase, and/or, optionally, at least one therapeutic agent, including but not limited to, steroids, cyclooxygenase-2 (COX-2) inhibitors, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. The invention also provides for such compositions in a pharmaceutically acceptable carrier.

Yet another embodiment of the invention provides methods for treating and/or preventing inflammation, pain and fever; for decreasing and/or preventing gastrointestinal, renal and/or respiratory toxicity resulting from the use of drugs such as, nonsteroidal antiinflammatory compounds and/or cyclooxygenase-2 selective inhibitors; for treating and/or preventing gastrointestinal disorders; and for facilitating wound healing in a patient in need thereof which comprises administering to the patient a therapeutically effective amount of at least one NSAID that is substituted with at least one $NO_2$ group (i.e., nitrosated), and, optionally, at least one compound that donates, transfers or releases nitric oxide as a charged species, i.e., nitrosonium ($NO^+$) or nitroxyl ($NO-$), or as the neutral species, nitric oxide (NO•), and/or stimulates endogenous production of nitric oxide or EDRF in vivo and/or is a substrate for nitric oxide synthase (i.e., NO donors). The methods can optionally further comprise the administration of at least one therapeutic agent, such as, for example, steroids, cyclooxygenase-2 (COX-2) inhibitors, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures of two or more thereof. In this embodiment of the invention, the methods can involve administering the nitrosated NSAIDs, administering the nitrosated NSAIDs and NO donors, administering the nitrosated NSAIDs and therapeutic agents, or administering the nitrosated NSAIDs, NO donors, and therapeutic agents. The nitrosated NSAIDs, nitric oxide donors, and/or therapeutic agents can be administered separately or as components of the same composition in one or more pharmaceutically acceptable carriers.

Yet another embodiment of the invention provides methods for treating and/or preventing inflammatory disease states and disorders in a patient in need thereof which comprises administering to the patient a therapeutically effective amount of at least one NSAID that is substituted with at least $NO_2$ group (i.e., nitrosated), and, optionally, at least one compound that donates, transfers or releases nitric oxide as a charged species, i.e., nitrosonium ($NO^+$) or nitroxyl ($NO-$), or as the neutral species, nitric oxide (NO•), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e., NO donors). The methods can optionally further comprise the administration of at least one therapeutic agent, such as, for example, steroids, cyclooxygenase-2 (COX-2) inhibitors, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures of two or more thereof. In this embodiment of the invention, the methods can involve administering the nitrosated NSAIDs, administering the nitrosated NSAIDs and NO donors, administering the nitrosated NSAIDs and therapeutic agents, or administering the nitrosated NSAIDs, NO donors, and therapeutic agents. The nitrosated NSAIDs, nitric oxide donors, and/or therapeutic agents can be administered separately or as components of the same composition in one or more pharmaceutically acceptable carriers.

Yet another embodiment of the invention provides methods for treating and/or preventing ophthalmic diseases and disorders in a patient in need thereof which comprises administering to the patient a therapeutically effective amount of at least one NSAID that is substituted with at least $NO_2$ group (i.e., nitrosylated), and, optionally, at least one compound that donates, transfers or releases nitric oxide as a charged species, i.e., nitrosonium ($NO^+$) or nitroxyl ($NO-$), or as the neutral species, nitric oxide (NO•), and/or stimulates endogenous production of nitric oxide or EDRF in vivo and/or is a substrate for nitric oxide synthase and/or stimulates endogenous production of NO or EDRF in vivo and/or is a substrate for nitric oxide synthase (i.e., NO donors). In this embodiment of the invention, the methods can involve administering the nitrosated NSAIDs or administering the nitrosated NSAIDs and NO donors. The nitrosated NSAIDs and nitric oxide donors, can be administered separately or as components of the same composition in one or more pharmaceutically acceptable carriers.

In yet another embodiment the invention provides kits comprising at least one NSAID that is substituted with at least one $NO_2$ group (i.e., nitrosated), and, optionally, at least one compound that donates, transfers or releases nitric oxide as a charged species, i.e., nitrosonium ($NO^+$) or nitroxyl ($NO-$), or as the neutral species, nitric oxide (NO•), and/or stimulates endogenous production of nitric oxide or EDRF in vivo and/or is a substrate for nitric oxide synthase. The kit can further comprise at least one therapeutic agent, such as, for example, steroids, cyclooxygenase-2 (COX-2) inhibitors, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and mixtures of two or more thereof. The nitrosated NSAID, the nitric oxide donor and/or therapeutic agent, can be separate components in the kit or can be in the form of a composition in the kit in one or more pharmaceutically acceptable carriers.

DETAILED DESCRIPTION OF THE INVENTION

As used throughout the disclosure, the following terms, unless otherwise indicated, shall be understood to have the following meanings.

"Gastrointestinal disorder" refers to any disease or disorder of the upper gastrointestinal tract of a patient including, for example, inflammatory bowel disease, Crohn's disease, gastritis, irritable bowel syndrome, constipation, ulcerative colitis, peptic ulcers, stress ulcers, bleeding ulcers, gastric hyperacidity, dyspepsia, gastroparesis, Zollinger-Ellison syndrome, gastroesophageal reflux disease, bacterial infections (including, for example, a *Helicobacter Pylori* associated disease), short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns.

"Upper gastrointestinal tract" refers to the esophagus, the stomach, the duodenum and the jejunum.

"Ulcers" refers to lesions of the upper gastrointestinal tract lining that are characterized by loss of tissue. Such ulcers include gastric ulcers, duodenal ulcers and gastritis.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cardiovascular disease or disorder" refers to any cardiovascular disease or disorder known in the art, including, but not limited to, restenosis, atherosclerosis, atherogenesis, angina, (particularly chronic, stable angina pectoris), aneurysm, ischemic disease, congestive heart failure or pulmonary edema associated with acute myocardial infarction, thrombosis, controlling blood pressure in hypertension (especially hypertension associated with cardiovascular surgical procedures), cardiac transplant atherosclerosis, myocardial infarction, hypertension, ischemia, embolism, stroke, thrombosis, venous thrombosis, thromboembolism, thrombotic occlusion and reclusion, shock, coronary plaque inflammation, thromboembolic events, platelet aggregation, platelet adhesion, smooth muscle cell proliferation, vascular grafting, coronary artery bypass surgery, revascularization procedures, such as, for example, angioplasty, stent placement, endarterectomy, vascular procedures involving arteries, veins, capillaries, and the like; vascular complications associated with the use of medical devices, wounds associated with the use of medical devices, cerebrovascular ischemic events, and the like. Complications associated with the use of medical devices may occur as a result of increased platelet deposition, activation, thrombus formation or consumption of platelets and coagulation proteins. Such complications, which are within the definition of "cardiovascular disease or disorder," include, for example, myocardial infarction, ischemic stroke, transient ischemic stroke, thromboembolic events, pulmonary thromboembolism, cerebral thromboembolism, thrombophlebitis, thrombocytopenia, bleeding disorders and/or any other complications which occur either directly or indirectly as a result of the foregoing disorders.

"Restenosis" is a cardiovascular disease or disorder that refers to the closure of a peripheral or coronary artery following trauma to the artery caused by an injury such as, for example, angioplasty, balloon dilation, atherectomy, laser ablation treatment or stent insertion. Restenosis can also occur following a number of invasive surgical techniques, such as, for example, transplant surgery, vein grafting, coronary artery bypass surgery, endarterectomy, heart transplantation, balloon angioplasty, atherectomy, laser ablation, endovascular stenting, and the like.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances such as growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery. Atherosclerotic cardiovascular disease, coronary heart disease (also known as coronary artery disease or ischemic heart disease), cerebrovascular disease and peripheral vessel disease are all common manifestations of atherosclerosis and are therefore encompassed by the terms "atherosclerosis" and "atherosclerotic disease".

"Thromboembolic events" includes, but is not limited to, ischemic stroke, transient ischemic stroke, myocardial infarction, angina pectoris, thrombosis, thromboembolism, thrombotic occlusion and reocclusion, acute vascular events, restenosis, transient ischemic attacks, and first and subsequent thrombotic stroke. Patients who are at risk of developing thromboembolic events, may include those with a familial history of, or genetically predisposed to, thromboembolic disorders, who have had ischemic stroke, transient ischemic stroke, myocardial infarction, and those with unstable angina pectoris or chronic stable angina pectoris and patients with altered prostacyclin/thromboxane $A_2$ homeostasis or higher than normal thromboxane $A_2$ levels leading to increase risk for thromboembolism, including patients with diabetes and rheumatoid arthritis.

"Therapeutic agent" includes any therapeutic agent that can be used to treat or prevent the diseases described herein. "Therapeutic agents" include, for example, steroids, COX-2 inhibitors, nonsteroidal antiinflammatory compounds, 5-lipoxygenase inhibitors, leukotriene $B_4$ receptor antagonists, leukotriene $A_4$ hydrolase inhibitors, 5-HT agonists, 3-hydroxy-3-methylglutaryl coenzyme A inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like. Therapeutic agent includes the pro-drugs and pharmaceutical derivatives thereof including but not limited to the corresponding nitrosated and/or nitrosylated derivatives. Although nitric oxide donors have therapeutic activity, the term "therapeutic agent" does not include the nitric oxide donors described herein, since nitric oxide donors are separately defined.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 µM and a cyclooxygenase-1 $IC_{50}$ of greater than about 5 µM, in the human whole blood COX-2 assay (as described in Brideau et al., *Inflamm Res.*, 45: 68-74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 µM, and preferably of greater than 20 µM. The compound can also inhibit the enzyme, lipoxygenase. Such selectivity may indicate an ability to reduce the incidence of common NSAID-induced side effects.

"Thromboxane inhibitor" refers to any compound that reversibly or irreversibly inhibits thromboxane synthesis, and includes compounds which are the so-called thromboxane $A_2$ receptor antagonists, thromboxane $A_2$ antagonists, thromboxane $A_2$/prostaglandin endoperoxide antagonists, thromboxane receptor (TP) antagonists, thromboxane antagonists, thromboxane synthase inhibitors, and dual acting thromboxane synthase inhibitors and thromboxane receptor antagonists. The characteristics of the preferred thromboxane inhibitor should include the suppression of thromboxane $A_2$ formation (thromboxane synthase inhibitors) and/or blockade of thromboxane $A_2$ and prostaglandin $H_2$ platelet and vessel wall (thromboxane receptor antagonists). The effects should block platelet activation and therefore platelet function.

"Thromboxane $A_2$ receptor antagonist" refers to any compound that reversibly or irreversibly blocks the activation of any thromboxane $A_2$ receptor.

"Thromboxane synthase inhibitor" refers to any compound that reversibly or irreversibly inhibits the enzyme thromboxane synthesis thereby reducing the formation of thromboxane $A_2$. Thromboxane synthase inhibitors may also increase the synthesis of antiaggregatory prostaglandins including prostacyclin and prostaglandin $D_2$. Thromboxane $A_2$ receptor antagonists and thromboxane synthase inhibitors and can be identified using the assays described in Tai, Methods of Enzymology, Vol. 86, 110-113 (1982); Hall, *Medicinal Research Reviews,* 11:503-579 (1991) and Coleman et al., *Pharmacol Rev.,* 46: 205-229 (1994) and references therein, the disclosures of each of which are incorporated by reference herein in their entirety.

"Dual acting thromboxane receptor antagonist and thromboxane synthase inhibitor" refers to any compound that simultaneously acts as a thromboxane $A_2$ receptor antagonist and a thromboxane synthase inhibitor.

"Thrombin inhibitors" refers to and includes compounds that inhibit hydrolytic activity of thrombin, including the catalytic conversion of fibrinogen to fibrin, activation of Factor V to Va, Factor VIII to VIIIa, Factor XIII to XIIIa and platelet activation. Thrombin inhibitors may be identified using assays described in Lewis et at., Thrombosis Research. 70: 173-190 (1993).

"Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation which depends on the interaction between the ligand and its specific platelet surface receptor.

"Platelet activation" refers either to the change in conformation (shape) of a cell, expression of cell surface proteins (e.g., the IIb/IIIa receptor complex, loss of GPIb surface protein), and secretion of platelet derived factors (e.g., serotonin, growth factors).

"Patient" refers to animals, preferably mammals, most preferably humans, and includes males and females, and children and adults.

"Therapeutically effective amount" refers to the amount of the compound and/or composition that is effective to achieve its intended purpose.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, $NO\bullet$), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO–, $NO\bullet$), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$-$C_4$ hydrocarbon that can comprise one or two carbon-carbon double bonds.

"Substituted alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamido and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbornyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$-$C_{10}$ hydrocarbon (preferably a $C_2$-$C_8$ hydrocarbon, more preferably a $C_2$-$C_6$ hydrocarbon) which can comprise one or more carbon-carbon triple bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxo" refers to =O.

"Oxy" refers to —O⁻$R_{77}^+$ wherein $R_{77}$ is an organic or inorganic cation.

"Oxime" refers to (=N—$OR_{81}$) wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone refers to (=N—N($R_{81)}$)($R'_{81}$)) wherein $R'_{81}$ is independently selected from $R_{81}$, and $R_{81}$ is as defined herein.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{52}R_{53}N$—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino or arylalkylamino" refers to $R_{52}R_{55}N$—, wherein $R_{52}$ is an alkyl group, as defined herein, and $R_{55}$ is an aryl group, as defined herein.

"Alkylarylalkylamino" refers to $R_{52}R_{79}N$—, wherein $R_{52}$ is an alkyl group, as defined herein, and $R_{79}$ is an arylalkyl group, as defined herein.

"Alkylcycloalkylamino" refers to $R_{52}R_{80}N$—, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —$S(O)_2^-$.

"Sulfonic acid" refers to —$S(O)_2OR_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein "Sulfonic ester" refers to —$S(O)_2OR_{58}$, wherein $R_{58}$ is an alkyl group, an aryl group, or an aryl heterocyclic ring, as defined herein.

"Sulfonamido" refers to —$S(O)_2$—N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S$—, wherein $R_{50}$ is an alkyl group, as defined herein (preferably a lower alkyl group, as defined herein).

"Arylthio" refers to $R_{55}S$—, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}$—S(O)—, wherein $R_{50}$ is an alkyl group, as defined herein.

"Alkylsulfonyl" refers to $R_{50}$—$S(O)_2$—, wherein $R_{50}$ is an alkyl group, as defined herein.

"Alkylsulfonyloxy" refers to $R_{50}$—$S(O)_2$—O—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—$S(O)_2$—, wherein $R_{55}$ is an aryl group, as defined herein.

"Arylsulfonyloxy" refers to $R_{55}$—$S(O)_2$—O—, wherein $R_{55}$ is an aryl group, as defined herein.

"Amidyl" refers to $R_{51}C(O)N(R_{57})$— wherein $R_{51}$ and $R_{57}$ are each independently a hydrogen atom, an alkyl group, an aryl group or an arylheterocyclic ring, as defined herein.

"Ester" refers to $R_{51}C(O)O$— wherein $R_{51}$ is a hydrogen atom, an alkyl group, an aryl group or an arylheterocyclic ring, as defined herein.

"Carbamoyl" refers to —O—C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —$C(O)OR_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$-$R_{52}$—C(O)—, wherein $R_{55}$ is an aryl group, as defined herein, and $R_{52}$ is an alkyl group, as defined herein.

"Alkylarylcarbonyl" refers to $R_{52}$-$R_{55}$—C(O)—, wherein $R_{55}$ is an aryl group, as defined herein, and $R_{52}$ is an alkyl group, as defined herein.

"Heterocyclicalkylcarbonyl" refer to $R_{78}$C(O)— wherein $R_{78}$ is a heterocyclicalkyl group, as defined herein.

"Carboxylic ester" refers to —C(O)O$R_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

The NSAIDs that are nitrosated in accordance with the invention and/or are included in the compositions of the invention can be any of those known in the art, including those exemplified below.

Despite the introduction of many new drugs, aspirin (acetylsalicylic acid) is still the most widely prescribed antiinflammatory, analgesic and antipyretic compound and is a standard for the comparison and evaluation of all other NSAIDs. Salicylic acid itself is so irritating that it can only be used externally. However, derivatives, particularly salicylate esters and salts, have been prepared which provide ingestible forms of the salicylates which have the desired antiinflammatory and other properties. In addition to aspirin, which is the acetate ester of salicylic acid, are the difluorophenyl derivative (diflunisal) and salicylsalicylic acid (salsalate). Also available are the salts of salicylic acid, principally sodium salicylate. Sodium salicylate and aspirin are the two most commonly used preparations for systemic treatment. Other salicylates include salicylamide, sodium thiosalicylate, choline salicylate and magnesium salicylate. Also available are combinations of choline and magnesium salicylates. Also contemplated for use in the present invention are 5-aminosalicylic acid (mesalamine), salicylazosulfapyridine (sulfasalazine) and methylsalicylate.

Another group of NSAIDs are the pyrazolon derivatives, which include, for example, phenylbutazone, oxyphenbutazone, antipyrine, aminopyrine, dipyrone and apazone (azapropazone).

Another group of NSAIDs are the para-aminophenol derivatives, which are the so-called "coal tar" analgesics, including, for example, phenacetin and its active metabolite acetaminophen.

Another group of compounds for use in the present invention include indomethacin, a methylated indole derivative, and the structurally related compound sulindac.

Also contemplated is a group of compounds referred to as the fenamates which are derivatives of N-phenylanthranilic acid. The most well known of these compounds is mefenamic, meclofenamic, flufenamic, tolfenamic and etofenamic acids. They are used either as the acid or as pharmaceutically acceptable salts.

Another contemplated NSAID is tolmetin which, like the other NSAIDs discussed herein, causes gastric erosion and prolonged bleeding time.

Another group of NSAIDs are the propionic acid derivatives. Principal members of this group are, for example, ibuprofen, naproxen, flurbiprofen, fenoprofen and ketoprofen. Other members of this group, in use or study in countries outside the U.S., include, for example, fenbufen, pirprofen, oxaprozin, indoprofen and tiaprofenic acid.

Also contemplated for use in the invention is diclofenac, one of the series of phenylacetic acid derivatives that have been developed as antiinflammatory compounds. Other NSAIDs which are contemplated as suitable in the present invention include etodolac and nabumentone.

Each of the above NSAIDs is described more fully in the literature, such as in Goodman and Gilman, The Pharmacological Basis of Therapeutics (9th Edition), McGraw-Hill, 1995, Pgs. 617-657; the Merck Index on CD-ROM, 13th Edition; and in U.S. Pat. Nos. 6,057,347 and 6,297,260 assigned to NitroMed. Inc., the disclosures of each of which are incorporated by reference herein in their entirety.

In one embodiment, the invention describes nitrosated NSAIDs of Formula (I) and pharmaceutically acceptable salts thereof:

(I)

$$R_n-\underset{\underset{H}{|}}{\overset{\overset{R_m}{|}}{C}}-\overset{\overset{O}{\|}}{C}-X$$

wherein:
$R_m$ is a hydrogen or a lower alkyl group;
$R_n$ is:

(1)

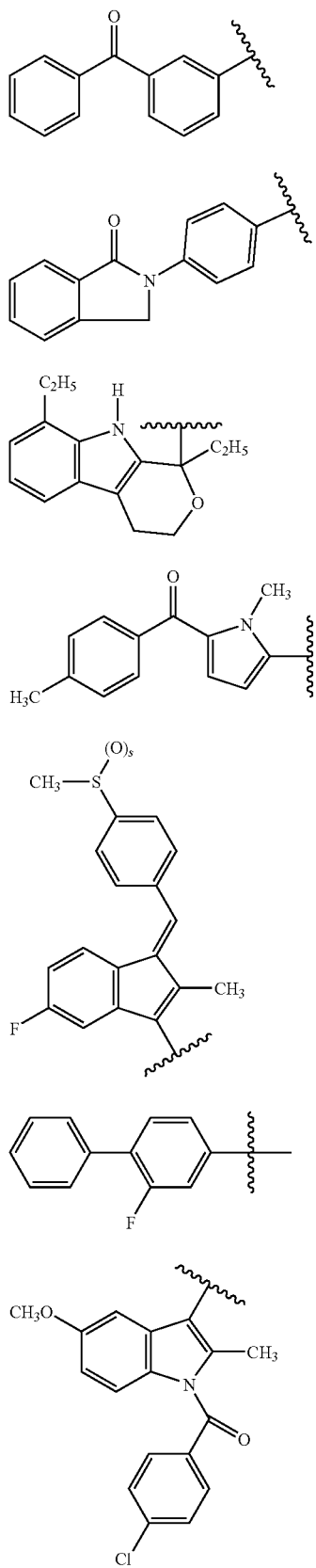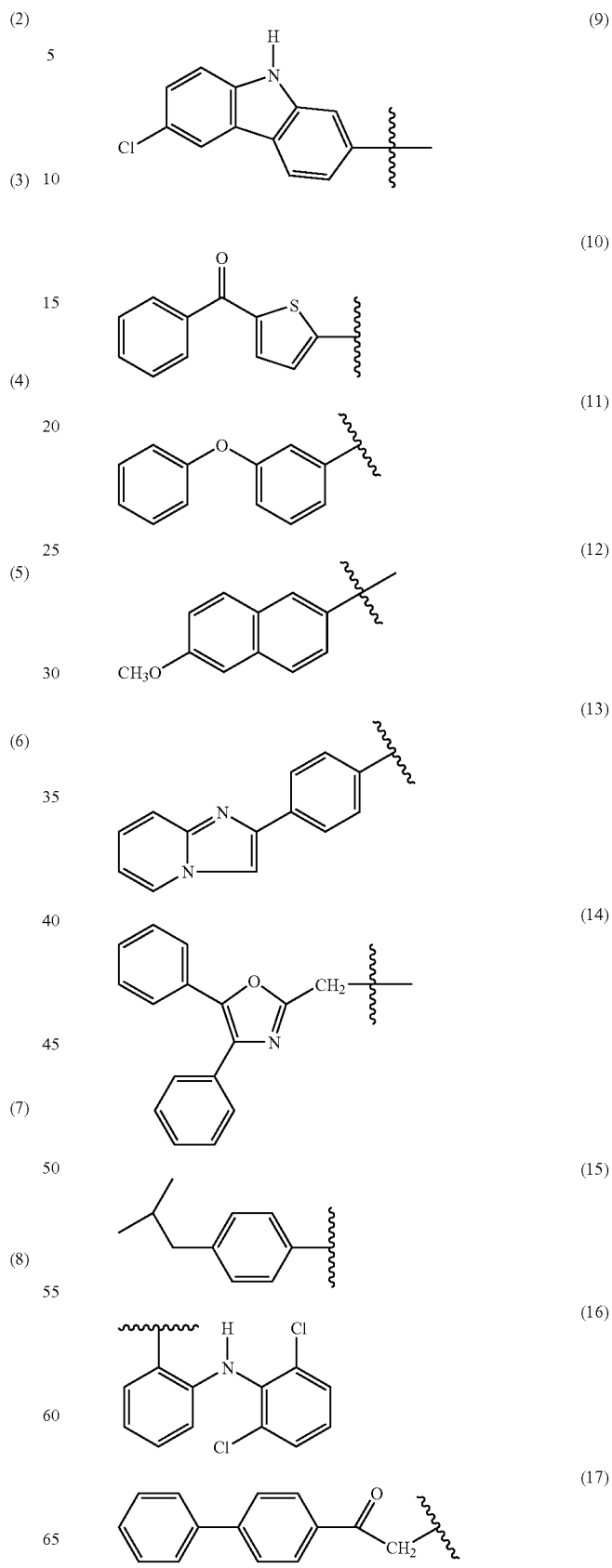

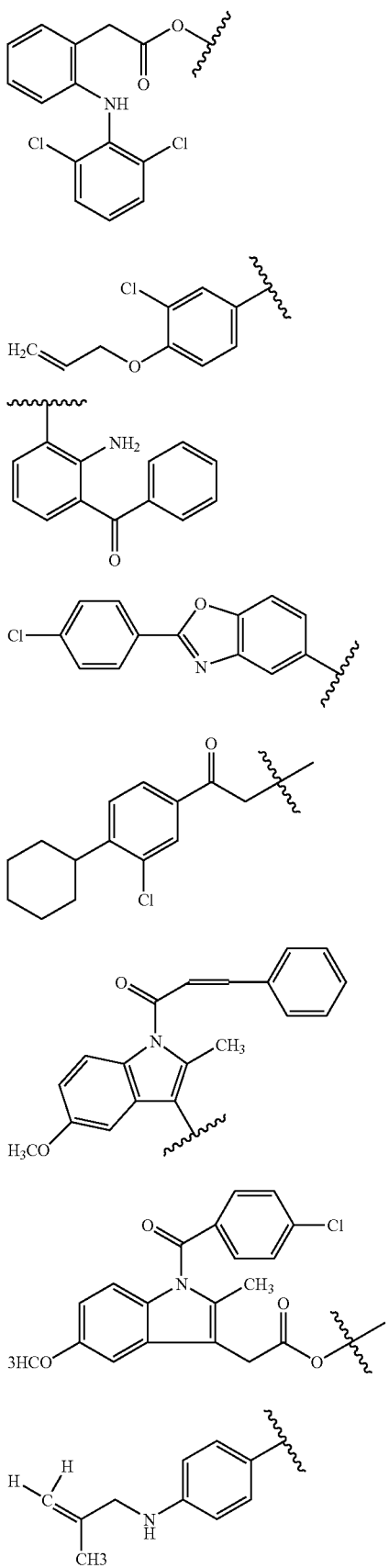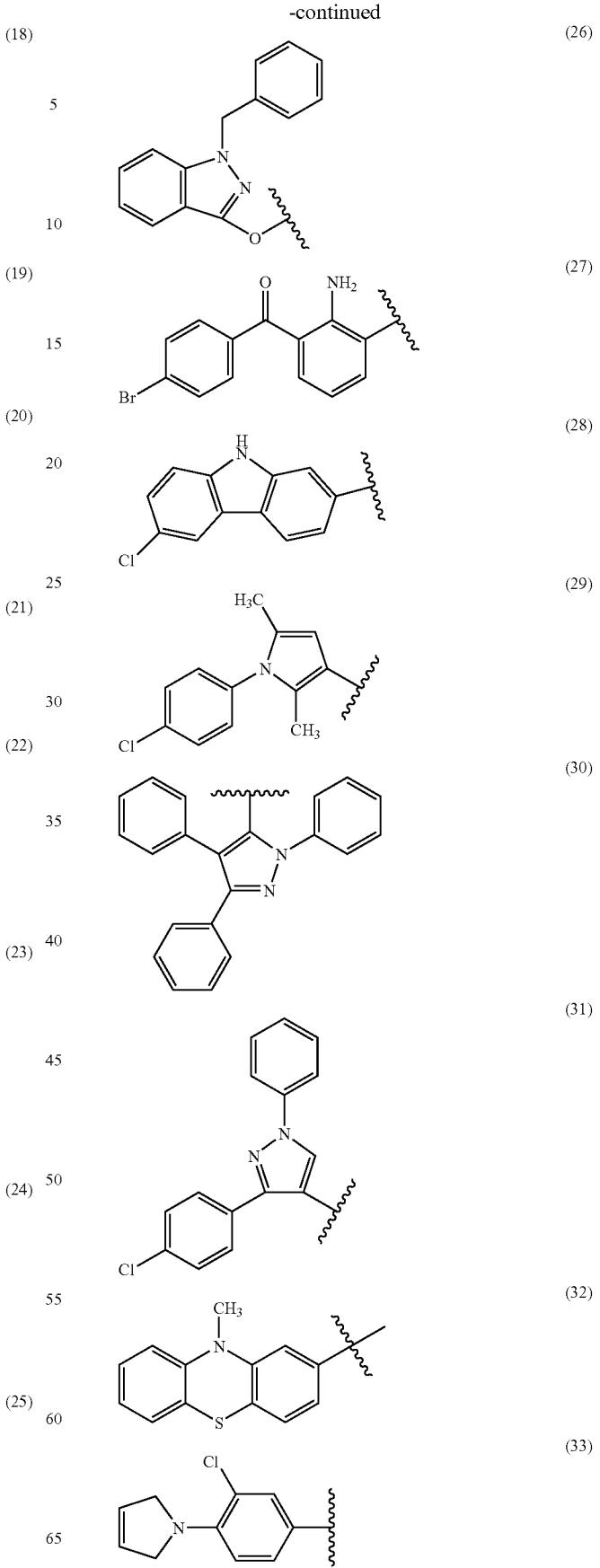

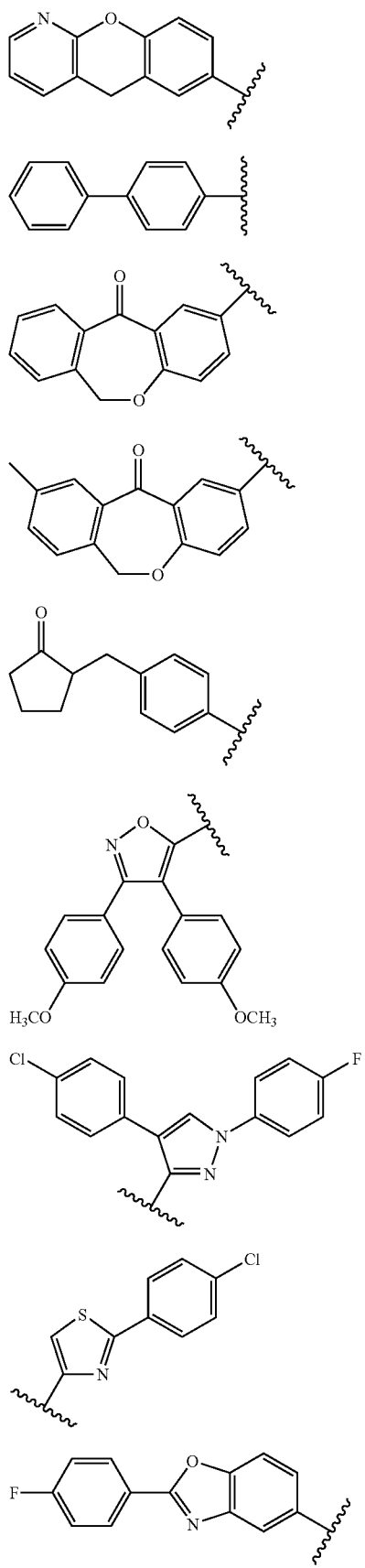
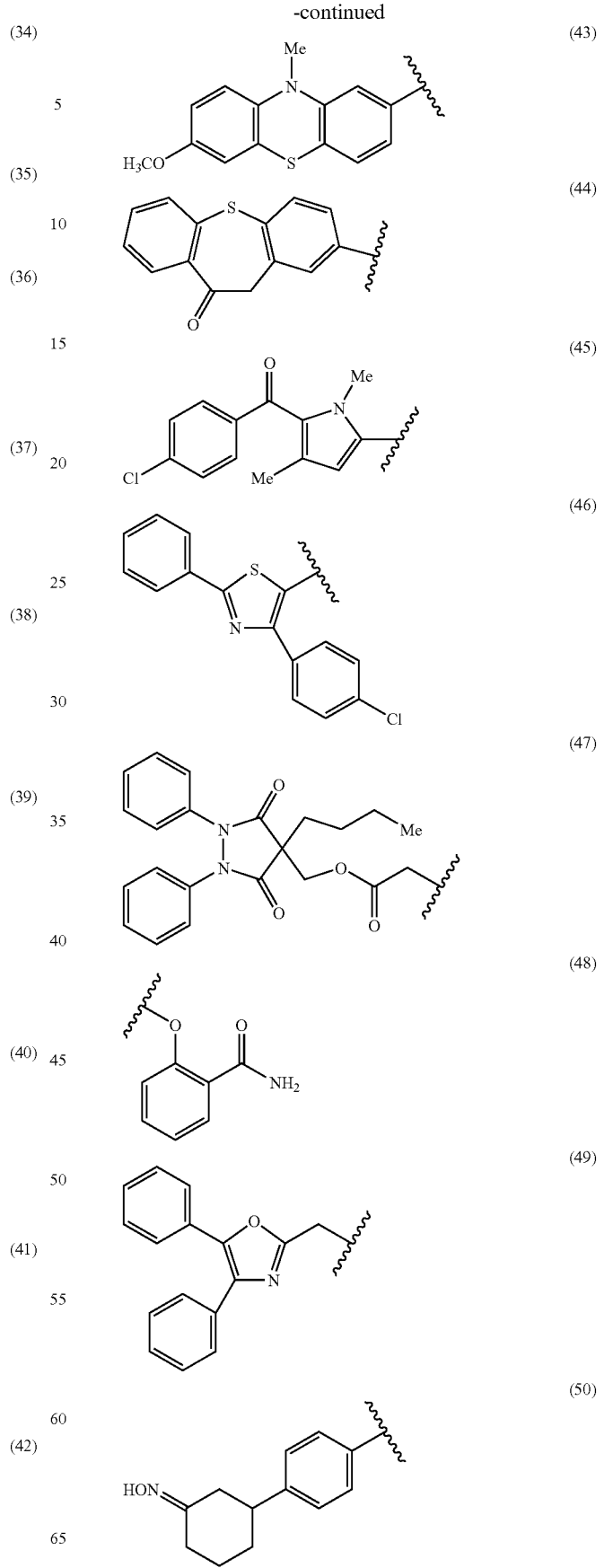

-continued

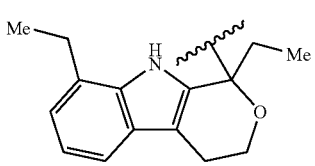
(51)

s is an integer of 0 or 1;
X is:
(1) —Y—(CR$_4$C$_4$')$_p$-T-(CR$_4$R$_4$')$_p$—ONO$_2$;

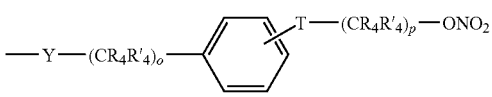
(2)

wherein T is ortho, meta or para;

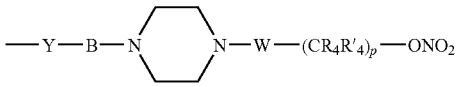
(3)

(4) —Y—(CR$_4$C$_4$')$_p$—V—B-T-(CR$_4$R$_4$')$_p$—ONO$_2$;
(5) —Y—(CR$_4$R$_4$')$_p$-T-C(O)—(CR$_4$R$_4$')$_o$—(CH$_2$)—ONO$_2$;
(6) —Y—(CR$_4$R$_4$')$_p$—C(Z)—(CH$_2$)$_q$-T-(CR$_4$R$_4$')$_q$—(CH$_2$)—ONO$_2$;
(7) —Y—(CR$_4$R$_4$')$_p$-T-(CH$_2$)$_q$—V—(CR$_4$R$_4$')$_q$—(CH$_2$)—ONO$_2$;
(8) —Y—(CR$_4$R$_4$')$_p$—V—(CH$_2$)$_q$—V—(CR$_4$R$_4$')$_q$—(CH$_2$)—ONO$_2$;
(9) —Y—(CR$_4$R$_4$')$_o$—(W)$_q$—(CR$_4$R$_4$')$_o$—(CH$_2$)—ONO$_2$;
(10) —NR$_j$—O—(CH$_2$)$_o$—V—(CR$_4$R$_4$')$_q$(CH$_2$)—ONO$_2$;
(11) —NR$_j$—O—(CH$_2$)$_o$—(W)$_q$—(CR$_4$R$_4$')$_q$—(CH$_2$)—ONO$_2$;
(12) —O—NR$_j$—(CH$_2$)$_o$—(W)$_q$—(CR$_4$R$_4$')$_q$—(CH$_2$)—ONO$_2$;
(13) —Y—(CH$_2$)$_o$—(W)$_q$—(CH$_2$)$_o$—V—(CR$_4$R$_4$')$_o$-Q'-(CR$_4$R$_4$')$_o$—(CH$_2$)—ONO$_2$;
(14) —Y—(CR$_4$R$_4$')$_p$—V—(CH$_2$)$_o$—(W)$_q$—(CR$_4$R$_4$')$_q$—(CH$_2$)—ONO$_2$;
(15) —O—NR$_4$R$_4$')$_o$—(CH$_2$)$_o$—V—(CR$_4$R$_4$')$_q$—(CH$_2$)—ONO$_2$;
(16) —Y—(CR$_4$R$_4$')$_o$-Q'-(CR$_4$R$_4$')$_o$—V—(CR$_4$R$_4$')$_o$—(CH$_2$)—ONO$_2$;
(17) —Y—(CR$_4$R$_4$')$_o$-Q'-(CR$_4$R$_4$')$_o$—(W)$_q$—(CR$_4$R$_4$')$_o$—(CH$_2$)—ONO$_2$;
(18) —Y—(CR$_4$R$_4$')$_p$-T-(CR$_4$R$_4$')$_p$-Q'-(CR$_4$R$_4$')$_o$—(CH$_2$)—ONO$_2$;
(19) —Y—(CR$_4$R$_4$')$_q$—C(Z)—(CR$_4$R$_4$')$_o$—(CH$_2$)—ONO$_2$;
(20) —Y—(CR$_4$R$_4$')$_p$-Q'-(CR$_4$R$_4$')$_o$—(CH$_2$)—ONO$_2$;
(21) —Y—(CR$_4$R$_4$')$_q$—P(O)MM';
(22) —Y—(CR$_4$R$_4$')$_o$-Q'-(CR$_4$R$_4$')$_o$—(CH$_2$)—ONO$_2$;
(23) —Y—(CR$_4$R$_4$')$_o$-Q'-(CR$_4$R$_4$')$_o$-T-(CR$_4$R$_4$')$_o$—(CH$_2$)—ONO$_2$;
(24) —Y—(CR$_4$R$_4$')$_q$—(W)$_q$—(CR$_4$R$_4$')$_o$-Q'-(CR$_4$R$_4$')$_o$—(CH$_2$)—ONO$_2$;
(25) —Y—(CR$_4$R$_4$')$_q$—V—(CR$_4$R$_4$')$_o$-Q'-(CR$_4$R$_4$')$_o$—(CH$_2$)—ONO$_2$;
(26) —Y—(CR$_4$R$_4$')$_p$-(T)$_o$-(W)$_q$—(CR$_4$R$_4$')$_o$—(CH$_2$)—ONO$_2$;
(27) —Y—(CR$_4$R$_4$')$_p$—(W)$_q$-(T)$_o$-(CR$_4$R$_4$')$_o$—(CH$_2$)—ONO$_2$;
(28) —Y—(CR$_4$R$_4$')$_q$—C(Z)—V—(CR$_4$R$_4$')$_q$—(CH$_2$)—ONO$_2$;
(29) —Y—(CR$_4$R$_4$')$_o$—C(R$_4$)(ONO$_2$)—(CR$_4$R$_4$')$_q$-(T)$_o$-(W)$_q$-(T)$_o$-(CR$_4$R$_4$')$_o$—R$_5$;
(30) —Y—(CR$_4$R$_4$')$_o$—V—(CR$_4$R$_4$')$_o$-Q'-(CR$_4$R$_4$')$_o$—(CH$_2$)—ONO$_2$;
(31) —Y—(CR$_4$R$_4$')$_q$—C(Z)-Q'-(CR$_4$R$_4$')$_o$—(CH$_2$)—ONO$_2$;
(32) —Y—(CR$_4$R$_4$')$_p$—V—(CR$_4$R$_4$')$_p$—(CH$_2$)—ONO$_2$;
(33) —Y—(CR$_4$R$_4$')$_p$—V—(CH$_2$)$_q$-(T)$_o$-(CR$_4$R$_4$')$_q$—(CH$_2$)—ONO$_2$;
(34) —Y—(CR$_4$R$_4$')$_p$-(T)$_o$-Q'-(T)$_o$-(CR$_4$R$_4$')$_q$—(CH$_2$)—ONO$_2$;
(35) —Y—(CR$_4$R$_4$')$_q$—C(Z)—(CR$_4$R$_4$')$_q$—V—(CR$_4$R$_4$')$_o$-Q'-(CR$_4$R$_4$')$_o$—(CH$_2$)—ONO$_2$;
(36) —Y—(CR$_4$R$_4$')$_q$—C(Z)—(CR$_4$R$_4$')$_q$—(W)$_q$—(CR$_4$R$_4$')$_o$-Q'-(CR$_4$R$_4$')$_o$—(CH$_2$)—ONO$_2$;
(37) —NR$_j$—O—(CH$_2$)$_o$—V—(CR$_4$R$_4$')$_o$-Q'-(CH$_2$)—ONO$_2$;
(38) —NR$_j$—O—(CH$_2$)$_o$—(W)$_q$—(CR$_4$R$_4$')$_o$-Q'-(CH$_2$)—ONO$_2$;
(39) —O—NR$_j$—(CH$_2$)$_o$—(W)$_q$—(CR$_4$R$_4$')$_o$-Q'-(CH$_2$)—ONO$_2$;
(40) —O—NR$_j$—(CH$_2$)$_o$—V—(CR$_4$R$_4$')$_o$-Q'-(CH$_2$)—ONO$_2$;
(41) —NR$_j$—NR$_j$—(CR$_4$R$_4$')$_p$—(W)$_q$-(T)$_o$-(CR$_4$R$_4$')$_o$—(CH$_2$)—ONO$_2$; or
(42) —Y—(CR$_4$R$_4$')$_p$—Y—C(O)C(R$_m$)(R$_n$) with the proviso that at least one R$_4$ or R$_4$' must be —ONO$_2$ or —CH$_2$ONO$_2$, and R$_m$ and R$_n$, are as defined herein in Formula (I);
(43) —Y—(CR$_4$R$_4$')$_o$-Q'-(CR$_4$R$_4$')$_o$—ONO$_2$; or
(44) —Y—(CR$_4$R$_4$')$_o$—V—(CR$_4$R$_4$')$_o$-Q-(CR$_4$R$_4$')$_o$—ONO$_2$;

R$_4$ and R$_4$' at each occurrence are independently a hydrogen, lower alkyl group, —OH, —CH$_2$OH, —ONO$_2$, —NO$_2$ or —CH$_2$ONO$_2$; or R$_4$ and R$_4$' taken together with the carbon atom to which they are attached are a cycloalkyl group or a heterocyclic ring;

V is —C(O)-T-, -T-C(O)—, -T-C(O)-T or T-C(O)—C(O)-T;

W is a covalent bond or a carbonyl group;

T at each occurrence is independently an oxygen, (S(O)$_o$)$_o$ or NR$_j$;

R$_j$ is a hydrogen, an alkyl group, an aryl group, a heterocyclic ring, an alkylcarbonyl group, an alkylaryl group, an alkylsulfinyl group, an alkylsulfonyl group, an arylsulfinyl group, an arylsulfonyl group, a sulfonamido group, a N-alkylsulfonamido group, a N,N-diarylsulfonamido group, a N-arylsulfonamido group, a N-alkyl-N-arylsulfonamido group, a carboxamido group or a hydroxyl group;

p at each occurrence is independently an integer from 1 to 6;

q at each occurrence is independently an integer from 1 to 3;

o at each occurrence is independently an integer from 0 to 2;

Y is oxygen or sulfur (—S—);

B is either phenyl or (CH$_2$)$_o$;

Q' is a cycloalkyl group, a heterocyclic ring or an aryl group;

Z is (=O), (=N—OR$_5$), (=N—NR$_5$R'$_5$) or (=CR$_5$R'$_5$);

M and M' are each independently —O⁻H₃N⁺—(CR₄R+₄)_q —CH₂ONO₂ or -T-(CR₄R'₄)_o—CH₂ONO₂;

R₅ and R₅' at each occurrence are independently a hydrogen, a hydroxyl group, an alkyl group, an aryl group, an alkylsulfonyl group, an arylsulfonyl group, a carboxylic ester, an alkylcarbonyl group, an arylcarbonyl group, a carboxamido group, an alkoxyalkyl group, an alkoxyaryl group, a cycloalkyl group or a heterocyclic ring; and with the proviso that for X in the compounds of Formulas (I) and (II):

when Y is oxygen or sulfur in Formula 1, T is —N(CH₃) and R₄ and R₄' are hydrogen, p cannot be the integer 2;

when Y is oxygen or sulfur in Formula 1, and T is oxygen, at least one R₄ or R₄' must be —OH, —NO₂ or —CH₂ONO₂ or R₄ and R₄' taken together with the carbon atom to which they are attached are a cycloalkyl group or a heterocyclic ring;

when Y is oxygen or sulfur in Formula 9, and W is a covalent bond, at least one R₄ or R₄' must be —OH, —ONO₂, —NO₂ or —CH₂ONO₂ or R₄ and R₄' taken together with the carbon atom to which they are attached are a cycloalkyl group or a heterocyclic ring;

when Y is oxygen or sulfur in Formula 17, and W is a covalent bond, and R₄ and R₄' are each independently a hydrogen or a lower alkyl group, Q' cannot be a phenyl group or a saturated, unsaturated or aromatic heterocyclic ring having 5 or 6 atoms, containing one to three heteroatoms, wherein the heteroatoms are each independently nitrogen, oxygen or sulfur;

when Y is oxygen in Formula 17, and W is a covalent bond, and R₄ and R₄' are hydrogen, Q' cannot be a cycloalkyl group;

when Y is oxygen or sulfur in Formula 20, 22 or 43, and R₄ and R₄' are each independently a hydrogen or a lower alkyl group, Q' cannot be a phenyl group or a saturated, unsaturated or aromatic heterocyclic ring having 5 or 6 atoms, containing one to three heteroatoms, wherein the heteroatoms are each independently nitrogen, oxygen or sulfur;

when Y is oxygen in Formula 20, 22 or 43, and W is a covalent bond, and R₄ and R₄' are hydrogen, Q' cannot be a cycloalkyl group;

when Y is oxygen or sulfur in Formula 26 or 27, T is —N(CH₃), W is a covalent bond and R₄ and R₄' are hydrogen, p cannot be the integer 2, and o cannot be the integer 1 in —(CR₄R'₄)_o;

when Y is oxygen or sulfur in Formula 26 or 27, W is a covalent bond, T is oxygen and o is the integer 1, at least one R₄ or R₄' must be —OH, —NO₂ or —CH₂ONO₂ or R₄ and R₄' taken together with the carbon atom to which they are attached are a cycloalkyl group or a heterocyclic ring; and with the further proviso that the invention does not include the compounds of Formula (I), wherein R_m is a methyl group, R_n is structure 12 (i.e. naproxen) of ACS registry numbers 502158-05-6, 410071-57-7, 311336-65-9, 311336-63-7, 311336-62-6, 290335-27-2, 290335-26-1, 290335-25-0, 174454-51-4, 170591-17-0, 163133-43-5; and the compounds of Formula (I) wherein R_m is a hydrogen, R_n is structure 16 (i.e. diclofenac) of ACS registry numbers 497818-55-0, 454170-89-9, 326850-43-5, 311336-66-0, 311336-64-8, 311336-61-5, 290335-37-4, 290335-36-3, 290335-35-2, 183195-09-7, 183195-07-5, 183195-06-4, 183195-04-2, 174454-43-4, 156661-01-7; and the compounds of Formula (I) wherein R_m is a hydrogen, R_n is structure 8 (i.e. indomethacin) of ACS registry numbers 301838-28-8, 290335-34-1, 290335-33-0, 290335-32-9, 290335-31-8, 204268-63-3, 164790-49-2, 163552-70-1 and the compounds of ACS registry numbers 497818-54-9, 497818-52-7, 410071-65-7, 410071-64-6, 410071-63-5, 410071-62-4, 410071-61-3, 410071-60-2, 410071-59-9, 410071-58-8, 410071-21-5, 402831-74-7, 342774-91-8, 326850-47-9, 311336-60-4, 311336-58-0, 311336-57-9, 290335-34-1, 290335-33-0, 290335-32-9, 290335-31-8, 290335-30-7, 290335-29-4, 290335-28-3, 209002-87-9, 209002-86-8, 209002-85-7, 209002-84-6, 204633-00-1, 204268-63-3, 189282-77-7, 189282-76-6, 188209-49-9, 174454-50-3, 174454-47-8, 158836-71-6, 156970-87-5, 156970-86-4, and 156970-83-1.

In a preferred embodiment when X is Formula 42, R_m and R_n at each occurrence are the same.

In cases where multiple designations of variables that reside in sequence are chosen as a "covalent bond" or the integer chosen is 0, the intent is to denote a single covalent bond connecting one radical to another. For example, B₀ would denote a covalent bond, while B₂ denotes (B—B) and (C(R₄)(R'₄))₂ denotes —C(R₄)(R'₄)—C(R₄)(R'₄)—.

Another embodiment of the invention describes nitrosated NSAIDs of Formula (II), and pharmaceutically acceptable salts thereof:

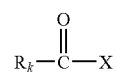

(II)

wherein:

R_k is:

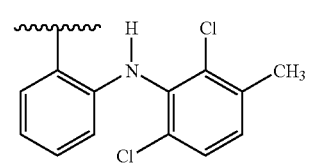

(1)

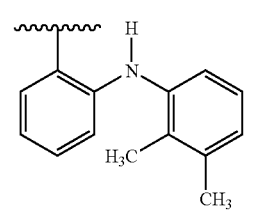

(2)

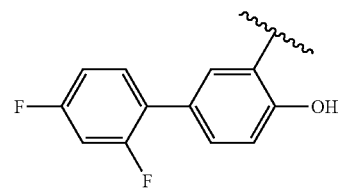

(3)

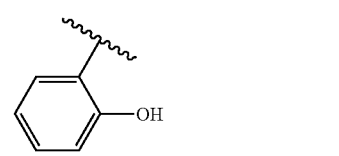

(4)

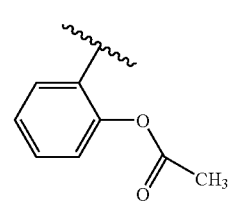

(5)

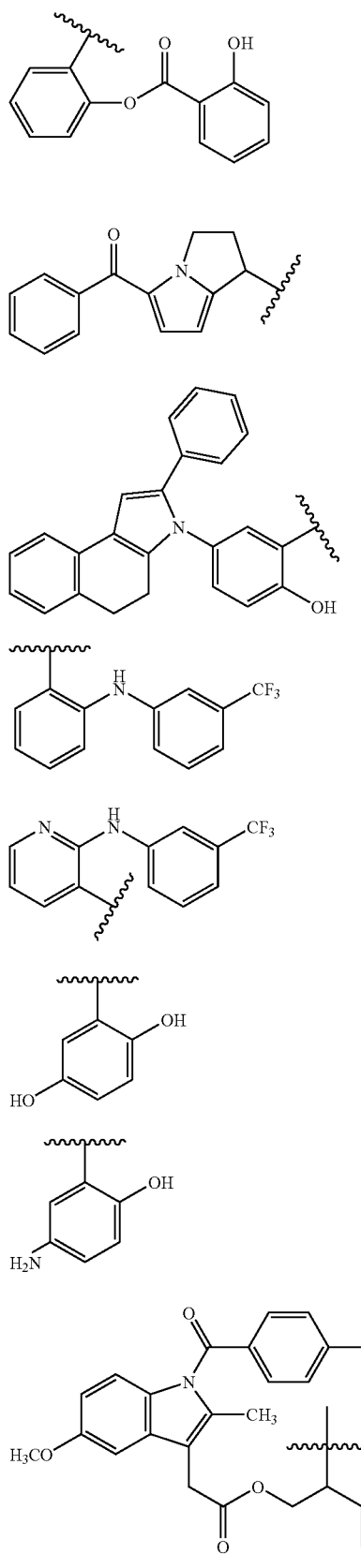
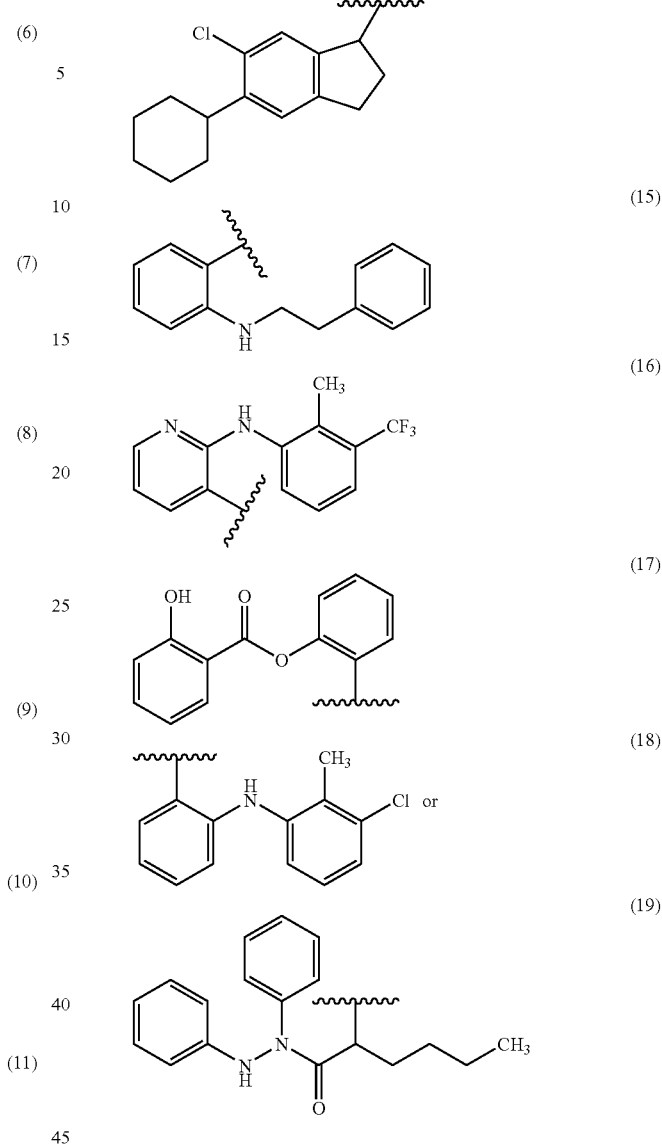

and X is as defined herein in Formula (I) or

(45) —Y—(CR₄R₄')ₚ—Y—C(O)—R_k with the proviso that at least one R₄ or R₄' must be —ONO₂ or —CH₂ONO₂, and R_k is as defined herein in Formula (II); and with the further proviso that the invention does not include the compounds of Formula (II) wherein R_k is structure 5 (i.e. aspirin) of ACS registry numbers 410071-45-3, 410071-44-2, 410071-40-8, 410071-39-5, 410071-38-4, 410071-13-5, 349472-69-1, 290335-24-9, 290335-23-8, 290335-22-7, 289056-41-3, 287118-97-2, 287118-96-1, 206556-93-6, 190442-14-9, 190442-13-8, 190442-12-7, 190442-12-7, 190442-11-6, 188025-64-1, 184644-94-8, 184644-92-6, 184644-90-4, 177598-18-4, 177598-17-3, 177598-13-9, 177598-12-8, 175033-36-0, 171781-26-3, 154424-73-4, 145585-70-2, 140218-52-6 and 140218-49-1; and the compounds of ACS registry numbers 478163-51-8, 410071-48-6, 410071-47-5, 410071-46-4, 410071-43-1, 410071-42-0, 410071-41-9, 410071-37-3, 410071-36-2, 410071-35-1, 410071-34-0, 410071-33-9, 401916-64-1, 302606-04-8, 257626-09-8, 257626-08-7, 256499-26-0, 209002-97-9, 204268-65-5, 203563-95-5, 177598-09-3, 164790-48-1 and 163385-76-0.

In a preferred embodiment when X is Formula 45, $R_k$ at each occurrence is the same.

In another embodiment, the compounds of Formula (I) and (II) do not include the compounds disclosed in, for example, U.S. Pat. Nos. 5,859,053, 6,429,223, 6,355,666, 6,436,990, 6,525,098, 6,552,078; and in U.S. Application Nos. 2002/0028845, 2003/0088111, and in WO 94/03421, WO 94/04484, WO 94/12463, WO 95/09831, WO 95/30641, WO 96/34848, WO 97/04757, WO 97/16405, WO 98/09948, WO 98/17673, WO 98/25918, WO 00/44705, WO 00/51988, WO 00/61537, WO 00/61541, WO 00/72838, WO 01/04082, WO 01/10814, WO 01/12584, WO 01/49275, WO 01/66088, WO 02/00167, WO 02/092072, WO 02/11706, WO 02/11707, WO 02/30866, WO 02/30867, WO 02/100400, WO 03/000642, WO 03/000643, WO 03/013499, WO 03/022249; and in EP 0738706 B1, EO 0440098 A1; and in Endres et al., *Eur. J. Med. Chem.* 34: 895-901 (1999); Gilmer et al., *Eur. J. Pharm Sci.*, 16: 297-304 (2002), Gilmer et al., *Eur. J. Pharm Sci.*, 14: 221-227 (2001); and Ingram et al., *J. Pharm Pharmacol.*, 53: 345-350 (2001); the disclosures of each of which are incorporated by reference herein in their entirety.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. The invention includes within its scope all such isomers and mixtures thereof.

In one embodiment of the invention, the NSAID of Formula I substituted with at least one $NO_2$ group are nitrosated derivatives of acemetacin, aceclofenac, alclofenac, alminoprofen, amfenac, bendazac, benoxaprofen, bromfenac, bucloxic acid, butibufen, carprofen, cinmetacin, clopirac, diclofenac, etodolac, felbinac, fenclozic acid, fenbufen, fenoprofen, fentiazac, flunoxaprofen, flurbiprofen, ibufenac, ibuprofen, indomethacin, isofezolac, isoxepac, indoprofen, ketoprofen, lonazolac, loxoprofen, metiazinic acid, mofezolac, miroprofen, naproxen, oxaprozin, pirozolac, pirprofen, pranoprofen, protizinic acid, salicylamide O-acetic acid, sulindac, suprofen, suxibuzone, tiaprofenic acid, tolmetin, xenbucin, ximoprofen, zaltoprofen or zomepirac and the NSAID of Formula II substituted with at least one $NO_2$ group are nitrosated derivatives of aspirin, acemetcin, bumadizon, carprofenac, clidanac, diflunisal, enfenamic acid, fendosal, flufenamic acid, flunixin, gentisic acid, ketorolac, meclofenamic acid, mefenamic acid, mesalamine, niflumic acid, salsalate, tolfenamic acid or tropensin.

In preferred embodiments for the compounds of Formula (I) or (II) and pharmaceutically acceptable salts thereof, X is:

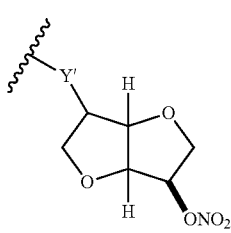

(1)

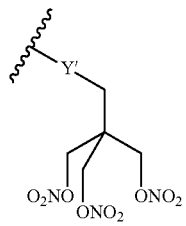

(2)

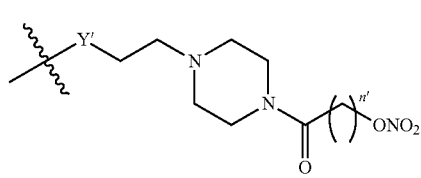

(3)

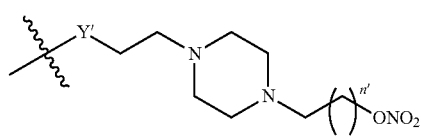

(4)

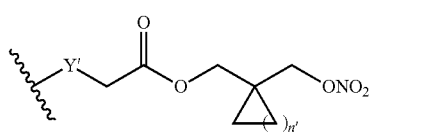

(5)

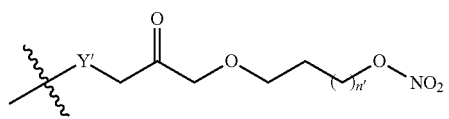

(6)

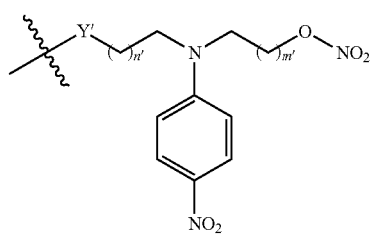

(7)

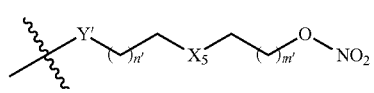

(8)

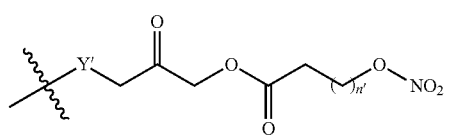

(9)

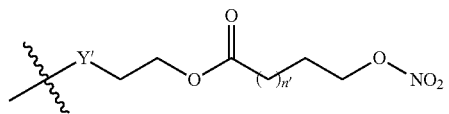

(10)

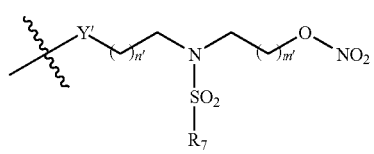

(11)

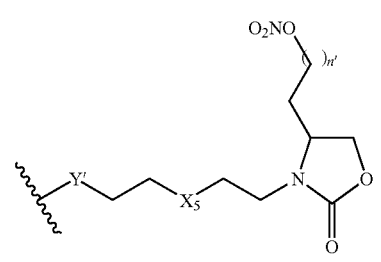 (12)
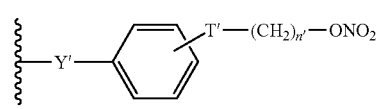 (13)
wherein T' maybe ortho, meta or para
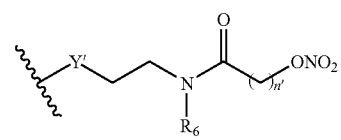 (14)
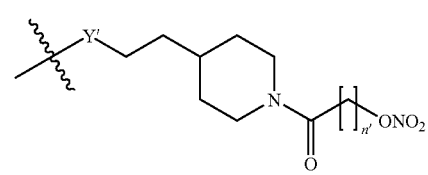 (15)
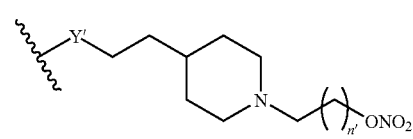 (16)
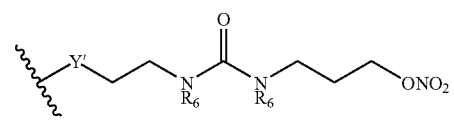 (17)
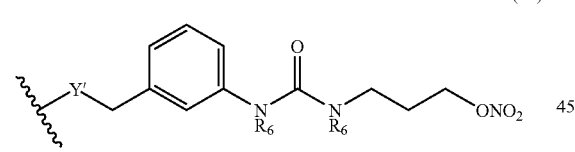 (18)
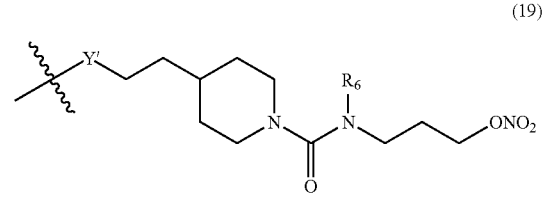 (19)
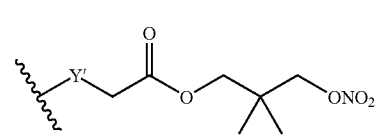 (20)
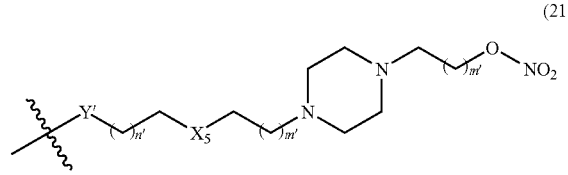 (21)
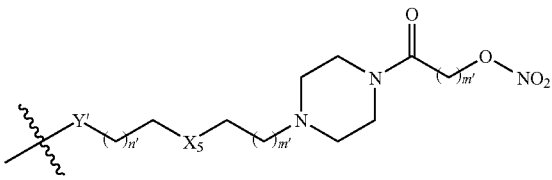 (22)
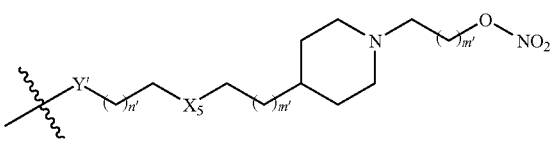 (23)
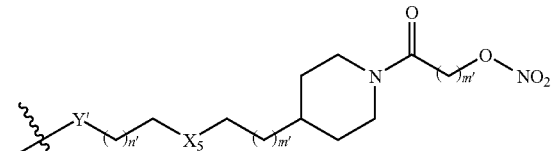 (24)
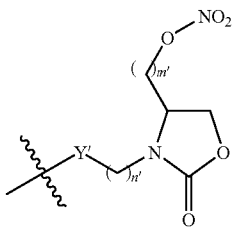 (25)
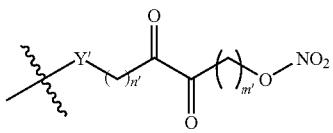 (26)
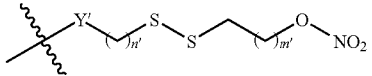 (27)
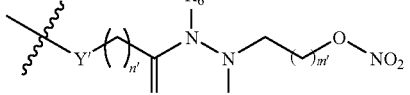 (28)
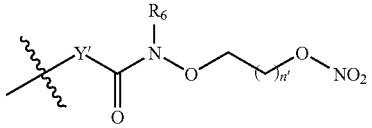 (29)
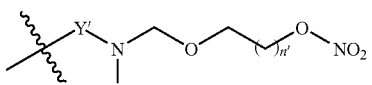 (30)
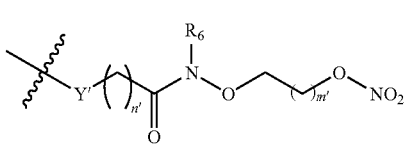 (31)

(32) 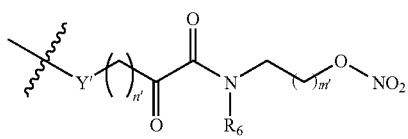
(33) 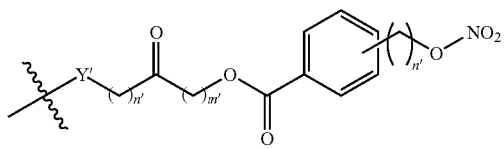
(34) 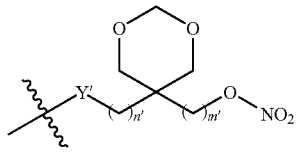
(35) 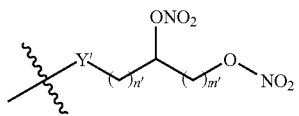
(36) 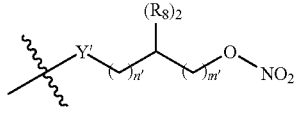
(37) 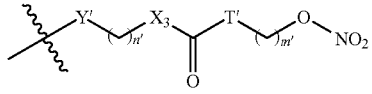
(38) 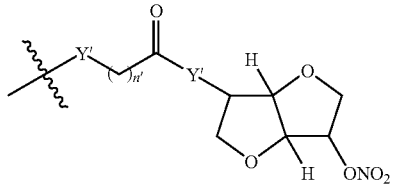
(39) 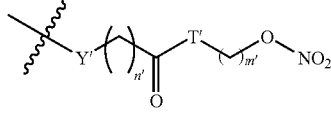
(40) 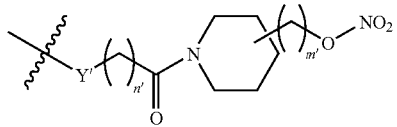
(41) 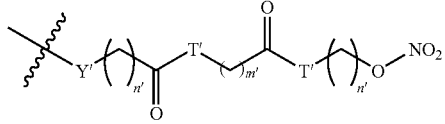
(42) 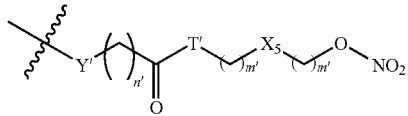
(43) 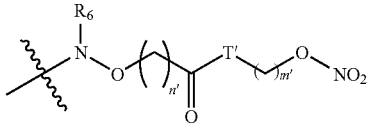
(44) 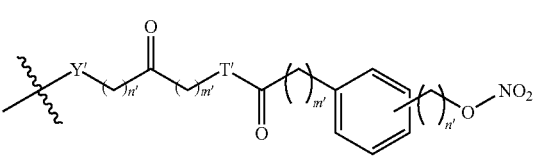
(45) 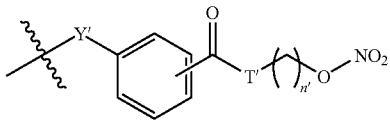
(46) 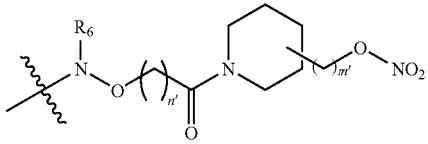
(47) 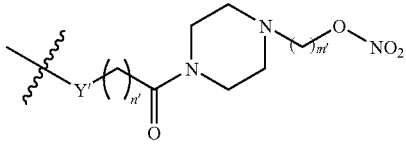
(48) 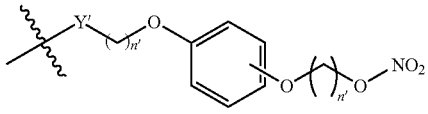
(49) 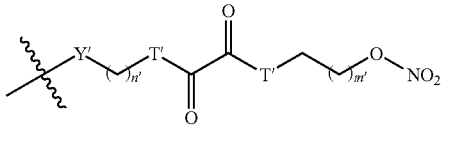
(50) 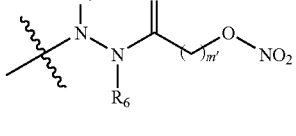
(51) 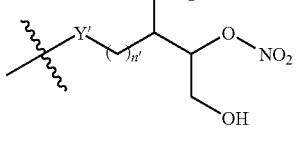
(52) 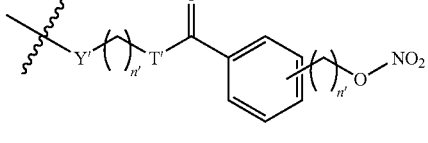
(53) 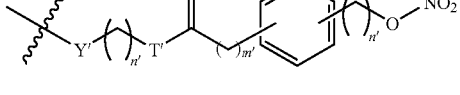

wherein:
Y' is oxygen or sulfur;
T' is oxygen, sulfur or $NR_6$;
$X_5$ is oxygen, $(S(O)_o)_o$ or $NR_6$;
$R_6$ is a hydrogen, a lower alkyl group, an aryl group;
$R_7$ is a lower alkyl group or an aryl group;
$R_8$ at each occurrence is independently is a hydrogen, a hydroxyl group, a lower alkyl group, an aryl group, $-NO_2$, $-CH_2-ONO_2$ or $-CH_2-OH$;
n' and m' are each independently an integer from 0 to 10;
o is as defined herein; and
with the proviso for Formula 8 for X:
Y' and $X_5$ cannot be oxygen; and
when Y' is oxygen and $X_5$ is $-N(CH_3)$, then n' and m' must be any integer except 1.

In more preferred embodiments the compounds of Formulas (I) are:
2-(2-(nitrooxy)ethylthio)ethyl(2S)-2-(6-methoxy(2-naphthyl))propanoate;
2-((2-(nitrooxy)ethyl)sulfonyl)ethyl(2S)-2-(6-methoxy(2-naphthyl))propanoate;
2-((2-(nitrooxy)ethyl)sulfinyl)ethyl(2S)-2-(6-methoxy(2-naphthyl))propanoate;
2-((2-(nitrooxy)ethyl)4-nitrophenyl)amino)ethyl 2-(6-methoxy-2-naphthyl)propanoate;
2R)-2,3-bis(nitrooxy)propyl(2S)-2-(6-methoxy(2-naphthyl)propanoate;
(2R)-7-(nitrooxy)-4,8-dioxabicyclo(3.3.0)oct-2-yl(2S)-2-(6-methoxy(2-naphthyl))propanoate;
phosphonomethyl(2S)-2-(6-methoxy(2-naphthyl))propanoate 3-(nitrooxy)propylamine nitric acid salt;
phosphonomethyl(2S)-2-(6-methoxy(2-naphthyl))propanoate 4-nitro-1-(nitrooxy)-2-((nitrooxy)methyl)but-2-ylamine salt;
(5-((nitrooxy)methyl-1,3-dioxan-5-yl)methyl(2S)-2-(6-methoxy(2-naphthyl))-propanoate;
2,2-bis(nitrooxy)propyl(2S)-2-(6-methoxy(2-naphthyl))propanoate;
3-(4-((nitrooxy)methyl)phenylcarbonyloxy)-2-oxopropyl (2S)-2-(6-methoxy(2-naphthyl))propanoate;
2-methyl-2-nitro-3-(nitrooxy)propyl(2S)-2-(6-methoxy(2-naphthyl))propanoate;
2-nitro-3-(nitrooxy)-2-((nitrooxy)methyl)propyl(2S)-2-(6-methoxy(2-naphthyl))propanoate;
2-(N-(2-(nitrooxy)ethyl)carbamoyloxy)ethyl(2S)-2-(6-methoxy(2-naphthyl))propanoate;
3-(2-(nitrooxy)ethoxy)phenyl(2S)-2-(6-methoxy(2-naphthyl)propanoate;
4-(2-(nitrooxy)ethoxy)phenyl(2S)-2-(6-methoxy(2-naphthyl))propanoate;
(N-methyl-N-(2-(nitrooxy)ethyl)carbamoyl)methyl(2S)-2-(6-methoxy(2-naphthyl))propanoate;
(N-ethyl-N-(2-(nitrooxy)ethyl)carbamoyl)methyl(2S)-2-(6-methoxy(2-naphthyl))propanoate;
2-(4-((nitrooxy)methyl)piperidyl)-2-oxoethyl(2S)-2-(6-methoxy(2-naphthyl))propanoate;
(N-methyl-N-(((2-(nitrooxy)ethyl)oxycarbonyl)methyl)carbamoyl)methyl(2S)-2-(6-methoxy(2-naphthyl))propanoate;
(N-methyl-N-(((3-(nitrooxy)propyl)oxycarbonyl)methyl)carbamoyl)methyl(2S)-2-(6-methoxy(2-naphthyl))propanoate;
(N-methyl-N-((N-(2-(nitrooxy)ethyl)carbamoyl)methyl)carbamoyl)methyl(2S)-2-(6-methoxy(2-naphthyl))propanoate;
((2-(nitrooxy)ethyl)oxycarbonyl)methyl 2-(6-methoxy-2-naphthyl)propanoate;
(N-(3-(nitrooxy)propyl)carbamoyl)methyl 2-(6-methoxy-2-naphthyl)propanoate;
((2-((2-(nitrooxy)ethyl)sulfonyl)ethyl)oxycarbonyl)methyl 2-(6-methoxy-2-naphthyl)propanoate;
1S,5S,2R,6R)-6-(nitrooxy)-4,8-dioxabicyclo(3.3.0)oct-2-yl) oxycarbonyl)methyl(2S)-2-(6-methoxy(2-naphthyl))propanoate;
(2S)-2,3-bis(nitrooxy)propyl(2S)-2-(6-methoxy-5-nitro(2-naphthyl))propanoate;
2S)-2-hydroxy-3-(nitrooxy)propyl(2S)-2-(6-methoxy(2-naphthyl))propanoate;
(2R)-2-hydroxy-3-(nitrooxy)propyl(2S)-2-(6-methoxy(2-naphthyl))propanoate;
(2S)-2-(6-methoxy(2-naphthyl))-N4N-(2-(nitrooxy)ethyl) carbamoyl)methoxy)propanamide;
3-(2-(4-((nitrooxy)methyl)phenyl)acetyloxy)-2-oxopropyl (2S)-2-(6-methoxy(2-naphthyl))propanoate;
2-(4-(2-(nitrooxy)ethyl)piperidyl)-2-oxoethyl(2S)-2-(6-methoxy(2-naphthyl))propanoate;
4-((2-(nitrooxy)ethyl)oxycarbonyl)phenyl(2S)-2-(6-methoxy(2-naphthyl))propanoate;
2-((2-(nitrooxy)ethyl)oxycarbonyl)phenyl(2S)-2-(6-methoxy(2-naphthyl))propanoate;
(N-methyl-N-(3-(nitrooxy)propyl)carbamoyl)methyl(2S)-2-(6-methoxy(2-naphthyl))propanoate;
(2S)-2-(6-methoxy(2-naphthyl))-N-(2-(4-((nitrooxy)methyl)piperidyl)-2-oxoethoxy)propanamide;
3-((2-(nitrooxy)ethyl)oxycarbonyl)phenyl(2S)-2-(6-methoxy(2-naphthyl)propanoate;
2-(4-(2-(nitrooxy)ethyl)piperazinyl)-2-oxoethyl(2S)-2-(6-methoxy(2-naphthyl))propanoate hydrogen chloride;
3-((2S)-2-(6-methoxy(2-naphthyl)propanoyloxy)-2-methyl-2-((nitrooxy)methyl)propyl(2S)-2-(6-methoxy(2-naphthyl)propanoate;
2-(4-(2-(nitrooxy)ethoxy)phenoxy)ethyl(2S)-2-(6-methoxy (2-naphthyl))propanoate;
2-((2S)-2-(6-methoxy(2-naphthyl))propanoyloxy)ethyl 3-(nitrooxy)-propyl ethane-1,2-dioate;
N-((2S)-2-(6-methoxy(2-naphthyl))propanoylamino)-4 (nitrooxy)butanamide;
4-((2S)-2-(6-methoxy(2-naphthyl))propanoyloxy)(2S,3S)-2,3-bis(nitrooxy)butyl(2S)-2-(6-methoxy(2-naphthyl)) propanoate
(2S,3S)-2,3-bis(nitrooxy)-4-hydroxybutyl(2S)-2-(6-methoxy(2-naphthyl))propanoate;
2-((3-((nitrooxy)methyl)phenyl)carbonylamino)ethyl(2S)-2-(6-methoxy(2-napthyl propanoate;
(2R)-2-(nitrooxy)-3-(phenylmethoxy)propyl(2S)-2-(6-methoxy(2-naphthyl))propanoate;
2-(N-methyl(4-((nitrooxy)methyl)phenyl)carbonylamino) ethyl(2S)-2-(6-methoxy(2-naphthyl))propanoate;
(1S,2S,5S,6R)-6-(nitrooxy)-4,8-dioxabicyclo(3.3.0)oct-2-yl 2-(1-((4-chlorophenyl)carbonyl)-5-methoxy-2-methylindol-3-yl)acetate;
(1S,2S,5S,6R)-6-(nitrooxy)-4,8-dioxabicyclo(3.3.0)oct-2-yl 2-(2-((2,6-dichlorophenyl)amino)phenyl)acetate;
2-(((4-methylphenyl)sulfonyl)(2-(nitrooxy)ethyl)amino) ethyl(2S)-2-(6-methoxy(2-naphthyl))propanoate;
2-(N-methyl-2-(4-((nitrooxy)methyl)phenyl)acetylamino) ethyl(2S)-2-(6-methoxy(2-naphthyl))propanoate;
(2R)-2,3-bis(nitrooxy)propyl 2-(1-((4-chlorophenyl)carbonyl)-5-methoxy-2-methylindol-3-yl)acetate;
(2S)-2,3-bis(nitrooxy)propyl 2-(1-((4-chlorophenyl)carbonyl)-5-methoxy-2-methylindol-3-yl)acetate;
(2S)-2,3-bis(nitrooxy)propyl 2-(2-((2,6-dichlorophenyl) amino)phenyl)acetate;

(2R)-2,3-bis(nitrooxy)propyl 2-(2-((2,6-dichlorophenyl)amino)phenyl)acetate;

(2S)-2-(6-methoxy(2-naphthyl))-1-(4-(nitrooxy)butylthio)propan-1-one;

(N-methyl-N-(2-(nitrooxy)ethyl)carbamoyl)methyl 2-(1-((4-chlorophenyl)carbonyl)-5-methoxy-2-methylindol-3-yl)acetate;

(N-(2-(nitrooxy)ethyl)carbamoyl)methyl 2-(1-((4-chlorophenyl)carbonyl)-5-methoxy-2-methylindol-3-yl)acetate;

(N-(2-(nitrooxy)ethyl)carbamoyl)methyl 2-(2-((2,6-dichlorophenyl)amino)phenyl)acetate; and pharmaceutically acceptable salts thereof.

Another embodiment of the invention describes the metabolites of the compounds of Formulas (I), (II) and pharmaceutically acceptable salts thereof. These metabolites, include but are not limited to, the non-nitrosated derivatives, degradation products, hydrolysis products, and the like, of the compounds of Formulas (I), (II) and pharmaceutically acceptable salts thereof.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The NSAIDs of the invention can be nitrosated through one or more sites such as oxygen, sulfur and/or nitrogen using the methods described in the examples herein and using conventional methods known to one skilled in the art. For example, known methods for nitrosating compounds are described in U.S. Pat. Nos. 5,380,758, 5,859,053, 5,703,073 and 6,297,260; and in WO 94/03421, WO 94/04484, WO 94/12463, WO 95/09831, WO 95/30641, WO 97/27749, WO 98/19672, WO 01/00563, WO 00/51988, WO 00/72838, WO 01/04082, WO 01/10814, WO 01/45703, WO 02/11707, WO 02/30866 and Oae et al, *Org. Prep. Proc. Int.*, 15(3):165-198 (1983), the disclosures of each of which are incorporated by reference herein in their entirety. The methods of nitrosating the compounds described in the examples herein and in these references can be applied by one skilled in the art to produce any of the nitrosated NSAIDs described herein.

The compounds of the invention include the NSAIDs that have been nitrosated through one or more sites such as oxygen (hydroxyl condensation), sulfur (sulfhydryl condensation) and/or nitrogen. The nitrosated NSAIDs of the invention donate, transfer or release a biologically active form of nitrogen monoxide (i.e., nitric oxide).

Nitrogen monoxide can exist in three forms: NO− (nitroxyl), NO• (uncharged nitric oxide) and NO+ (nitrosonium). NO• is a highly reactive short-lived species that is potentially toxic to cells. This is critical because the pharmacological efficacy of NO depends upon the form in which it is delivered. In contrast to the nitric oxide radical (NO•), nitrosonium (NO+) does not react with $O_2$ or $O_2^-$ species, and functionalities capable of transferring and/or releasing NO+ and NO− are also resistant to decomposition in the presence of many redox metals. Consequently, administration of charged NO equivalents (positive and/or negative) is a more effective means of delivering a biologically active NO to the desired site of action.

Compounds contemplated for use in the invention (e.g., NSAIDs that are nitrosated), are, optionally, used in combination with nitric oxide and compounds that release nitric oxide or otherwise directly or indirectly deliver or transfer a biologically active form of nitrogen monoxide to a site of its intended activity, such as on a cell membrane in vivo.

The term "nitric oxide" encompasses uncharged nitric oxide (NO•) and charged nitrogen monoxide species, preferably charged nitrogen monoxide species, such as nitrosonium ion (NO+) and nitroxyl ion (NO−). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z,3E)-4-ethyl-2-(hydroxyimino)-6-methyl-5-nitro-3-heptenyl)-3-pyridinecarboxamide (FR 146801), nitrosoamines, furoxans as well as substrates for the endogenous enzymes which synthesize nitric oxide. NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino)diazen-1-ium-1,2-diolate (spermine NONOate or "SPER/NO") and sodium(Z)-1-(N,N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of each of which are incorporated by reference herein in their entirety.

The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, Org. Prep. Proc. Int., 15(3): 165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; or (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, an arylsulfonyloxy, a urea, a nitro, -T-Q-, or $—(C(R_g)(R_h))_k$-T-Q or $R_e$ and $R_f$ taken together are an oxo, a thial, a heterocyclic ring, a cycloalkyl group, an oxime, a hydrazone or a bridged cycloalkyl group; Q is —NO or —$NO_2$; and T is independently a covalent bond, a carbonyl, an oxygen, —$S(O)_o$— or —$N(R_a)R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylsulfinyl, an alkylsulfonyl, an alkylsulfonyloxy, an arylsulfinyl, an arylsulfonyloxy, an arylsulfonyl, a sulfonamido, a carboxamido, a carboxylic ester, an aminoalkyl, an aminoaryl, —$CH_2$—C(T-Q)($R_g$)($R_h$), or —($N_2O_2$—)$^-$•$M^+$, wherein $M^+$ is an organic or inorganic cation; with the proviso that when $R_i$ is —$CH_2$—C(T-Q)($R_g$)($R_h$) or —($N_2O_2$—)•$M^+$; then "-T-Q" can be a hydrogen, an alkyl group, an alkoxyalkyl group, an aminoalkyl group, a hydroxy group or an aryl group; and $R_g$ and $R_h$ at each occurrence are independently $R_e$;

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N-polypeptides (the term "polypeptide" includes proteins and polyamino acids that do not possess an ascertained biological function, and derivatives thereof); ON—O— or ON—N-amino acids (including natural and synthetic amino acids and their stereoisomers and racemic mixtures); ON—O— or ON—N-sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C-heterocyclic compounds.

Another group of NO adducts for use in the invention include nitrates that donate, transfer or release nitric oxide, such as compounds comprising at least one $O_2N$—O—, $O_2N$—N— or $O_2N$—S— group. Preferred among these compounds are $O_2N$—O—, $O_2N$—N— or $O_2N$—S-polypeptides (the term "polypeptide" includes proteins and also polyamino acids that do not possess an ascertained biological function, and derivatives thereof); $O_2N$—O—, $O_2N$—N— or $O_2N$—S-amino acids (including natural and synthetic amino acids and their stereoisomers and racemic mixtures); $O_2N$—O—, $O_2N$—N— or $O_2N$—S— sugars; $O_2N$—O—, $O_2N$—N— or $O_2N$—S— modified and unmodified oligonucleotides (comprising at least 5 nucleotides, preferably 5-200 nucleotides); $O_2N$—O—, $O_2N$—N— or $O_2N$—S— straight or branched, saturated or unsaturated, aliphatic or aromatic, substituted or unsubstituted hydrocarbons; and $O_2N$—O—, $O_2N$—N— or $O_2N$—S— heterocyclic compounds. Preferred examples of compounds comprising at least one $O_2N$—O—, $O_2N$—N— or $O_2N$—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284, 872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1''}R^{2''}N—N(O-M^+)—NO$, where $R^{1''}$ and $R^{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M^+$ is an organic or inorganic cation, such as, for example, an alkyl substituted ammonium cation or a Group I metal cation.

The invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature,* 327:524-526 (1987); Ignarro et al, *Proc. Natl. Acad. Sci. USA,* 84:9265-9269 (1987)).

The invention is also based on the discovery that compounds and compositions of the invention may be used in conjunction with other therapeutic agents for co-therapies, partially or completely, in place of other conventional antiinflammatory compounds, such as, for example, together with steroids, COX-2 inhibitors, NSAIDs, 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG-CoA inhibitors, $H_2$ receptor antagonists, antineoplastic agents, antiplatelet agents, thrombin inhibitors, thromboxane inhibitors, decongestants, diuretics, sedating or non-sedating anti-histamines, inducible nitric oxide synthase inhibitors, opiods, analgesics, *Helicobacter pylori* inhibitors, proton pump inhibitors, isoprostane inhibitors, and mixtures of two or more thereof.

Leukotriene $A_4$ ($LTA_4$) hydrolase inhibitors refer to compounds that selectively inhibit leukotriene $A_4$ hydrolase with an $IC_{50}$ of less than about 10 µM, and preferably with an $IC_{50}$ of less than about 1 µM. Suitable $LTA_4$ hydrolase inhibitors include, but are not limited to, RP-64966, (S,S)-3-amino-4-(4-benzyloxyphenyl)-2-hydroxybutyric acid benzyl ester, N-(2(R)-(cyclohexylmethyl)-3-(hydroxycarbamoyl)propionyl)-L-alanine, 7-(4-(4-ureidobenzyl)phenyl) heptanoic acid and 3 (3-(1E,3E-tetradecadienyl)-2-oxiranyl)benzoic acid lithium salt, and mixtures of two or more thereof.

Suitable $LTB_4$ receptor antagonists include, but are not limited to, ebselen, linazolast, ontazolast; WAY 121006; Bay-x-1005; BI-RM-270; CGS-25019C; ETH-615; MAFP; TMK-688; T-0757; LY 213024, LY 210073, LY 223982, LY 233469, LY 255283, LY 264086, LY 292728 and LY 293111; ONO-LB457, ONO-4057, and ONO-LB-448, S-2474, calcitrol; PF 10042; Pfizer 105696; RP 66153; SC-53228, SC-41930, SC-50605, SC-51146 and SC-53228; SB-201146 and SB-209247; SKF-104493; SM 15178; TMK-688; BPC 15, and mixtures of two or more thereof. The preferred $LTB_4$ receptor antagonists are calcitrol, ebselen, Bay-x-1005, CGS-25019C, ETH-615, LY-293111, ONO-4057 and TMK-688, and mixtures of two or more thereof.

Suitable 5-LO inhibitors include, but are not limited to, A-76745, 78773 and ABT761; Bay-x-1005; CMI-392; E-3040; EF-40; F-1322; ML-3000; PF-5901; R-840; rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast, and mixtures of two or more thereof. Suitable 5-LO inhibitors are also described more fully in WO 97/29776, the disclosure of which is incorporated herein by reference in its entirety.

Suitable 5-HT agonists, include, but are not limited to, rizatriptan, sumatriptan, naratriptan, zolmitroptan, eleptriptan, almotriptan, ergot alkaloids. ALX 1323, Merck L 741604 SB 220453 and LAS 31416. Suitable 5-HT agonists are described more fully in WO 0025779, and in WO 00/48583. 5-HT agonists refers to a compound that is an agonist to any 5-HT receptor, including but not limited to, $5-HT_1$ agonists, $5-HT_{1B}$ agonists and $5-HT_{1D}$ agonists, and the like.

Suitable steroids, include, but are not limited to, budesonide, dexamethasone, corticosterone, prednisolone, and the like. Suitable steroids are described more fully in the literature, such as in the Merck Index on CD-ROM, $13^{th}$ Edition.

Suitable HMG CoA inhibitors, include, but are not limited to, reductase and synthase inhibitors, such as, for example, squalene synthetase inhibitors, benzodiazepine squalene synthase inhibitors, squalene epoxidase inhibitors, acyl-coenzyme A, bile acid sequestrants, cholesterol absorption inhibitors, and the like. Suitable HMG CoA inhibitors include simvastatin, pravastatin, lovastatin, mevastatin, fluvastatin, atorvastatin, cerivastatin, and the like, and are described more fully in U.S. Pat. No. 6,245,797 and WO 99/20110, the disclosures of each of which are incorporated by reference herein in their entirety.

Suitable COX-2 inhibitors, include, but are not limited to, NS-386, nimesulide, flosulide, celecoxib, rofecoxib, COX-189, etoracoxib, Bextra, Dynastat, Arcoxia, SC-57666, DuP 697, SC-58125, SC-58635, and the like. Suitable COX-2 inhibitors are in U.S. Pat. Nos. 5,344,991, 5,380,738, 5,393, 790, 5,409,944, 5,434,178, 5,436,265, 5,466,823, 5,474,995, 5,510,368, 5,536,752, 5,550,142, 5,552,422, 5,604,253, 5,604,260, and 5,639,780 and in WO 94/03387, WO 94/15723, WO 94/20480, WO 94/26731, WO 94/27980, WO 95/00501, WO 95/15316, WO 96/03387, WO 96/03388, WO 96/06840, WO 96/21667, WO 96/31509, WO 96/36623, WO 97/14691, WO 97/16435, WO 01/45703 and WO 01/87343; the disclosures of which are incorporated herein by reference in their entirety.

Suitable NSAIDs, include, but are not limited to, acetaminophen, aspirin, diclofenac, ibuprofen, ketoprofen, naproxen, indomethacin, including but not limited to prodrugs thereof, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, $13^{th}$ Edition; and in U.S. Pat. Nos. 6,057,347 and 6,297,260 assigned to NitroMed. Inc., the disclosures of which are incorporated herein by reference in their entirety.

Suitable $H_2$ receptor anatgonists, include, but are not limited to, cimetidine, roxatidine, rantidine and the like. Suitable $H_2$ receptor antagonists are described more fully in the literature, such as in Goodman and Gilman, The Pharmacological Basis of Therapeutics (9th Edition), McGraw-Hill, 1995, Pgs. 901-915; the Merck Index on CD-ROM, 13th Edition; and in WO 00/28988 assigned to NitroMed. Inc., the disclosures of which are incorporated herein by reference in their entirety.

Suitable antineoplastic agents, include but are not limited to, 5-FU-fibrinogen, acanthifolic acid, aminothiadiazole, altretamine, anaxirone, aclarubicin and the like. Suitable antineoplastic agents are also described in U.S. Pat. No. 6,025, 353 and WO 00/38730, the disclosures of which are incorporated herein by reference in their entirety.

Suitable antiplatelet agents, include but are not limited to, aspirin, ticlopidine, dipyridamole, clopidogrel, glycoprotein IIb/IIIa receptor antagonists, and the like. Suitable antineoplastic agents are also described in WO 99/45913, the disclosure of which is incorporated herein by reference in its entirety. In a preferred embodiment of the invention, the antiplatelet agent is aspirin, more preferably, low-dose aspirin (i.e. 75 mg-100 mg/day).

Suitable thrombin inhibitors, include but are not limited to, N'-((1-(aminoiminomethyl)-4-piperidinyl)methyl)-N-(3,3-diphenylpropinyl)-L-proline amide), 3-(2-phenylethylamino)-6-methyl-1-(2-amino-6-methyl-5-methylene-carboxamidomethylpyridinyl)-2-pyrazinone, 3-(2-phenethylamino)-6-methyl-1-(2-amino-6-methyl-5-methylenecarboxamidomethylpyridinyl)-2-pyridinone, and the like. Suitable thrombin inhibitors are also described in WO 00/18352, the disclosure of which is incorporated herein by reference in its entirety.

Suitable thromboxane inhibitors, include but are not limited to thromboxane synthase inhibitors, thromboxane receptor antagonists, and the like. Suitable thromboxane inhibitors, are also described in WO 01/87343, the disclosure of which is incorporated herein by reference in its entirety.

Suitable decongestants include, but are not limited to, phenylephrine, phenylpropanolamine, pseudophedrine, oxymetazoline, ephinephrine, naphazoline, xylometazoline, propylhexedrine, levo-desoxyephedrine, and the like.

Suitable antitussives include, but are not limited to, codeine, hydrocodone, caramiphen, carbetapentane, dextramethorphan, and the like.

Suitable proton pump inhibitors, include, but are not limited to, omeprazole, esomeprazole, lansoprazole, rabeprazole, pantoprazole, and the like. Suitable proton pump inhibitors are described more fully in the literature, such as in Goodman and Gilman, The Pharmacological Basis of Therapeutics (9th Edition), McGraw-Hill, 1995, Pgs. 901-915; the Merck Index on CD-ROM, 13th Edition; and in WO 00/50037 assigned to NitroMed. Inc., the disclosures of which are incorporated herein by reference in their entirety.

The compounds and compositions of the invention, may also be used in combination therapies with opioids and other analgesics, including, but not limited to, narcotic analgesics, Mu receptor antagonists, Kappa receptor antagonists, non-narcotic (i.e. non-addictive) analgesics, monoamine uptake inhibitors, adenosine regulating agents, cannabinoid derivatives, neurokinin 1 receptor antagonists, Substance P antagonists, neurokinin-1 receptor antagonists, sodium channel blockers, N-methyl-D-aspartate receptor antagonists, and mixtures of two or more thereof. Preferred combination therapies would be with morphine, meperidine, codeine, pentazocine, buprenorphine, butorphanol, dezocine, meptazinol, hydrocodone, oxycodone, methadone, Tramadol ((+) enantiomer), DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol ((−) enantiomer), GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, CP-99,994, and mixtures of two or more thereof.

The compounds and compositions of the invention can also be used in combination with inducible nitric oxide synthase (iNOS) inhibitors. Suitable iNOS inhibitors are disclosed in U.S. Pat. Nos. 5,132,453 and 5,273,875, and in WO 97/38977 and WO 99/18960, the disclosures of each of which are incorporated by reference herein in their entirety.

The invention is also based on the discovery that the administration of a therapeutically effective amount of the compounds and compositions described herein is effective for treating inflammation, pain (both chronic and acute), and fever, such as, for example, analgesic in the treatment of pain, including, but not limited to headaches, migraines, postoperative pain, dental pain, muscular pain, and pain resulting from cancer; as an antipyretic for the treatment of fever, including but not limited to, rheumatic fever, symptoms associated with influenza or other viral infections, common cold, low back and neck pain, dysmenorrhea, headache, toothache, sprains, strains, myositis, neuralgia, synovitis, menstrual cramps; arthritis, including but not limited to rheumatoid arthritis, degenerative joint disease (osteoarthritis), spondyloarthropathies, gouty arthritis, systemic lupus erythematosus and juvenile arthritis. For example, the patient can be administered a therapeutically effective amount of least one nitrosated NSAID. In another embodiment, the patient can be administered a therapeutically effective amount of at least one nitrosated NSAID, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated NSAID, and, at least one therapeutic agent, including but not limited to, steroids, cyclooxygenase-2 (COX-2) inhibitors, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Another embodiment of the invention provides methods for treating gastrointestinal disorders by administering to the patient in need thereof a therapeutically effective amount of the compounds and/or compositions described herein. Such gastrointestinal disorders refer to any disease or disorder of the upper gastrointestinal tract (e.g., esophagus, the stomach, the duodenum, jejunum) including, for example, inflammatory bowel disease, Crohn's disease, gastritis, irritable bowel syndrome, constipation, ulcerative colitis, peptic ulcers, stress ulcers, gastric hyperacidity, dyspepsia, gastroparesis, Zollinger-Ellison syndrome, gastroesophageal reflux disease, bacterial infections (including, for example, a *Helicobacter Pylori* associated disease), short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns. For example, the patient can be administered a therapeutically effective amount of least one nitrosated NSAID of the invention. In another embodiment, the patient can be administered a therapeutically effective amount of at least one nitrosated NSAID, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated NSAID, and, at least one therapeutic agent, including but not limited to, steroids, cyclooxygenase-2 (COX-2) inhibitors, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Yet another embodiment of the invention provides methods facilitating wound healing (such as, for example, ulcer healing, bone healing including osteoporosis) by administering to the patient in need thereof a therapeutically effective amount of the compounds and/or compositions described herein. Wound refers to, and includes, any lesion that is characterized by loss of tissue, and, includes, but is not limited to, ulcers, cuts, burns, bone fractures, orthopedic procedure, wound infliction, and the like. Ulcers refers to lesions of the upper gastrointestinal tract lining that are characterized by loss of tissue, and, include, but are not limited to, gastric ulcers, duodenal ulcers, gastritis, and the like. For example, the patient can be administered a therapeutically effective amount of least one nitrosated NSAID of the invention. In another embodiment, the patient can be administered a therapeutically effective amount of at least one nitrosated NSAID and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated NSAID and at least one therapeutic agent, including but not limited to, steroids, cyclooxygenase-2 (COX-2) inhibitors, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Another embodiment of the invention provides methods for decreasing and/or reversing gastrointestinal, renal, respiratory and other toxicity (such as, for example, kidney toxicity) resulting from the use of drugs, such as, nonsteroidal anti-inflammatory drugs and/or cyclooxygenase-2 (COX-2) inhibitors by administering to a patient in need thereof a therapeutically effective amount of the compounds and/or compositions described herein. For example, the patient can be administered a therapeutically effective amount of at least one nitrosated NSAID of the invention. In another embodiment, the patient can be administered a therapeutically effective amount of at least one nitrosated NSAID and at least one nitric oxide donor. In yet another embodiment, the patient can be administered a therapeutically effective amount of at least one nitrosated NSAID and at least one therapeutic agent, and, optionally, at least one nitric oxide donor. The compounds can be administered separately or in the form of a composition.

Another embodiment of the invention provides for treating inflammatory disease states and disorders by administering to a patient in need thereof a therapeutically effective amount of the compounds and/or compositions described herein. Such inflammatory disease states and/or disorders include, for example, cardiovascular disorder, reperfusion injury to an ischemic organ, angiogenisis, arthritis, including but not limited to rheumatoid arthritis, degenerative joint disease (osteoarthritis), spondyloarthropathies, gouty arthritis, systemic lupus erythematosus and juvenile arthritis; asthma, bronchitis, premature labor, tendinitis, bursitis; autoimmune diseases, immunological disorders; skin-related conditions, such as, for example, psoriasis, eczema, surface wounds, burns and dermatitis; post-operative inflammation including from ophthalmic surgery, such as, for example, cataract surgery and refractive surgery, and the like; neoplasia, such as, for example, brain cancer, bone cancer, epithelial cell-derived neoplasia (epithelial carcinoma), such as, for example, basal cell carcinoma, adenocarcinoma, gastrointestinal cancer, such as, for example, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body, benign and cancerous tumors, growths, polyps, adenomatous polyps, including, but not limited to, familial adenomatous polyposis, fibrosis resulting from radiation therapy, and the like; inflammatory processes in diseases, such as, for example, vascular diseases, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like; pulmonary inflammation, such as, for example, those associated with viral infections and cystic fibrosis, and the like; central nervous system disorders, such as, for example, cortical dementia including Alzheimer's disease, vascular dementia, multi-infarct dementia, pre-senile dementia, alcoholic dementia, senile dementia, memory loss and central nervous system damage resulting from stroke, ischemia and trauma, and the like; allergic rhinitis, respiratory distress syndrome, endotoxin shock syndrome, inflammations and/or microbial infections including, for example, inflammations and/or infections of the eyes, ears, nose, throat, and/or skin; bacterial-induced inflammation, such as, for example, *Chlamydia*-induced inflammation; viral induced inflammation, urinary and/or urological disorders, such as, for example, incontinence and the like; endothelial dysfunctions, such as, for example, diseases accompanying these dysfunctions, endothelial damage from hypercholesterolemia, endothelial damage from hypoxia, endothelial damage from mechanical and chemical noxae, especially during and after drug, and mechanical reopening of stenosed vessels, for example, following percutaneous transluminal angiography (PTA) and percutaneous transluminal coronary angiography (PTCA), endothelial damage in postinfarction phase, endothelium-mediated reocculusion following bypass surgery, blood supply disturbances in peripheral arteries, and the like; sexual dysfunction; tissue deterioration, such as, for example, for organ transplant rejection, and the like; disorders treated by the inhibition and/or prevention of activation, adhesion and infiltration of neutrophils at the site of inflammation; and disorders treated by the inhibition and/or prevention of platelet aggregation. The compounds and compositions of the invention can also be used as a pre-anesthetic medication in emergency operations to reduce the danger of aspiration of acidic gastric contents. For example, the patient can be administered a therapeutically effective amount of least one nitrosated NSAID. In another embodiment, the patient can be administered a therapeutically effective amount of at least one nitrosated NSAID and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one nitrosated NSAID, and, at least one therapeutic agent, including but not limited to, steroids, cyclooxygenase-2 (COX-2) inhibitors, nonsteroidal antiinflammatory compounds (NSAID), 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, HMG CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and, optionally, at least one compound that donates, transfers or releases nitric oxide, or elevates levels of endogenous EDRF or nitric oxide, or is a substrate for nitric oxide synthase. The compounds can be administered separately or in the form of a composition.

Another embodiment of the invention provides methods for treating and/or preventing ophthalmic diseases and disorders by administering to a patient in need thereof a therapeutically effective amount of the compounds and/or compositions described herein. For example, the patient can be administered a therapeutically effective amount of at least one nitrosated NSAID. In another embodiment, the patient can be administered a therapeutically effective amount of at least one nitrosated NSAID and at least one nitric oxide donor. In yet another embodiment, the patient can be administered a therapeutically effective amount of at least one nitrosated NSAID and at least one therapeutic agent, and, optionally, at least one nitric oxide donor. The compounds can be administered separately or in the form of a composition. Such ophthalmic diseases and disorders include, for example, retinitis, retinopathies, uveitis, ocular photophobia, acute injury to the eye tissue, glaucoma, inflammation of the eye and elevation of intraocular pressure and the like.

When administered separately, the nitrosated NSAID can be administered about the same time as part of the overall treatment regimen i.e., as a combination therapy. "About the same time" includes administering the nitrosated NSAID, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one nitrosated NSAID and/or at least one nitric oxide donor and/or therapeutic agent, they can also be used in combination with one or more additional compounds which are known to be effective against the specific disease state targeted for treatment. The nitric oxide donors, therapeutic agents and/or other additional compounds can be administered simultaneously with, subsequently to, or prior to administration of the nitrosated NSAID.

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, semi-solid fats, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as, for example, phospholipids and/or at least one or more surfactants, and, optionally cosurfactants, as disclosed in, for example, WO 01/66088 and WO 03/022249, the disclosures of each of which are incorporated by reference herein in their entirety.

Suitable natural or synthetic phospholipids include, but are not limited to, non-ionic surfactants containing a hydrogenated or non-hydrogenated phosphatidyl choline, a diglyceride linked to a choline wster of phosphoric acid, such as for example, lecithin, obtained from any source including soya or eggs, or a mixture thereof.

Suitable surfactants include, but are not limited to, surface-active amphiphilic compounds, such as, for example, block co-polymers; non-ionic surfactants, such as, poloxamers, such as, for example, Poloxamer 407, Poloxamer 401, Poloxamer 338, Poloxamer 331, Poloxamer 231, and the like; tetrafunctional polyoxyethylene polyoxypropylene block copolymers of ethylene diamane, such as, for example, Poloxamine 908, Poloxamine 1307, and the like; polyoxyethylene polyoxybutylene block copolymers, such as, for example Polyglycol BM45, and the like.

The preferred methods of administration of the NSAIDs and compositions for the treatment of gastrointestinal disorders are orally, bucally or by inhalation. The preferred methods of administration for the treatment of inflammation and microbial infections are orally, bucally, topically, transdermally or by inhalation.

The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given nitrosated NSAID which will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the NSAID. The usual daily doses of NSAIDs are about 3 to about 40 mg/kg of body weight and the doses of nitric oxide donors in the pharmaceutical composition can be in amounts of about 1 to about 500 mg/kg of body weight daily, preferably about 1 to about 50 mg/kg of body weight daily. Effective doses may be extrapolated from dose-response curves derived from in vitro or animal model test systems and are in the same ranges or less than as described for the commercially available compounds in the Physician's Desk Reference, supra.

The amount of nitric oxide donor in a pharmaceutical composition can be in amounts of about 0.1 to about 10 times the molar equivalent of the NSAID. The usual daily doses of NSAIDs are about 3 to about 40 mg/kg of body weight and the doses of nitric oxide donors in the pharmaceutical composition can be in amounts of about 1 to about 500 mg/kg of body weight daily, preferably about 1 to about 50 mg/kg of body weight daily. The compounds may be administered on a regimen of up to 6 times per day, preferably 1 to 4 times per day, and most preferably twice per day. Effective doses may be extrapolated from dose-response curves derived from in vitro or animal model test systems and are in the same ranges or less than as described for the commercially available compounds in the Physician's Desk Reference, supra.

The invention also provides pharmaceutical kits comprising one or more containers filled with one or more of the ingredients of the pharmaceutical compounds and/or compositions of the invention, including, at least, one or more of the novel nitrosated NSAID, and one or more of the NO donors described herein. Associated with such kits can be additional therapeutic agents or compositions (e.g., steroids, COX-2 inhibitors, nonsteroidal antiinflammatory compounds (NSAID), 5-lipoxygenase (5-LO) inhibitors, leukotriene $B_4$ ($LTB_4$) receptor antagonists and leukotriene $A_4$ ($LTA_4$) hydrolase inhibitors, 5-HT agonists, HMG-CoA inhibitors, $H_2$ antagonists, antineoplastic agents, antiplatelet agents, thrombin inhibitors, thromboxane inhibitors, decongestants, diuretics, sedating or non-sedating anti-histamines, inducible nitric oxide synthase inhibitors, opioids, analgesics, *Helicobacter pylori* inhibitors, proton pump inhibitors, isoprostane inhibitors, and the like), devices for administering the compositions, and notices in the form prescribed by a governmental agency regulating the manufacture, use or sale of pharmaceuticals or biological products which reflects approval by the agency of manufacture, use or sale for humans.

EXAMPLES

The following non-limiting examples further describe and enable one of ordinary skill in the art to make and use the present invention. In each of the examples, flash chromatography was performed on 40 micron silica gel (Baker).

Example 1

2-(2-(Nitrooxy)ethylthio)ethyl(2S)-2-(6-methoxy(2-naphthyl))propanoate 1a. 2-(2-Hydroxyethylthio)ethyl(2S)-2-(6-methoxy (2-naphthyl))propanoate To a solution of (2S)-2-(6-methoxy(2-naphthyl))propanoic acid (naproxen, 15.0 g, 65 mmol), 2,2'-thiodiethanol (40 g, 325 mmol) and N,N-dimethylaminopyridine (DMAP, 1.59 g, 13 mmol) in dichloromethane (400 mL) at room temperature was added 1-(3-(dimethylamino) propyl)-3-ethylcarbodiimide hydrochloride (EDAC, 14.98 g, 78 mmol) as a solid, in portions. After stirring for 3 hours at room temperature, TLC analysis indicated the reaction was complete. The reaction mixture was partitioned between $CH_2Cl_2$ and water, and the water layer was washed with more $CH_2Cl_2$. The combined organic layer was washed with water, 0.1 N HCl, water, brine, and dried over magnesium sulfate. The solution was concentrated under vacuum, and the residue was purified via column chromatography, 5% ethyl acetate/dichloromethane. The appropriate fractions were combined, and the solvent evaporated. Trituration of the residue with ether/hexane gave the title compound as a white solid (17.72 g, 81% yield). Mp 58-61° C. $^1$H NMR (300 MHz, $CDCl_3$) δ 7.70 (d, J=8.6 Hz, 2H), 7.67 (d, J=0.9 Hz, 1H), 7.40 (dd, J=1.7, 8.5 Hz, 1H), 7.14 (dd, J=2.5, 8.8 Hz, 1H), 7.11 (d, J=2.5 Hz, 1H), 4.24 (t, J=6.7 Hz, 2H), 3.86 (q, J=7.2 Hz, 1H), 3.60 (app q, J=6.0 Hz, 2H), 2.69 (t, J=6.6 Hz, 2H), 2.61 (t, J=5.9 Hz, 2H), 2.00 (t, J=6.2 Hz, 1H), 1.59 (d, J=7.2 Hz, 3H). Mass spectrum (API-TIS) m/z 352 ($MNH_4^+$); Anal. calcd. for $C_{18}H_{22}O_4S$: C, 64.65; H, 6.63; S, 9.59. Found: C, 64.62; H, 6.59; S, 9.47.

1b. 2-(2-(Nitrooxy)ethylthio)ethyl(2S)-2-(6-methoxy (2-naphthyl))propanoate

To acetic anhydride (3.73 mL, 40.3 mmol) at 0° C. was added fuming nitric acid (90%, 1.25 mL, 26.9 mmol) with stirring. After the addition was complete, the reaction mixture was stirred at room temperature for 40 minutes, then added drop-wise to a solution of the product of Example 1a (6.0 g, 17.9 mmol) in ethyl acetate at 0° C. The reaction mixture was stirred at 0° C. for 3 hours, and then poured into a pre-cooled (0° C.) mixture of 75 mL of ethyl acetate and 100 mL of sodium bicarbonate. The mixture was stirred cold for 20 minutes, and then warmed to room temperature for 1 hour. The reaction mixture was partitioned between ethyl acetate and water, washed with sodium bicarbonate, water, and brine, and dried over sodium sulfate. The solvent was evaporated and the residue purified by column chromatography on silica, eluting with 25% ethyl acetate/hexane, to give the title compound as an oil, which slowly solidified (2.11 g, 5.56 mmol, 31% yield). Mp 33-37° C. $^1$H NMR (300 MHz, CDCl$_3$) δ 7.72 (s, 1H), 7.69 (s, 1H), 7.66 (d, J=1.3 Hz, 1H), 7.39 (dd, J=1.8, 8.8 Hz, 1H), 7.15 (dd, J=2.5, 8.8 Hz, 1H), 7.11 (d, J=2.5 Hz, 1H), 4.37 (t, J=6.9 Hz, 2H), 4.26 (m, 2H), 3.92 (s, 3H), 3.86 (q, J=7.2 Hz, 1H), 2.72 (dt, J=1.5, 6.5 Hz, 2H), 2.63 (m, 2H), 1.59 (d, J=7.2 Hz, 3H). Mass spectrum (API-TIS) m/z 380 (MH$^+$), 397 (M+18$^+$). Anal. calcd. for C$_{18}$H$_{21}$NO$_6$S: C, 56.98; H, 5.58; N, 3.69; S, 8.45. Found: C, 57.38; H, 5.56; N, 3.29; S, 8.45.

Example 2

2-((2-(Nitrooxy)ethyl)sulfonyl)ethyl(2S)-2-(6-methoxy(2-naphthyl)) propanoate 2a. 2-((2-Hydroxyethyl)sulfonyl)ethyl(2S)-2-(6-methoxy(2-naphthyl))propanoate The product of Example 1a (4.55 g, 13.60 mmol) was dissolved in methanol/water (3:1), 160 ml, and cooled to 0° C. OXONE® (17.56 g, 28.6 mmol) was added in portions, as a solid. The resulting mixture was stirred at 0° C. for 1.5 hours, and filtered then though Celite. The bulk of the solvent was evaporated, and the residue was partitioned between CH$_2$Cl$_2$ and water. The organic layer was dried over magnesium sulfate, and evaporated to give the title compound as an off-white solid (4.48 g, 90% yield). Mp 81-84° C. $^1$H NMR (300 MHz, CDCl$_3$) δ 7.73 (d, J=7.7 Hz, 1H), 7.71 (d, J=8.2 Hz, 1H), 7.65 (d, J=1.2 Hz, 1H), 7.36 (dd, J=1.8, 8.5 Hz, 1H), 7.17 (dd, J=2.5 Hz, 1H), 7.12 (d, J=2.5 Hz, 1H), 4.57 (m, 1H), 4.46 (m, 1H), 3.92 (s, 3H), 3.87 (q, J=7.2 Hz, 1H), 3.52 (m, 2H), 3.27 (app t, J=5.5 Hz, 2H), 2.64 (m, 1H), 2.58 (m, 1H), 1.87 (t, J=6.1 Hz, 1H), 1.60 (d, J=7.2 Hz, 3H). Mass spectrum (API-TIS) m/z 367 (MH$^+$), 384 (MNH$_4^+$). Anal. calcd. for C$_{18}$H$_{22}$O$_6$S: C, 59.00; H, 6.05; S, 8.75. Found: C, 59.08; H, 5.89; S, 8.75.

2b. 2-((2-(Nitrooxy)ethyl)sulfonyl)ethyl(2S)-2-(6-methoxy(2-naphthyl))propanoate The title compound was prepared from the product of Example 2a (4.48 g, 12.2 mmol) and fuming nitric acid (90%, 1.43 mL, 30.6 mmol) in acetic anhydride (4.54 mL, 49 mmol) following the procedure for Example 1b. After purification by column chromatography on silica, eluting with 50% ethyl acetate/hexane and trituration with ether/hexane, the title compound was obtained as white needles (3.348 g, 66% yield). Mp 83-85° C. $^1$H NMR (300 MHz, CDCl$_3$) δ 7.73 (d, J=8.4 Hz, 1H), 7.70 (d, J=8.9 Hz, 1H), 7.64 (d, J=1.3 Hz, 1H), 7.34 (dd, J=1.8, 8.4 Hz, 1H), 7.18 (dd, J=2.5, 8.9 Hz, 1H), 7.11 (d, J=2.5 Hz, 1H), 4.59 (m, 1H), 4.44 (m, 1H), 4.15 (m, 2H), 3.93 (s, 3H), 3.88 (q, 1H), 3.22 (m, 2H), 2.64 (m, 1H), 2.52 (m, J=7.2 Hz, 1H), 1.62 (d, J=7.2 Hz, 3H). Mass spectrum (API-TIS) m/z 412 (MH$^+$), 429 (M+18$^+$). Anal. calcd. for C$_{18}$H$_{21}$NO$_8$S: C, 52.55; H, 5.14; N, 3.40; S, 7.79. Found: C, 52.50; H, 4.94; N, 3.27; S, 7.79.

Example 3

2-((2-(Nitrooxy)ethyl)sulfinyl)ethyl(2S)-2-(6-methoxy(2-naphthyl)) propanoate 3a. 2-((2-Hydroxyethyl)sulfinyl)ethyl(2S)-2-(6-methoxy(2-naphthyl))propanoate and 2-((2-(Nitrooxy)ethyl)sulfinyl)ethyl(2S)-2-(6-methoxy(2-naphthyl))propanoate To acetic anhydride (9.1 mL, 98.1 mmol) at 0° C. was added fuming nitric acid (90%, 2.86 mL, 61.3 mmol) with stirring. After addition was complete, the mixture was stirred at 0° C. for 5 minutes, then added drop-wise to a solution of the product of Example 1a (4.10 g, 12.3 mmol) in ethyl acetate (20 mL) at 0° C. The reaction mixture was stirred at 0° C. for 10 minutes, then poured into a pre-cooled (0° C.) mixture of 25 mL of ethyl acetate and 50 mL of sodium bicarbonate. The mixture was stirred cold for 20 minutes, and then warmed to room temperature for 1 hour. The reaction mixture was partitioned between ethyl acetate and water, washed with sodium bicarbonate, water, and brine, and dried over sodium sulfate. The solvent was evaporated and the residue was purified by column chromatography on silica, eluting with methanol/ethyl acetate (gradient, 0% to 20%), gave 2-((2-nitrooxy)ethyl)sulfinyl)ethyl(2S)-2-(6-methoxy (2-naphthyl))propanoate as a pale yellow solid (1.07 g, 22% yield) and 2-((2-hydroxyethyl)sulfinyl)ethyl(2S)-2-(6-methoxy(2-naphthyl))propanoate as a white solid. 2-((2-hydroxyethyl)sulfinyl)ethyl(2S)-2-(6-methoxy(2-naphthyl))propanoate (1.87 g, 44% yield). Mp 74-86° C. $^1$H NMR (300 MHz, CDCl$_3$) δ 7.70 (d, J=8.6 Hz, 2H), 7.65 (d, J=1.0 Hz, 1H), 7.37 (dt, J=1.9, 8.5 Hz, 1H), 7.15 (dd, J=2.5, 8.8 Hz, 1H), 7.11 (d, J=2.3 Hz, 1H), 4.52 (m, 2H), 3.91 (s, 3H), 3.87 (q, J=7.2 Hz, 1H), 2.97 (m, 2H), 2.84 (br.s, 1H), 2.62 (m, 2H), 1.59 (d, J=7.2 Hz, 3H) Mass spectrum (API-TIS) m/z 351 (MH$^+$). 2-((2-(nitrooxy)ethyl)sulfinyl)ethyl(2S)-2-(6-methoxy(2-naphthyl))propanoate. Mp 72-88° C. $^1$H NMR (300 MHz, CDCl$_3$) δ 7.72 (d, J=8.4 Hz, 1H), 7.70 (d, J=8.9 Hz, 1H), 7.64 (br s, 1H), 7.35 (dt, J=2.1, 8.5 Hz, 1H), 7.16 (dd, J=2.5, 8.9 Hz, 1H), 7.11 (br s, 1H), 4.54-4.29 (m, 4H), 3.91 (s, 3H), 3.86 (q, J=7.2 Hz, 1H), 3.01-2.83 (m, 2H), 2.64-2.46 (m, 2H), 1.60 (d, J=7.2 Hz, 3H). Mass spectrum (API-TIS) m/z 396 (MH$^+$), 413 (M+18$^+$).

Example 4

2-((2-(Nitrooxy)ethyl)4-nitrophenyl)amino)ethyl 2-(6-methoxy-2-naphthyl)propanoate 4a. 2-((Hydroxyethyl)(4-nitrophenyl)amino)ethan-1-ol A mixture of 4-fluoronitrobenzene (5 g, 35 mmol) and diethanolamine (7.5 g, 71 mmol) was heated to 130° C. without solvent for 4 hours. The crude reaction mixture after chromatography on silica gel (gravity, methanol:dichloromethane 1:19 then 1:9) gave the title compound (6.7 g, 85% yield). $^1$H NMR (300 MHz, DMSO-d$_6$) δ 7.98 (d, 2H), 6.78 (d, 2H), 4.83 (t, 2H), 3.50-3.65 (m, 8H). $^{13}$C NMR (75 MHz, DMSO-d$_6$) δ 154.36, 136.16, 126.77, 111.66, 58.89, 54.17. Mass spectrum m/z 227 (MH$^+$). Anal. calcd. for C$_{10}$H$_{14}$N$_2$O$_4$ C, 53.09; H, 6.24; N, 12.38. Found C, 53.09; H, 6.32; N, 12.34.

4b. 2-((2-Hydroxyethyl)(4-nitrophenyl)amino)ethyl 2-(6-methoxy-2-naphthyl)propanoate A solution of the product of Example 4b (6.7 g, 29.6 mmol), N,N-dimethylaminopyridine (DMAP, 0.24 g, 2 mmol), and (2S)-2-(6-methoxy(2-naphthyl))propanoic acid (naproxen, 2.27 g, 9.9 mmol) in dichloromethane (90 ml) with enough DMF to cause dissolution, was treated with 1-ethyl-3(3-dimethylamino)-1-propylcarbodiimide (2.35 g, 12.3 mmol). The reaction mixture was stirred at room temperature for 4 hours, diluted with CH$_2$Cl$_2$, washed with water (8×), HCl (2N), brine, dried with sodium sulfate, filtered and the organic layer evaporated. The residue was chromatographed on silica gel (gravity, methanol:dichloromethane, 1:24) to give the title compound (2.7 g, 64% yield). $^1$H NMR (300 MHz, CDCl$_3$) δ 7.87-7.95 (m, 2H), 7.60-7.69 (m, 2H), 7.56 (s, 1H), 7.26-7.32 (s, 1H), 7.11-7.19 (m, 1H), 7.08 (br s, 1H), 6.46-6.54 (m, 2H), 4.22-4.45 (m, 2H), 3.89 (s, 3H), 3.77 (q, j=6.0 Hz, 1H), 3.55-3.67 (m, 4H), 3.27-3.39 (m, 2H), 1.90 (br s, 1H), 1.51 (d, J=6.0 Hz, 3H). $^{13}$C NMR (75 MHz, CDCl$_3$) δ 174.63, 157.75, 152.66, 137.28, 135.06, 133.67, 129.07, 128.76, 127.21, 125.96, 125.89, 119.16, 110.59, 105.53, 61.61, 59.57, 55.28, 53.19, 50.07, 45.36, 18.30. Mass spectrum m/z 439 (MH$^+$).

4c. 2-((2-(Nitrooxy)ethyl)4-nitrophenyl)amino)ethyl 2-(6-methoxy-2-naphthyl)propanoate Acetic anhydride (5 mL) was cooled to <10° C. (internal temperature) and fuming nitric acid (90%, 1 mL) was added keeping the same temperature. A solution of the product of Example 4b (2.4 g, 5.5 mmol) in ethyl acetate (30 ml) was added drop-wise at the same temperature. After the addition was complete, the reaction mixture was stirred in the ice bath for 1 hour, poured carefully into excess sodium bicarbonate solution and extracted with ethyl acetate. The combined organic layers were dried with sodium sulphate, filtered, evaporated and the residue chromatographed on silica gel (gravity, ethyl acetate:hexane 1:1) to give the title compound (1.7 g, 64% yield). $^1$H NMR (300 MHz, CDCl$_3$) δ 7.98 (dd, J=11.0 and 3.4 Hz, 2H), 7.65 (dd, J=8.4 and 2.4 Hz, 2H), 7.53 (s, 1H), 7.28 (dd, J=8.5 and 1.8 Hz, 1H), 7.16 (dd, J=8.9 and 2.5 Hz, 1H), 7.10 (d, J=2.3 Hz, 1H), 6.45-6.51 (m, 2H), 4.08-4.48 (m, 4H), 3.93 (s, 3H), 3.80 (q, J=7.1 Hz, 1H), 3.59 (q, J=5.9 Hz, 2H), 3.20-3.43 (m, 2H), 1.54 (d, J=7.2 Hz, 3H). $^{13}$C NMR (75 MHz, CDCl$_3$) δ 174.34, 157.84, 151.47, 138.11, 135.13, 133.70, 129.03, 128.77, 127.28, 126.10, 125.91, 119.28, 110.57, 105.53, 68.93, 61.30, 55.31, 49.82, 47.62, 45.35, 18.19. Mass spectrum m/z 484 (MH$^+$).

Example 5

(2R)-2,3-Bis(nitrooxy)propyl(2S)-2(6-methoxy(2-naphthyl)propanoate 5a. 1-(((4S)-2,2-Dimethyl(1,3-dioxolan-4-yl))methoxy)-2,2-dimethyl-1,1-diphenyl-1-silapropane To a solution of ((4R)-2,2-dimethyl-1,3-dioxolan-4-yl)methan-1-ol (9 g, 68.6 mmol) in anhydrous dichloromethane (40 mL) were added triethylamine (11.2 mL), tert-butylchlorodiphenylsilane (19.8 g, 372 mmol), and N,N-dimethylaminopyridine (DMAP, 418 mg, 3.4 mmol) at room temperature under a nitrogen atmosphere. The reaction mixture was stirred at room temperature overnight. It was then diluted with additional dichloromethane and the reaction mixture was washed with water, brine, dried over sodium sulfate, filtered and evaporated to give the title compound (27 g) which was used in the next step without further purification.

5b. (2S)-3-(2,2-Dimethyl-1,1-diphenyl-1-silapropoxy)propane-1,2-diol

The product of Example 5a (12.3 g, 33.2 mmol) was dissolved in 70% aqueous acetic acid (100 mL) and the resulting solution was stirred at 60° C. for 2 hours. The reaction mixture was then cooled to room temperature and sodium carbonate was added to neutralize the acid. The reaction mixture was then extracted with ethyl acetate, the combined organic extracts were washed with water, brine, dried over sodium sulfate, filtered, and evaporated to give the title compound (8.3 g) as a colorless viscous oil which was used as such in the next step.

5c. ((1S)-1-((2,2-Dimethyl-1,1-diphenyl-1-silapropoxy)methyl)-2-(nitrooxy)ethyl)nitrooxy The product of Example 5b (9.82 g, 38.5 mmol) was dissolved in ethyl acetate (200 mL) and the resulting solution was cooled to 0° C. A mixture of acetic acid (20 mL) and fuming nitric acid (90%, 3.8 mL) was then added followed by acetic anhydride (20 mL). The resulting mixture was stirred at room temperature overnight. The reaction mixture was then diluted with ethyl acetate, washed with saturated aqueous sodium bicarbonate, water, brine, dried over sodium sulfate, filtered, and the filtrate was concentrated in vacuo to give the title compound (10.6 g, 80% yield) as a yellow oil which was used without further purification.

5d. (2R)-2,3-Bis(nitrooxy)propan-1-ol

The product of Example 5c (8.67 g, 25.1 mmol) was dissolved in acetonitrile (200 mL) and hydrofluoric acid (48% solution in water, 100 mL) was added. The reaction mixture was stirred at room temperature overnight. A saturated aqueous sodium bicarbonate was added to neutralize the acidic solution to pH 7.0 and the mixture was extracted with ethyl acetate. The combined extracts were washed with saturated aqueous sodium bicarbonate, water, brine, dried over sodium sulfate, filtered, and the filtrate was concentrated in vacuo to give the crude product that was purified by column chromatography over silica gel, eluting with 5% ethyl acetate in hexane to give the title compound (1.38 g, 23% yield) as a colorless oil.

5e. (2R)-2,3-Bis(nitrooxy)propyl(2S)-2(6-methoxy (2-naphthyl)propanoate

To a solution of (2S)-2-(6-methoxy(2-naphthyl))propanoic acid (naproxen, 1.05 g, 5 mmol) and the product of Example 5d (0.91 g, 5 mmol) in anhydrous dichloromethane (25 mL) were added 1-ethyl-3-(3-dimethylaminopropyl) carbamide hydrochloride (EDAC) (0.955 g, 5 mmol) and N,N-dimethylaminopyridine (DMAP, 0.61 g, 5 mmol) at 0° C. under nitrogen atmosphere. The reaction mixture was stirred at room temperature for 5 hours. The solvent was evaporated under vacuo and the residue was extracted with ethyl acetate, washed with water, brine, dried over sodium sulfate, filtered, and the combined organic extracts were evaporated. The product was purified by column chromatography on silica gel eluting with EtOAc:hexane (20:80) to give the title compound (1.5 g, 82% yield) as a white solid, mp 54-58° C. $^1$H NMR (300 MHz, CDCl$_3$) δ 7.72 (dd, J=9 and 2 Hz, 2H), 7.65 (s, 1H), 7.36 (dd, J=8.5 and 1.8 Hz, 1H), 7.16 (dd, J=8.8 and 2.5 Hz, 1H), 7.12 (d, J=2.2 Hz, 1H), 5.33 (m, 1H), 4.55 (dd, J=12.9 and 3.6 Hz, 1H), 4.46 (dd, J=12.5 and 4.2 Hz, 1H), 4.32 (dd, J=12.8 and 6.5 Hz, 1H), 4.21 (dd, J=12.5 and 5.5 Hz, 1H), 3.91 (s, 3H), 3.89 (q, J=7.1 Hz, 1H), 1.6 (d, J=7.1 Hz, 3H); $^{13}$C NMR (75 MHz, CDCl$_3$) δ 173.8, 157.7, 134.6, 133.8, 129.2, 128.8, 127.3, 125.9, 125.8, 119.2, 105.6, 76.2, 68.4, 60.4, 55.2, 45.1, 18.0; LRMS (APIMS) m/z 395 (MH$^+$).

Example 6

(2R)-7-(Nitrooxy)-4,8-dioxabicyclo(3.3.0)oct-2-yl (2S)-2-(6-methoxy(2-naphthyl))propanoate To a solution of (2S)-2-(6-methoxy(2-naphthyl))propanoic acid (naproxen, 1 g, 4.43 mmol) and (2S)-7-(nitrooxy)-4,8-dioxabicyclo(3.3.0)octan-2-ol (isosorbide 5-mononitrate, 1 g, 5.21 mmol) in anhydrous dichloromethane (25 mL) were added 1-(3-(dimethylamino)propyl)-3-ethylcarbodiimide hydrochloride (EDAC, 1.17 g, 1.4 eq) and a catalytic amount of N,N-dimethylaminopyridine (DMAP) at room temperature under nitrogen atmosphere. The reaction mixture was stirred at room temperature overnight. The reaction mixture was diluted with $CH_2Cl_2$ and washed $H_2O$, brine, dried over sodium sulfate, filtered, and the organic extracts were evaporated. The product was purified by column chromatography on silica gel eluting with EtOAc:hexane (3:7 to 1:1) to give the title compound (1.71 g, 97.6% yield) as a white crystalline solid. Mp 112-113° C. $^1H$ NMR (300 MHz, $CDCl_3$) δ 7.67 (m, 3H), 7.37 (m, 1H), 7.14 (m, 2H), 5.26 (m, 2H), 4.78 (t, J=5.2 Hz, 1H), 4.21 (d, J=4.9 Hz, 1H), 4.02-3.77 (m, 5H), 3.92 (s, 3H), 1.56 (d, 3H, J=7.1 Hz); LRMS (APIMS) m/z 404 ($MH^+$).

Example 7

Phosphonomethyl(2S)-2-(6-methoxy(2-naphthyl))propanoate 3-(nitrooxy)propylamine nitric acid salt 7a. (Diethoxycarbonyl)methyl(2S)-2-(6-methoxy(2-naphthyl))propanoate A solution of (2S)-2-(6-methoxy(2-naphthyl))propanoic acid (naproxen, 16.55 g, 71.9 mmol), diethyl(hydroxymethy) phosphonate (12.68 g, 75.4 mmol) and N,N-dimethylaminopyridine (DMAP, 20 mg) in dichloromethane (200 ml) was treated with 1-(3-(dimethylamino)propyl)-3-ethylcarbodiimide hydrochloride (EDAC, 14.45 g, 75.4 mmol) and stirred at room temperature overnight. The reaction mixture was washed with 1N HCl (100 ml) and water (200 mL×2), dried over sodium sulfate, filtered, and concentrated. The product was purified by silica gel chromatography with ethyl acetate:hexane (2:1) as eluent ($R_f$=0.2) to give the title compound (20.63 g, 75% yield). $^1H$ NMR (300 MHz, $CDCl_3$) δ 7.65-7.7 (m, 3H), 7.35-7.45 (m, 1H), 7.1-7.15 (m, 2H), 4.39 (d, J=8.6 Hz, 2H), 4.05-3.85 (m, 5H), 3.86 (s, 3H), 1.61 (d, J=7.2 Hz), 1.25-1.11 (m, 6H). $^{13}C$ NMR (75 MHz, $CDCl_3$) δ 173.5 (d, $J_{CP}$=7.9 Hz), 157.7, 134.9, 133.7, 129.1, 128.8, 127.1, 126.1, 119.0, 105.5, 62.6, 57.1 (d, $J_o$)=167.3 Hz), 55.2, 45.1, 18.3, 16.2. Anal. calcd. for $C_{19}H_{17}O_6P$: C, 60.0; H, 6.62. Found C, 59.83; H, 6.41.

7b. Phosphonomethyl(2S)-2-(6-methoxy(2-naphthyl))propanoate

Bromotrimethylsilane (14 mL, 106.1 mol) was added to an ice-cooled solution of the product of Example 7a in dichloromethane (250 ml). The resulted solution was stirred in an ice-bath for 15 minutes and then at room temperature overnight. The reaction was quenched with 1N HCl (80 ml) and methanol (20 ml), stirred for 2 hours and the solvent was evaporated. The residue was dissolved in EtOAc (300 mL), washed with water (150 mL×2), dried over sodium sulfate, filtered, and concentrated to give a white solid. The solid was suspended in a solution of chloroform (50 mL) and hexane (200 mL), filter, and the solid was washed with hexane (100 mL) and dried under vacuum to give the title compound (12.73 g, 82% yield). $^1H$ NMR (300 MHz, DMSO-$d_6$) δ 7.7-8.0 (m, 3H), 7.4-7.5 (m, 1H), 7.29 (d, J=2.4 Hz, 1H), 7.1-7.2 (m, 1H), 4.07-4.3 (m, 4H), 3.96 (q, J=7.2 Hz, 1H), 3.86 (s, 3H), 1.49 (d, J=7.2 Hz, 3H). $^{13}C$ NMR (75 MHz, DMSO-$d_6$) δ 173.4 (d, $J_{CP}$=7.5 Hz), 157.2, 135.4, 133.3, 129.2, 128.4, 127.0, 126.3, 125.7, 118.7, 105.7, 62.6 (d, $J_{CP}$=160.2 Hz), 55.2, 44.3, 18.7. Mass spectrum m/z 323 (M–H)$^-$. Anal. calcd. for $C_{15}H_{15}O_6P$: C, 55.56; H, 5.28. Found C, 55.44; H, 5.32.

7c. 3-(Nitrooxy)propylamine nitric acid salt

A solution of 3-amino-1-propanol (6.17 g, 82.2 mmol) was added, drop-wise, to an ice-cooled solution of fuming nitric acid (90%, 12 mL) in acetic anhydride (50 mL). The reaction was stirred in an ice-bath for 10 minutes and then at room temperature for 10 minutes. The solvent was evaporated under vacuum at 40° C. The residue was stirred in diethylether (200 mL) until the product precipitated. The mixture was filtered and the white crystalline solid was dried in vacuo to give the title compound (12.1 g, 80% yield). $^1H$ NMR (300 MHz, DMSO-$d_6$) δ 4.57 (br. t, 2H), 2.8-3.0 (m, 2H), 1.98-1.93 (m, 2H). $^{13}C$ NMR (75 MHz, DMSO-$d_6$) δ 70.9, 36.1, 24.5. MS m/z 121 (M–$NO_3$)$^+$.

7d. Phosphonomethyl(2S)-2-(6-methoxy(2-naphthyl))propanoate 3-(nitrooxy) propylamine nitric acid salt The product of Example 7c (0.264 g, 2.2 mmol) in dichloromethane (5 ml) was added to the product of Example 7b in methanol (5 mL) and the resulting solution stirred for 5 minutes. The solution was evaporated to dryness and the solid was washed with diethyl ether (50 mL), dried under vacuum (0.43 g, 90% yield) to give the title compound. Mp 123-4° C. $^1H$ NMR (300 MHz, DMSO-$d_6$) δ 7.8-7.7 (m, 3H), 7.43-7.4 (m, 1H), 7.27 (d, J=2.4 Hz, 1H), 7.15-7.11 (m, 1H), 4.57 (t, J=6.3 Hz, 4H), 4.1-3.7 (m, 3H), 3.86 (s, 3H), 2.70 (t, J=6.9 Hz, 4H), 1.9-1.8 (m, 4H), 1.46 (d, J=7.1 Hz, 3H). $^{13}C$ NMR (75 MHz, DMSO-$d_6$) δ 174.0 (d, $J_{CP}$=7.5 Hz), 157.1, 135.9, 133.2, 129.1, 128.3, 126.8, 126.3, 125.5, 118.6, 105.6, 71.4, 61.6 (d, $J_{CP}$=153.8 Hz), 55.1, 44.4, 36.1, 26.6, 18.8.

Example 8

Phosphonomethyl(2S)-2-(6-methoxy(2-naphthyl))propanoate 4-nitro-1-(nitrooxy)-2-((nitrooxy)methyl)but-2-ylamine salt 4-Nitro-1-(nitrooxy)-2-((nitrooxy)methyl)but-2-ylamine (0.734 g, 2.86 mmol, the hydrochloride salt was prepared according to the procedure in U.S. Pat. No. 2,975,208 and then converted to the free acid in $CH_2Cl_2$ (5 ml) was added to the product of Example 7b (0.39 g, 1.2 mmol) in methanol (5 mL) and stirred for 5 minutes. The solution was evaporated to dryness. The residue was dissolved in EtOAc (4 mL) and treated with hexane (40 mL). The solvent was removed and the resulting oil was dried under vacuum to gave the title compound as a foam (0.563 g, 81% yield). Mp 39-41° C. $^1H$ NMR (300 MHz, DMSO-$d_6$) δ 7.8-7.7 (m, 3H), 7.43-7.4 (m, 1H), 7.29 (d, J=2.4 Hz, 1H), 7.17-7.13 (m, 1H), 4.57 (s, 6H), 4.3-3.9 (m, 2H), 3.96 (q, J=7.1 Hz, 1H), 3.86 (s, 3H), 1.46 (d, J=7.1 Hz, 3H). $^{13}C$ NMR (75 MHz, DMSO-$d_6$) δ 173.5 (d, $J_{CP}$=8.2 Hz), 157.2, 135.4, 133.3, 129.1, 128.4, 126.9, 126.3, 125.6, 118.6, 105.7, 72.4, 61.6 (d, $J_{CP}$=153.8Hz), 55.1, 53.8, 44.3, 18.7.

Example 9

(5-((Nitrooxy)methyl-1,3-dioxan-5-yl)methyl(2S)-2-(6-methoxy(2-naphthyl))-propanoate 9a. 5-(Hydroxymethyl)-1,3-dioxan-5-yl)methyl(2S)-2-(6-methoxy(2-naphthyl))-propanoate To a stirred solution of 1,3-dioxane-5,5-dimethanol (7.41 g, 50 mmol), (2S)-2-(6-methoxy(2-naphthyl))propanoic acid (naproxen, 5.76 g, 25 mmol) and 1,3-dicyclohexylcarbodiimide (5.16 g, 25 mmol) in $CH_2Cl_2$ (150 mL) was added a catalytic amount of N,N-dimethylaminopyridine (DMAP, 10 mg). The reaction mixture was stirred at ambient temperature for 15 hours, filtered, and the filtrate was concentrated. The crude product was purified by chromatography (silica gel, 1:1 EtOAc:Hex) to give the title compound (7.92 g, 88% yield) as white prisms. Mp 106° C. $^1$H NMR (300 MHz, $CDCl_3$) δ 7.67-7.60 (m, 3H), 7.35-7.31 (m, 1H), 7.12-7.05 (m, 2H), 4.66 (d, J=6.1 Hz, 1H), 4.61 (d, J=6.1 Hz, 1H), 4.24 (d, J=11.5 Hz, 1H), 4.12 (d, J=11.5 Hz, 1H), 3.85 (s, 3H), 3.88-3.80 (m, 1H), 3.6-3.4 (m, 4H), 3.3-3.1 (m, 2H), 2.33 (br, 1H), 1.54 (d, J=7.1 Hz, 3H). $^{13}$C NMR (75 MHz, $CDCl_3$) δ 175.3, 157.7, 135.1, 133.7, 129.2, 128.8, 127.2, 125.9, 119.1, 105.5, 94.1, 69.2, 68.8, 63.1, 61.4, 55.2, 45.4, 39.6, 17.9. Mass spectrum (API-TIS) m/z 361.2 ($MH^+$).

9b. (5-((Nitrooxy)methyl)-1,3-dioxan-5-yl)methyl (2S)-2-(6-methoxy(2-naphthyl))-propanoate Acetic anhydride (6 mL) was cooled to <10° C. (internal temperature) and fuming nitric acid (90%, 2 mL. 43 mmol) was added keeping the same temperature. A solution of the product of Example 9a (5.40 g, 15 mml) in THF (100 mL) was added rapidly. After the addition was complete, the reaction mixture was stirred in the ice bath for 1 hour. The mixture was taken up with EtOAc, washed with ice plus saturated aqueous $NaHCO_3$ (2×), brine, dried over $Na_2SO_4$, filtered, and concentrated. The resulting solid was purified by crystallization from 1:2 EtOAc:Hex to give the title compound (4.81 g, 79% yield) as white flakes. Mp 98° C. $^1$H NMR (300 MHz, $CDCl_3$) δ 7.72 (d, J=2.5 Hz, 1H), 7.68 (d, J=2.8 Hz, 1H), 7.63 (s, 1H), 7.34 (dd, J=8.5, 1.7 Hz, 1H), 7.18-7.10 (m, 2H), 4.80 (d, J=6.1 Hz, 1H), 4.56 (d, J=6.1 Hz, 1H), 4.38 (d, J=6.9 Hz, 1H), 4.32 (d, J=6.9 Hz, 1H), 4.11 (d, J=11.6 Hz, 1H), 3.96 (d, J=11.6 Hz, 1H), 3.91 (s, 3H), 3.88 (q, J=7.2 Hz, 1H), 3.68 (t, J=12.2 Hz, 2H), 3.51 (td, J=8.1, 3.5 Hz, 2H), 1.59 (d, J=7.2 Hz, 3H). $^{13}$C NMR (75 MHz, $CDCl_3$) δ 173.9, 157.7, 135.0, 133.8, 129.1, 128.8, 127.3, 125.9, 125.8, 119.2, 105.6, 94.2, 70.6, 68.61, 68.58, 62.6, 55.3, 45.3, 37.9, 17.9. Mass spectrum (API-TIS) m/z 423.2 ($M+NH_4^+$). Anal. Calcd. for $C_{20}H_{23}NO_8$: C, 59.25; H, 5.72; N, 3.46. Found: C, 59.37; H, 5.81; N, 3.19.

Example 10

2,2-Bis(nitrooxy)propyl(2S)-2-(6-methoxy(2-naphthyl))propanoate

10a. 3-Hydroxy-2-(hydroxymethyl)-2-methylpropyl (2S)-2-(6-methoxy(2-naphthyl))-propanoate To a stirred solution of 1,1,1-tris(hydroxymethyl)ethane (13.1 g, 109 mmol), (2S)-2-(6-methoxy(2-naphthyl))propanoic acid (naproxen, 5.00 g, 21.7 mmol), 1-(3-(dimethylamino)propyl)-3-ethylcarbodiimide hydrochloride (4.80 g, 25 mmol), and N,N-dimethylaminopyridine (DMAP, 20 mg, catalytic amount) in acetonitrile (200 mL) was added triethylamine (4.2 mL, 30 mmol). The reaction mixture was stirred at ambient temperature for 25 hours, filtered, and the filtrate was concentrated to dryness. The residue was diluted with EtOAc, washed with 1N HCl (2×), saturated $NaHCO_3$, and brine, dried over $Na_2SO_4$, filtered, and concentrated. The resulting material was purified by crystallization (2×) from EtOAc/Hexanes (1:3 v:v) to give the title compound (4.72 g, 66% yield) as white flakes. Mp 105° C. $^1$H NMR (300 MHz, $CDCl_3$) δ 7.72 (d, J=2.0 Hz, 1H), 7.69 (d, J=2.5 Hz, 1H), 7.66 (s, 1H), 7.39 (dd, J=8.5, 1.7 Hz, 1H), 7.17-7.10 (m, 2H), 4.25 (d, J=11.3 Hz, 1H), 4.09 (d, J=11.3 Hz, 1H), 3.90 (s, 3H), 3.88 (q, J=7.1 Hz, 1H), 3.46-3.25 (m, 4H), 2.65-2.55 (m, 2H), 1.60 (d, J=7.1 Hz, 3H), 0.67 (s, 3H). $^{13}$C NMR (75 MHz, $CDCl_3$) δ175.8, 157.7, 135.3, 133.8, 129.2, 128.9, 127.3, 126.0, 119.2, 105.6, 67.7, 67.5, 66.8, 55.3, 45.6, 40.9, 18.1, 16.7. LRMS (API-TIS) m/z 350.2 (($M+NH_4^+$).

10b. 2,2-Bis(nitrooxy)propyl(2S)-2-(6-methoxy(2-naphthyl))propanoate

Acetic anhydride (12 mL) was cooled to <10° C. (internal temperature) and fuming nitric acid (90%, 4 mL. 86 mmol) was added keeping the same temperature. After 30 minutes a pre-cooled solution (−10° C.) of the product of Example 10a (4.72 g, 14.2 mmol) in THF (30 mL) was added rapidly. After the addition was complete, the reaction mixture was stirred in the ice bath for 15 minutes. The mixture was poured into ice plus EtOAc, washed with saturated $NaHCO_3$ (3×), dried over $Na_2SO_4$, filtered, and concentrated. Chromatography of the residue gave the title compound (3.60 g, 60% yield) as a yellow solid. Mp 67-68° C. $^1$H NMR (300 MHz, $CDCl_3$) δ 7.70 (d, J=2.0 Hz, 1H), 7.67 (d, J=2.5 Hz, 1H), 7.63 (s, 1H), 7.34 (dd, J=8.5, 1.7 Hz, 1H), 7.17-7.10 (m, 2H), 4.21-4.10 (m, 4H), 4.08 (d, J=11.5 Hz, 1H), 3.94 (d, J=11.5 Hz, 1H), 3.90 (s, 3H), 3.89 (q, J=7.2 Hz, 1H), 1.58 (d, J=7.2 Hz, 3H), 0.94 (s, 3H). $^{13}$C NMR (75 MHz, $CDCl_3$) δ 173.8, 157.7, 134.9, 133.7, 129.1, 128.8, 127.3, 125.9, 125.8, 119.2, 105.5, 73.1, 72.9, 65.1, 55.2, 45.3, 38.5, 17.8, 16.9. LRMS (API-TIS) m/z 423.2 (($M+H)^+$), 440.2 (($M+NH_4)^+$).

Example 11

3-(4-((Nitrooxy)methyl)phenylcarbonyloxy)-2-oxopropyl(2S)-2-(6-methoxy(2-naphthyl))propanoate

11a. 4-((Nitrooxy)methyl)benzoic acid

A solution of silver nitrate (17.73 g, 104.4 mmol) and α-bromo-p-toluic acid (10.84 g, 50.4 mmol) in THF (150 mL) and acetonitrile (150 mL) was stirred at room temperature overnight and then at 50° C. for 1 hour. The reaction mixture was then cooled to ambient temperature and stirred with brine (150 mL) for 1 hour. The resulting mixture was filtered through Celite and washed with water. The filtrate was concentrated and then extracted with ethyl acetate. The combined organic layers were washed with water, brine, dried over $Na_2SO_4$, filtered, concentrated and dried under vacuum. The crude product was washed with $CH_2Cl_2$ (50 mL) on a Buchner funnel then dried under vacuum to give the title compound as a white solid (7.27 g, 73% yield). Mp 159-161° C. $^1$H NMR (300 MHz, DMSO-$d_6$) δ 8.02 (d, J=8.1 Hz, 2H), 7.60 (d, J=8.1 Hz, 2H), 5.67 (s, 2H). $^{13}$C NMR (75 MHz, DMSO-$d_6$) δ166.9, 137.3, 131.4, 129.7, 129.0, 74.3. Mass spectrum (API-TIS) m/z 196 ($MH)^+$.

11b. 3-Hydroxy-2-oxopropyl(2S)-2-(6-methoxy(2-naphthyl))propanoate

A solution of 1,3-dicyclohexylcarbodiimide (2.84 g, 13.8 mmol) in acetone (40 mL) was added, drop-wise, to a solution of (2S)-2-(6-methoxy(2-naphthyl))propanoic acid (naproxen, 3.14 g, 13.6 mmol), 1,3-dihydroxy-acetone (3.11 g, 34.5 mmol) and N,N-dimethylaminopyridine (DMAP, 1.4 g, 11.5 mmol) in acetone (100 mL) and stirred at ambient temperature overnight. The byproduct, dicyclohexyl urea was removed by filtration. The filtrate was concentrated and the residue was dissolved in CH$_2$Cl$_2$ (150 mL), washed with 3N HCl (150 mL), water (150 mL×3), brine, and dried over Na$_2$SO$_4$, filtered and concentrated. The product was separated by silica gel column chromatography eluting with ethyl acetate/hexane (1:2, Rf=0.13) to obtained a mixture of the title compound and its dimer. The reaction mixture was treated with ethyl ether and the dimer was removed by filtration. The filtrate was concentrated and dried under vacuum to give the title compound as a sticky oil (1.59 g). The resulted material was use in the next step without further purification. Mass spectrum (API-TIS) m/z 303 (MH)$^+$.

11c. 3-(4-((Nitrooxy)methyl)phenylcarbonyloxy)-2-oxopropyl(2S)-2-(6-methoxy(2-naphthyl))propanoate 1,3-Dicyclohexylcarbodiimide (1.18 g, 5.7 mmol) was added to a solution of Example 11b. (1.59 g, 5.26 mmol), Example 11a (1.03 g, 5.2 mmol) and N,N-dimethylaminopyridine (DMAP, 0.66 g, 5.36 mmol) in CHCl$_3$ (100 mL) and stirred at ambient temperature overnight. The byproduct, dicyclohexyl urea was removed by filtration. The filtrate was concentrated and the residue was dissolved in ethyl acetate (150 mL), washed with 3N HCl (100 mL), water (100 mL), brine, and dried over Na$_2$SO$_4$, filtered and concentrated. The resulting residue was treated with ethyl acetate (50 mL) and cooled to −30° C. in a dry-ice bath and then filtered. The filtrate was concentrated, dissolved in ethyl ether (100 mL) and stirred until the product precipitated. The solid was dried under vacuum to give the title compound (1.11 g, 44% yield). Mp 105-107° C. $^1$H NMR (300 MHz, CDCl$_3$) δ 8.01-8.04 (m, 2H), 7.67-7.72 (m, 3H), 7.4-7.43 (m, 3H), 7.09-7.14 (m, 2H), 5.42 (s, 2H), 4.85 (d, J=3.9 Hz, 2H), 4.78 (d, J=3.5 Hz, 2H), 3.98 (q, J=7.1 Hz, 1H), 3.87 (s, 3H), 1.62 (d, J=7.1 Hz, 3H). $^{13}$C NMR (75 MHz, CDCl$_3$) δ197.6, 173.8, 164.9, 157.6, 137.8, 134.7, 133.7, 130.3, 129.6, 129.2, 128.8, 128.4, 127.2, 126.0, 119.0, 105.5, 73.4, 66.6, 66.5, 55.2, 45.0, 18.3, 14.1. Mass spectrum (API-TIS) m/z 482 (MH)$^+$.

Example 12

2-Methyl-2-nitro-3-(nitrooxy)propyl(2S)-2-(6-methoxy(2-naphthyl)) propanoate 12a. 3-Hydroxy-2-methyl-2-nitropropyl(2S)-2-(6-methoxy(2-naphthyl))propanoate A solution of 1,3-dicyclohexylcarbodiimide (4.23 g, 20.5 mmol), (2S)-2-(6-methoxy(2-naphthyl))propanoic acid (naproxen, 4.34 g, 18.9 mmol), and 2-nitro-2-methyl-1,3-propanediol (2.56 g, 19.0 mmol) in CH$_2$Cl$_2$ (50 mL) and THF (50 mL) was stirred at ambient temperature overnight. The solvent was evaporated and EtOAc (100 mL) was added to the resulting crude material, cooled in a dry-ice bath and the byproduct, dicyclohexyl urea was removed by filtration. The product was separated by silica gel column chromatography eluting with ethyl acetate/hexane (1:3, Rf=0.1) to give the title compound (a mixture of diasteromers) as an oil (2.77 g, 42% yield). $^1$H NMR (300 MHz, CDCl$_3$) δ 7.69-7.60 (m, 3H), 7.34-7.3 (m, 1H), 7.14-7.08 (m, 2H), 4.44 (d, J=4.2 Hz, 2H), 3.86 (s, 3H), 3.85 (q, J=7.2 Hz, 1H), 3.7 (m, 1H), 1.55 (d, J=7.2 Hz, 3H), 1.36 & 1.40 (s, 3H). $^{13}$C NMR (75 MHz, CDCl$_3$) δ 174.14, 174.02, 157.57, 134.53, 134.51, 133.64, 129.13, 128.7, 127.17, 125.87, 125.84, 119.0, 105.47, 89.53, 89.42, 64.67, 64.52, 64.19, 55.12, 45.04, 18.25, 18.03, 17.82, 17.79. Mass spectrum (API-TIS) m/z 348 (MH)$^+$.

12b. 2-Methyl-2-nitro-3-(nitrooxy)propyl(2S)-2-(6-methoxy(2-naphthyl))propanoate Fuming nitric acid (90%, 120 μL, 2.9 mmol) was added to an ice-cold acetic anhydride (10 mL) and the mixture was stirred in the ice-bath for 5 minutes then for an additional 5 minutes at ambient temperature. The solution was then added to an ice-cold solution of Example 12a (0.92 g, 2.7 mmol) in EtOAc (10 mL). The reaction mixture was stirred in the ice-bath for 5 minutes and then at ambient temperature for 2 hours. A second and equal portion of acetyl nitrate was added to the reaction mixture and then stirred for an additional hour. The reaction mixture was washed with saturated NaHCO$_3$, water and brine, and dried over Na$_2$SO$_4$, filtered and concentrated under reduced pressure. The product was separated by silica gel column chromatography eluting with ethyl acetate/hexane (1:3, Rf=0.4) to give the title compound (a mixture of diasteromers) as a sticky oil (0.70 g, 67% yield). The oil solidified after standing overnight at ambient temperature. Mp 58-74° C. $^1$H NMR (300 MHz, CDCl$_3$) δ 7.69-7.59 (m, 3H), 7.32-7.28 (m, 1H), 7.15-7.08 (m, 2H), 4.7-4.3 (m, 4H), 3.85 (s, 3H), 3.83 (q, J=7.1 Hz, 1H), 1.54 (m, 3H), 1.43 & 1.42 (s, 3H). $^{13}$C NMR (75 MHz, CDCl$_3$) δ 173.07, 174.03, 157.64, 134.37, 134.32, 133.68, 129.05, 128.66, 127.21, 127.17, 125.80, 125.67, 119.06, 119.04, 105.41, 86.04, 85.99, 70.95, 70.63, 64.35, 64.31, 55.04, 44.89, 44.84, 18.68, 18.55, 17.60. Mass spectrum (API-TIS) m/z 393.

Example 13

2-Nitro-3-(nitrooxy)-2-((nitrooxy)methyl)propyl (2S)-2-(6-methoxy(2-naphthyl))propanoate 13a. 3-Hydroxy-2-(hydroxymethyl)-2-nitropropyl (2S)-2-(6-methoxy(2-naphthyl))propanoate A solution of (2S)-2-(6-methoxy(2-naphthyl))propanoic acid (naproxen, 4.27 g, 18.5 mmol), 2-hydroxymethyl-2-nitro-1,3-propanediol (2.89 g, 19.1 mmol), N,N-dimethylaminopyridine (DMAP, 0.88 g, 7.2 mmol), 1-(3-dimethylaminopropyl)-3-ethylcarbodiimide hydrochloride (4.86 g, 25.4 mmol) and NEt(i-Pr)$_2$ (11 mL, 63.2 mmol) in acetone (100 mL) was stirred at ambient temperature overnight. The reaction mixture was evaporated to dryness and the residue was partitioned between 3N HCl (100 mL) and CH$_2$Cl$_2$ (200 mL×2). The combined organic layer was back washed with water and brine, dried over Na$_2$SO$_4$, filtered, concentrated and dried under vacuum. The product was separated by silica gel column chromatography eluting with ethyl acetate/hexane (gradient from 1:2 to 1:1, Rf=0.1 in 1:2) to give the title compound as a white solid (2.48 g, 39% yield). Mp 124-126° C. $^1$H NMR (300 MHz, 10% CD$_3$OD/CDCl$_3$) δ 7.73-7.64 (m, 3H), 7.37-7.33 (m, 1H), 7.17-7.12 (m, 2H), 4.44 (d, J=2.6 Hz, 2H), 3.92 (s, 3H), 3.9-3.7 (m, 5H), 3.4 (br, 2H), 1.58 (d, J=7.2 Hz, 3H). $^{13}$C NMR (75 MHz, 10% CD$_3$OD/CDCl$_3$) δ 174.1, 157.4, 134.5, 133.5, 129.0, 128.6, 127.0, 125.7, 118.8, 105.4, 92.4, 61.2, 60.1, 55.0, 45.0, 17.7.

13b. 2-Nitro-3-(nitrooxy)-2-((nitrooxy)methyl)propyl(2S)-2-(6-methoxy(2-naphthyl)) propanoate Fuming nitric acid (90%, 430 μL, 4.2 mmol) was added to ice-cold acetic anhydride (5 mL) and the mixture was stirred in the ice-bath for 5 minutes, then for an additional 5 minutes at ambient temperature. The solution was then added to an ice-cold solution of Example 13a (1.51 g, 4.2 mmol) in EtOAc (20 mL). The reaction was stirred in the ice-bath for 5 minutes then at ambient temperature for 2 hours. A second portion of acetyl nitrate, prepared from fuming nitric acid (90%, 100 μL, 2.4 mmol) in Ac$_2$O (2 mL), was added to the reaction mixture and stirred for an additional 2 hours. The reaction mixture was washed with saturated NaHCO$_3$, water and brine, and dried over Na$_2$SO$_4$, filtered and concentrated. The product was separated by silica gel column chromatography eluting with ethyl acetate/hexane (gradient form 1:3 to 2:3, Rf=0.4 in 1:3) to give the title compound as a white solid (0.79 g, 42% yield). Mp 69-71° C. $^1$H NMR (300 MHz, CDCl$_3$) δ 7.72-7.60 (m, 3H), 7.31-7.24 (m, 1H), 7.18-7.11 (m, 2H), 4.72-4.43 (m, 6H), 3.91 (s, 3H), 3.86 (q, J=7.2 Hz, 1H), 1.58 (d, J=7.2 Hz, 3H). $^{13}$C NMR (75 MHz, CDCl$_3$) δ 172.8, 157.9, 134.1, 133.9, 129.1, 128.8, 127.5, 125.9, 125.5, 119.4, 105.5, 86.2, 67.2, 66.9, 60.9, 55.3, 45.0, 17.6. Mass spectrum (API-TIS) m/z 454.

Example 14

2-(N-(2-(Nitrooxy)ethyl)carbamoyloxy)ethyl(2S)-2-(6-methoxy(2-naphthyl))propanoate 14a. 2-(N-(2-Bromoethyl)carbamoyloxy)ethyl(2S)-2-(6-methoxy(2-naphthyl))-propanoate A solution of (2S)-2-(6-methoxy(2-naphthyl))propanoic acid (naproxen, 0.74 g, 2.2 mmol), p-toluenesulfonic acid monohydrate (10 mg, 0.05 mmol) and 2-bromoethyl isocyanate (1.18 g, 7.9 mmol) in CH$_2$Cl$_2$ (100 mL) was stirred at room temperature for 4 hours. The reaction mixture was washed with saturated NaHCO$_3$ and extracted with CH$_2$Cl$_2$ (100 mL). The combined organic layer was washed with water, brine, dried over Na$_2$SO$_4$, filtered and concentrated. The product was separated by silica gel column chromatography eluting with ethyl acetate/hexane (gradient form 2:3 to 1:1, Rf=0.3 in 2:3) to give the title compound as an oil (1.57 g, 54% yield). $^1$H NMR (300 MHz, CDCl$_3$) δ 7.71-7.66 (m, 3H), 7.42-7.38 (m, 1H), 7.16-7.08 (m, 2H), 5.0 (br, 1H), 4.27-4.19 (m, 4H), 3.89 (s, 3H), 3.88 (q, J=7.2 Hz, 1H), 3.45-3.33 (m, 4H), 1.58 (d, J=7.2 Hz, 3H). $^{13}$C NMR (75 MHz, CDCl$_3$) δ 174.3, 157.5, 155.6, 135.4, 133.5, 129.1 128.7, 126.9, 126.1, 125.9, 118.9, 105.4, 62.6, 62.5, 55.2, 45.2, 42.5, 32.0, 18.3. Mass spectrum (API-TIS) m/z 424 (MH)$^+$.

14b. 2-(N-(2-(Nitrooxy)ethyl)carbamoyloxy)ethyl (2S)-2-(6-methoxy(2-naphthyl))-propanoate A solution of the product of Example 14a (1.57 g, 3.7 mmol) and AgNO$_3$ (7.7 mmol) in acetonitrile (40 mL) was heated to 60° C. for 3 hours. After cooling to ambient temperature, brine (50 mL) was added and the mixture was stirred for 30 minutes. The resulted mixture was filtered through Celite and the filtrate was extracted with CH$_2$Cl$_2$ (100 mL). The organic layer was washed with brine, dried over Na$_2$SO$_4$, filtered, concentrated and dried under vacuum. The product was separated by silica gel column chromatography eluting with ethyl acetate/hexane (1:2, Rf=0.22) to give the title compound. The product was recrystallized from ethyl ether (0.63 g, 41% yield). Mp 56-57° C. $^1$H NMR (300 MHz, CDCl$_3$) δ 7.72-7.66 (m, 3H), 7.42-7.38 (m, 1H), 7.17-7.11 (m, 2H), 4.9 (br, 1H), 4.43 (t, J=5.0 Hz, 2H), 4.27-4.19 (m, 4H), 3.91 (s, 3H), 3.88 (q, J=7.2 Hz, 1H), 3.37 (br. q, 2H), 1.58 (d, J=7.2 Hz, 3H). $^{13}$C NMR (75 MHz, CDCl$_3$) δ 174.3, 157.5, 155.8, 135.3, 133.5, 129.0 128.6, 126.9, 126.0, 125.8, 118.9, 105.4, 71.5, 62.7, 62.4, 55.1, 45.1, 38.0, 18.2. Mass spectrum (API-TIS) m/z 424 (M+NH$_4$)$^+$.

Example 15

3-(2-(Nitrooxy)ethoxy)phenyl(2S)-2-(6-methoxy(2-naphthyl)propanoate 15a. (2-Bromoethyl)nitrooxy Sulfuric acid (14.55 g, 148 mmol) was cooled to 5° C. in an ice-water bath. Fuming nitric acid (90%, 6.2 mL, 9.2 g, 146 mmol) was slowly added while the temperature was maintained at <10° C. The resulting solution was stirred in the ice-water bath for 40 minutes. 2-Bromoethanol (4.8 mL, 8.5 g, 67.7 mmol) was slowly added while maintaining the temperature at <10° C. The reaction mixture was stirred in the ice-water bath for two hours, poured onto ice and extracted with ethyl ether. The organic phase was washed with water (3×), sodium bicarbonate solution (2×) and brine. The organic phase was dried with magnesium sulfate, filtered, and concentrated to give the title compound (10.48 g, 91% yield). $^1$H NMR (300 MHz, CDCl$_3$) δ 4.75 (t, J=6.4 Hz, 2H), 3.55 (t, J=6.4 Hz, 2H). $^{13}$C NMR (75 MHz, CDCl$_3$) δ 71.4, 25.1.

15b. 3-Hydroxyphenyl(2S)-2-(6-methoxy(2-naphthyl)propanoate

To a suspension of ground resorcinol (6.7073 g, 60.915 mmol) in CH$_2$Cl$_2$ (900 mL) was added (2S)-2-(6-methoxy(2-naphthyl))propanoic acid (naproxen, 4.4467 g, 19.311 mmol) and then 1-(3-(dimethylamino) propyl)-3-ethylcarbodiimide hydrochloride (EDAC, 5.3733 g, 28.030 mmol). The reaction mixture was stirred at ambient temperature for 1 hour to give an oil phase and a solution phase. The solution phase was washed with water, brine, dried with magnesium sulfate, filtered and then concentrated. The crude product was purified by chromatography (100% methylene chloride, then 1% methanol/99% methylene chloride, and then 2% methanol/98% methylene chloride) to give a mixture of the desired product and naproxen. The crude product was dissolved in methylene chloride, washed with sodium bicarbonate solution (3×) and brine. The organic phase was dried over magnesium sulfate, filtered and concentrated to give the title compound (804.8 mg, 2.497 mmol, 13% yield). Mp 143-144° C. $^1$H NMR (300 MHz, CDCl$_3$) δ 7.73-7.70 (m, 3H), 7.47 (d, J=8.3 Hz, 1H), 7.16-7.08 (m, 3H), 6.58 (d, J=7.7 Hz, 1H), 6.52 (d, J=7.9 Hz, 1H), 6.43 (s, 1H), 4.06 (q, J=7.0 Hz, 1H), 3.90 (s, 3H), 1.66 (d, J=7.0 Hz, 3H). $^{13}$C NMR (75 MHz, CDCl$_3$) δ 173.43, 157.8, 156.5, 151.7, 135.0, 133.8, 129.9, 129.3, 129.0, 127.4, 126.1, 126.0, 119.1, 113.5, 113.1, 109.0, 105.7, 55.3, 45.6, 18.4. Mass spectrum APIMS (IS, NH$_4$OAc) m/z 323 (M$^+$H$^+$), 340 (M+NH$_4$$^+$), 345 (M+Na$^+$), 662 (2M+NH$_4$$^+$), 984 (3M+NH$_4$$^+$).

15c. 3-(2-(Nitrooxy)ethoxy)phenyl(2S)-2-(6-methoxy(2-naphthyl)propanoate

To a solid mixture of the product of Example 15b (757.4 mg, 2.3495 mmol) and potassium carbonate powder (1.02 g, 7.38 mmol) under argon was added dry acetone (100 mL) and then the product of Example 15a (0.45 mL, 810 mg, 4.76 mmol). The resulting mixture was refluxed for two days and more product of Example 15a (0.45 mL, 810 mg, 4.76 mmol) was added. The reaction mixture was refluxed for one week and filtered. The filtrate was concentrated to dryness. The crude product was treated with methylene chloride and water. The organic phase was dried over magnesium sulfate, concentrated and purified by chromatography twice (100% methylene chloride) and (10% ethyl acetate/90% hexane) to give the title compound (30 mg, 0.073 mmol, 3% yield). Mp 88-91° C. $^1$H NMR (300 MHz, CDCl$_3$) δ 7.77-7.70 (m, 3H), 7.49 (dd, J=8.6 Hz & 1.6 Hz, 1H), 7.26-7.14 (m, 3H), 6.73 (dd, J=8.3 Hz, 2.3 Hz, 1H), 6.63 (dd, J=8.1 Hz, 1.8 Hz, 1H), 6.54-6.52 (m, 1H), 4.75 (t, J=4.5 Hz, 1H), 4.17 (t, J=4.5 Hz, 2H), 4.08 (q, J=7.1 Hz, 2H), 3.92 (s, 3H), 1.69 (d, J=7.2 Hz, 3H). $^{13}$C NMR (75 MHz, CDCl$_3$) δ 173.0, 158.6, 157.7, 151.8, 135.0, 133.8, 129.9, 129.3, 128.9, 127.4, 126.15, 126.06, 119.1, 114.6, 112.0, 108.2, 105.6, 70.7, 64.1, 55.3, 45.5, 18.5. Mass spectrum APIMS (IS, NH$_4$OAc) m/z 412 (M+H$^+$), 429 (M+NH$_4^+$), 434 (M+Na$^+$), 840 (2M+NH$_4^+$).

Example 16

4-(2-(Nitrooxy)ethoxy)phenyl(2S)-2-(6-methoxy(2-naphthyl))propanoate 16a. 4-Hydroxyphenyl(2S)-2-(6-methoxy(2-naphthyl)propanoate To (2S)-2-(6-methoxy(2-naphthyl))propanoic acid (naproxen, 6.14 g, 26.64 mmol) in methylene chloride (300 mL) was added 1,3-dicyclohexylcarbodiimide (2.86 g, 13.84 mmol) in methylene chloride (20 mL). The reaction mixture was stirred at room temperature for 40 minutes and then filtered. The filtrate was added to a stirring suspension of hydroquinone (8.13 g, 73.84 mmol) in methylene chloride (1.6 L). N,N-dimethylaminopyridine (DMAP, 3.071 g, 25.14 mmol) was added. The reaction mixture was stirred at room temperature for 3 days and then filtered. The filtrate was washed with 10% citric acid, brine, sodium bicarbonate solution and brine. The organic phase was dried over magnesium sulfate, filtered, and concentrated. The crude product was purified by chromatography (100% methylene chloride, then gradually increasing the percentage of methanol in methylene chloride from 0.5%, 0.75%, 1%, 2%, 3% to 4%) to give the title compound (1.76 g, 41% yield). Mp 141-142° C. $^1$H NMR (300 MHz, CDCl$_3$) δ 7.75-7.71 (m, 3H), 7.48 (dd, J=8.6 Hz, 1.7 Hz, 1H), 7.17-7.14 (m, 2H), 6.84-6.79 (m, 2H), 6.74-6.68 (d, 2H), 4.07 (q, J=7.1 Hz, 1H), 3.92 (s, 3H), 1.67 (d, J=7.1 Hz, 3H). $^{13}$C NMR (75 MHz, CDCl$_3$) δ 174.0, 157.7, 153.4, 144.2, 135.1, 133.8, 129.3, 129.0, 127.4, 126.11, 126.09, 122.2, 119.1, 115.9, 105.7, 55.3, 45.5, 18.4. Mass spectrum APIMS (IS, NH$_4$OAc) m/z 323 (M+H$^+$), 340 (M+NH$_4^+$), 345 (M+Na$^+$), 662 (2M+NH$_4^+$), 984 (3M+NH$_4^+$).

16b. 4-(2-(Nitrooxy)ethoxy)phenyl(2S)-2-(6-methoxy(2-naphthyl)propanoate

To a solid mixture of the product of Example 16a (1.29 g, 3.99 mmol) and potassium carbonate (1.54 g, 11.11 mmol) under argon was added dry acetone (150 mL) and then the product of Example 15a (0.75 mL, 1.35 g, 7.95 mmol). The reaction was refluxed for two days. More product of Example 15a (0.75 mL, 1.35 g, 7.95 mmol) was added. The reaction mixture was refluxed for ten days and then filtered. The filtrate was concentrated to dryness and treated with methylene chloride and water. The organic layer was dried over magnesium sulfate, filtered, concentrated and purified by chromatography twice (100% methylene chloride) and (10% ethylacetate/90% hexane) to give the title compound (49.2 mg, 3% yield). $^1$H NMR (300 MHz, CDCl$_3$) δ 7.76-7.70 (m, 3H), 7.48 (dd, J=8.6 Hz, 1.7 Hz, 1H), 7.18-7.13 (m, 2H), 6.93-6.88 (m, 2H), 6.84-6.78 (d, 2H), 4.75 (t, J=4.6 Hz, 2H), 4.16 (t, J=4.6 Hz, 2H), 4.07 (q, J=7.1 Hz, 1H), 3.91 (s, 3H), 1.67 (d, J=7.1 Hz, 3H). $^{13}$C NMR (75 MHz, CDCl$_3$) δ 173.4, 157.7, 155.5, 145.0, 135.1, 133.8, 129.3, 128.9, 127.3, 126.09, 126.07, 122.4, 119.9, 115.1, 105.6, 70.8, 64.4, 55.3, 45.5, 18.5. Mass spectrum APIMS (IS, NH$_4$OAc) m/z 412 (M+H$^+$), 429 (M+NH$_4^+$), 434 (M+Na$^+$), 840 (2M+NH$_4^+$).

Example 17

(N-Methyl-N-(2-(nitrooxy)ethyl)carbamoyl)methyl (2S)-2-(6-methoxy(2-naphthyl))propanoate 17a. ((tert-Butyl)oxycarbonyl)methyl(2S)-2-(6-methoxy(2-naphthyl))propanoate A mixture of (2S)-2-(6-methoxy(2-naphthyl))propanoic acid (naproxen, 3 g, 13.0 mmol), NaHCO$_3$ (1.4 g, 16.7 mmol) and tert-butyl bromoacetate (5.08 g, 26.0 mmol) in DMF (30 mL) was stirred at room temperature for 2 days and the solvent was evaporated under high vacuo. The residue was then diluted with CH$_2$Cl$_2$, the solvent removed by filtration and the residue was recrystallized from a mixture of CH$_2$Cl$_2$/EtOAc/Hex to give the title compound as a white solid in quantitative yield. Mp 85-86° C. $^1$H NMR (300 MHz, CDCl$_3$) δ 7.69-7.70 (m, 3H), 7.43 (dd, J=1.6 and 8.6 Hz, 1H), 7.10-7.15 (m, 2H), 4.47 (ABq, J$_{AB}$=15.7 Hz, Δv$_{AB}$=40.7 Hz, 2H), 3.97 (q, J=7.2 Hz, 1H), 3.90 (s, 3H), 1.63 (d, J=7.2 Hz, 3H), 1.42 (s, 9H). $^{13}$C NMR (75 MHz, CDCl$_3$) δ 174.2, 166.9, 157.8, 135.4, 133.9, 129.5, 129.1, 127.3, 126.5, 126.3, 119.1, 105.8, 82.5, 61.7, 55.5, 45.3, 28.1, 18.8. Mass spectrum (API-TIS) m/z 345 (MH$^+$), 362 (MNH$_4^+$).

17b. 2-((2S)-2-(6-Methoxy(2-naphthyl))propanoyloxy)acetic acid

Trifluoroacetic acid (8.4 mL) was added drop-wise to a solution of the product of Example 17a (4.8 g, 14 mmol) in CH$_2$Cl$_2$ (20 mL). The reaction mixture was stirred at room temperature for 2 days and the volatile material removed in vacuo. The residue after evaporation was recrystallized from EtOAc/Hex to give the title compound (2.7 g, 66% yield) as a white solid. Mp 122-123° C. $^1$H NMR (300 MHz, CDCl$_3$) δ 7.67-7.73 (m, 3H), 7.42 (d, J=9.1 Hz, 1H), 7.12-7.17 (m, 2H), 4.65 (ABq, J$_{AB}$=16.4 Hz, Δv$_{AB}$=34.3 Hz, 2H), 3.98 (q, J=7.1 Hz, 1H), 3.92 (s, 3H), 1.63 (d, J=7.1 Hz, 3H). $^{13}$C NMR (75 MHz, CDCl$_3$) δ 174.2, 173.0, 157.9, 135.1, 133.9, 129.5, 129.1, 127.4, 126.4, 126.3, 119.2, 105.8, 60.5, 55.5, 45.2, 18.7. Mass spectrum (API-TIS) m/z 289 (MH$^+$), 306 (MNH$_4^+$).

17c. Methyl(2-(nitrooxy)ethyl)ammonium nitrate

Methyl(2-(hydroxy)ethyl)amine (1.5 g, 20 mmol) in EtOAc (65 mL) was added drop-wise to a mixture of fuming HNO$_3$ (6.3 g, 4.2 mL, 100 mmol) and Ac$_2$O (16.3 g, 15.1 mL, 160 mmol) at -10° C. The reaction mixture was stirred at -10° C. for 30 minutes and diluted with EtOAc and hexane. The precipitate was collected by filtration and washed with hexane to give the title compound (2.79 g, 82% yield) as an off-white solid. Mp 58-62° C. $^1$H NMR (300 MHz, d$_6$-DMSO) δ 4.59-4.67 (m, 2H), 4.64-4.73 (m, 2H), 2.61 (bs, 3H). $^{13}$C NMR (75 MHz, d$_6$-DMSO) δ 59.8, 38.7, 24.4. Mass spectrum (API-TIS) m/z 121 (MH$^+$).

17d. (N-Methyl-N-(2-(nitrooxy)ethyl)carbamoyl)methyl(2S)-2-(6-methoxy(2-naphthyl))propanoate A mixture of the product of Example 17b (1.03 g, 3.57 mmol), the product of Example 17c (0.72 g, 3.93 mmol) and N,N-dimethylaminopyridine (DMAP, 0.44 g, 3.57 mmol) in CH$_2$Cl$_2$ (20 mL) at 0° C. was treated with 1-(3-(dimethylamino)propyl)-3-ethylcarbodiimide hydrochloride (0.75 g, 3.93 mmol). The reaction mixture was stirred at 0° C. for 3 hours, diluted with more CH$_2$Cl$_2$, washed with water, brine and dried over Na$_2$SO$_4$. The residue after filtration and evaporation was chromatographed on silica gel eluting with 1:3 to 1:2 to 1:1 EtOAc:Hex to give the title compound (0.71 g, 51% yield). Mp 80-81° C. $^1$H NMR (300 MHz, CDCl$_3$) δ 7.67-7.74 (m, 3H), 7.45 (dd, J=1.5 and 8.5 Hz, 1H), 7.08-7.18 (m, 2H), 4.70 (ABq, J$_{AB}$=14.5 Hz, Δv$_{AB}$=58.2 Hz, 2H), 4.53-4.67 (m, 2H), 4.02 (q, J=7.1 Hz, 1H), 3.92 (s, 3H), 3.56-3.77 (m, 2H), 2.97 (s, 3H), 1.65 (d, J=7.2 Hz, 3H). $^{13}$C NMR (75 MHz, CDCl$_3$) δ 174.4, 167.1, 157.8, 135.3, 133.9, 129.4, 129.0, 127.3, 126.4, 126.3, 119.1, 105.7, 71.3, 61.7, 55.4, 46.3, 45.3, 36.0, 18.7. Mass spectrum (API-TIS) m/z 391 (MH$^+$), 408 (MNH$_4^+$). Anal. calcd. for C$_{19}$H$_{22}$N$_2$O$_7$: C, 58.46; H, 5.68; N, 7.18. Found: C, 58.32; H, 5.55; N, 6.94.

Example 18

(N-Ethyl-N-(2-(nitrooxy)ethyl)carbamoyl)methyl
(2S)-2-(6-methoxy(2-naphthyl))propanoate 18a. Ethyl(2-(nitrooxy)ethyl)ammonium nitrate Ethyl(2-(hydroxy)ethyl)amine (5 g, 56 mmol) in EtOAc (60 mL) was added drop-wise to a mixture of fuming HNO$_3$ (17.7 g, 11.8 mL, 280 mmol) and Ac$_2$O (45.8 g, 42.3 mL, 448 mmol) at –10° C. The reaction mixture was stirred at –10° C. for 30 minutes and diluted with EtOAc and hexane. The oil layer was separated and dried in high vacuo to give the title compound (8.4 g, 76% yield) as a pale green oil. $^1$H NMR (300 MHz, d$_6$-DMSO) δ 8.60-8.95 (bs, 2H), 4.84 (m, 2H), 3.37-3.49 (m, 2H), 3.02-3.16 (m, 2H), 1.24 (t, J=7.2 Hz, 3H). $^{13}$C NMR (75 MHz, d$_6$-DMSO) δ 69.1, 43.6, 42.6, 11.0. Mass spectrum (API-TIS) m/z 135 (MH$^+$).

18b. (N-Ethyl-N-(2-(nitrooxy)ethyl)carbamoyl)methyl(2S)-2-(6-methoxy(2-naphthyl))propanoate A mixture of the product of Example 17b (1.0 g, 3.47 mmol), the product of Example 18a (0.75 g, 3.82 mmol) and N,N-dimethylaminopyridine (DMAP, 0.42 g, 3.47 mmol) in CH$_2$Cl$_2$ (20 mL) at 0° C. was treated with 1-(3-(dimethylamino)propyl)-3-ethylcarbodiimide hydrochloride (0.73 g, 3.82 mmol). The reaction mixture was stirred at 0° C. for 3 hours, diluted with more CH$_2$Cl$_2$, washed with water, brine and dried over Na$_2$SO$_4$. The residue after filtration and evaporation was chromatographed on silica gel eluting with 1:2 to 1:1 EtOAc:Hex to give the title compound (0.4 g, 29% yield). Mp 60-61° C. $^1$H NMR (300 MHz, CDCl$_3$) δ 7.65-7.74 (m, 3H), 7.44 (dd, J=1.5 and 8.5 Hz, 1H), 7.06-7.17 (m, 2H), 4.70 (ABq, J$_{AB}$=14.4 Hz, Δv$_{AB}$=64.9 Hz, 2H), 4.54-4.65 (m, 2H), 4.01 (q, J=7.1 Hz, 1H), 3.91 (s, 3H), 3.50-3.72 (m, 2H), 3.26 (q, J=7.2 Hz, 2H), 1.64 (d, J=7.2 Hz, 3H), 1.17 (t, J=7.1 Hz, 3H). $^{13}$C NMR (75 MHz, CDCl$_3$) δ 174.5, 166.9, 157.8, 135.3, 133.9, 129.4, 129.0, 127.3, 126.4, 126.3, 119.1, 105.7, 71.0, 61.5, 55.4, 45.3, 43.9, 43.3, 18.7, 14.0. Mass spectrum (API-TIS) m/z 405 (MH$^+$), 422 (MNH$_4^+$). Anal. calcd. for C$_{20}$H$_{24}$N$_2$O$_7$: C, 59.40; H, 5.98; N, 6.93. Found: C, 59.28; H, 5.81; N, 6.70.

Example 19

2-(4-((Nitrooxy)methyl)piperidyl)-2-oxoethyl(2S)-2-(6-methoxy(2-naphthyl))propanoate 19a. Nitrooxy(4-piperidylmethyl)hydrogen nitrate 4-Piperidylmethan-1-ol (2.5 g, 21.7 mmol) in a mixture of EtOAc (25 mL) and CH$_2$Cl$_2$ (5 mL) was added drop-wise to a mixture of fuming HNO$_3$ (6.83 g, 4.6 mL, 109 mmol) and Ac$_2$O (17.7 g, 16.3 mL, 174 mmol) at –10° C. The reaction mixture was stirred at –10° C. for 30 minutes and diluted with EtOAc and hexane. The precipitate was collected by filtration and washed with hexane to give the title compound (2.5 g, 52% yield) as a pale green solid. Mp 51-53° C. $^1$H NMR (300 MHz, d$_6$-DMSO) δ 8.45-8.75 (bs, 1H), 8.10-8.40 (bs, 1H), 4.44 (d, J=6.4 Hz, 2H), 3.22-3.35 (m, 2H), 2.80-2.98 (m, 2H), 1.96-2.15 (m, 1H), 1.75-1.89 (m, 2H), 1.40-1.52 (m, 2H). $^{13}$C NMR (75 MHz, d$_6$-DMSO) δ 76.4, 42.7, 31.2, 24.9. Mass spectrum (API-TIS) m/z 161 (MH$^+$). Anal. calcd. for C$_6$H$_{13}$N$_3$O$_6$: C, 32.29; H, 5.87; N, 18.83. Found: C, 32.03; H, 5.78; N, 18.73.

19b. 2-(4-((Nitrooxy)methyl)piperidyl)-2-oxoethyl
(2S)-2-(6-methoxy(2-naphthyl))propanoate A mixture of the product of Example 17b (1.5 g, 5.21 mmol), the product of Example 19a (1.16 g, 5.21 mmol) and N,N-dimethylaminopyridine (DMAP, 0.63 g, 5.21 mmol) in CH$_2$Cl$_2$ (30 mL) at 0° C. was treated with 1-(3-(dimethylamino)propyl)-3-ethylcarbodiimide hydrochloride (1.0 g, 5.21 mmol). The reaction mixture was stirred at 0° C. for 3 hours, diluted with CH$_2$Cl$_2$, washed with water, brine and dried over Na$_2$SO$_4$. The residue after filtration and evaporation was chromatographed on silica gel eluting with 1:2 to 1:1 EtOAc:Hex to give the title compound (1.74 g, 78% yield) as a white solid. Mp 94-95° C. $^1$H NMR (300 MHz, d$_6$-DMSO) δ 7.75-7.82 (m, 3H), 7.44 (dd, J=1.3 and 8.5 Hz, 1H), 7.30 (d, J=2.5 Hz, 1H), 7.16 (dd, J=2.5 and 8.9 Hz, 1H), 4.65-4.89 (m, 2H), 4.35 (bd, J=6.4 Hz, 2H), 4.21-4.32 (m, 1H), 4.01 (q, J=7.1 Hz, 1H), 3.86 (s, 3H), 3.55-3.73 (m, 1H), 2.81-3.02 (m, 1H), 2.45-2.63 (m, 1H), 1.87-2.03 (m, 1H), 1.55-1.72 (m, 2H), 1.51 (d, J=7.1 Hz, 3H), 0.90-1.22 (m, 2H). $^{13}$C NMR (75 MHz, d$_6$-DMSO) δ 173.5, 164.3, 157.2, 135.5, 133.3, 129.1, 128.4, 126.9, 126.5, 125.8, 118.7, 105.6, 76.9, 61.8, 55.1, 44.3, 43.2, 33.2, 28.2, 27.5, 18.6. Mass spectrum (API-TIS) m/z 431 (MH$^+$), 448 (MNH$_4^+$). Anal. calcd. for C$_{22}$H$_{26}$N$_2$O$_7$: C, 61.39; H, 6.09; N, 6.51. Found: C, 61.24; H, 5.98; N, 6.40.

Example 20

(N-Methyl-N-(((2-(nitrooxy)ethyl)oxycarbonyl)methyl)carbamoyl)methyl(2S)-2-(6-methoxy(2-naphthyl))propanoate 20a. (N-(((tert-Butyl)oxycarbonyl)methyl)-N-methylcarbamoyl)methyl(2S)-2-(6-methoxy(2-naphthyl))
propanoate A mixture of the product of Example 17b (10 g, 34.7 mmol), sarcosine tert-butyl ester hydrochloride (6.3 g, 34.7 mmol) and N,N-dimethylaminopyridine (DMAP, 4.24 g, 34.7 mmol) in CH$_2$Cl$_2$ (125 mL) at 0° C. was treated with 1-(3-(dimethylamino)propyl)-3-ethylcarbodiimide hydrochloride (6.7 g, 34.7 mmol). The reaction mixture was stirred at room temperature for 16 hours, diluted with CH$_2$Cl$_2$, washed with water, brine and dried over Na$_2$SO$_4$. The residue after filtration and evaporation was chromatographed on silica gel eluting with 1:9 to 1:1 EtOAc:hexane to give the title compound (11.8 g, 82% yield) as a white solid. Mp 103-104° C. $^1$H NMR (300 MHz, CDCl$_3$) δ 7.65-7.77 (m, 3H), 7.44 (dd, J=1.3 and 8.9 Hz, 1H), 7.03-7.18 (m, 2H), 4.74 (ABq, J$_{AB}$=14.5 Hz, Δv$_{AB}$=64.7 Hz, 2H), 3.72-4.19 (m, 3H), 3.90 (s, 3H), 2.93 (s, 3H), 1.63 (d, J=7.1 Hz, 3H), 1.45 (s, 9H). $^{13}$C NMR (75 MHz, CDCl$_3$) δ 174.3, 168.0, 167.1, 157.8, 135.5, 133.9, 129.5, 129.1, 127.3, 126.5, 126.3, 119.0, 105.8, 82.2, 61.5, 55.4, 51.6, 45.3, 35.3, 28.2, 18.8. Mass spectrum (API-TIS) m/z 416 (MH$^+$), 433 (MNH$_4^+$), 438 (MNa$^+$).

20b. 2-(2-((2S)-2-(6-Methoxy(2-naphthyl))propanoyloxy)-N-methylacetylamino)acetic acid Trifluoroacetic acid (5 mL) was added drop-wise to a solution of the product of Example 20a (3.54 g, 8.5 mmol) in CH$_2$Cl$_2$ (15 mL). The reaction mixture was stirred at room temperature for 24 hours and the volatile material removed in vacuo. The residue, after evaporation, was recrystallized from CH$_2$Cl$_2$/EtOAc/hexane to give the title compound (2.55 g, 83% yield) as a white solid. Mp 174-175° C. $^1$H NMR (300 MHz, d$_6$-DMSO) δ 7.76-7.80 (m, 3H), 7.42-7.45 (m, 1H), 7.27-7.29 (m, 1H), 7.15 (dd, J=2.5 and 8.5 Hz, 1H), 4.84 (ABq, J$_{AB}$=15.1 Hz, Δν$_{AB}$=26.9 Hz, 2H), 3.93-4.12 (m, 3H), 3.87 (s, 3H), 2.94 (s, 3H), 1.51 (d, J=7.1 Hz, 3H). $^{13}$C NMR (75 MHz, d$_6$-DMSO) δ 173.4, 170.5, 166.6, 157.2, 135.5, 133.3, 129.2, 128.4, 126.9, 126.5, 125.8, 118.7, 105.8, 61.4, 55.2, 48.9, 44.3, 34.5, 18.7. Mass spectrum (API-TIS) m/z 360 (MH$^+$), 377 (MNH$_4^+$), 382 (MNa$^+$). Anal. calcd. for C$_{19}$H$_{21}$NO$_6$: C, 63.50; H, 5.89; N, 3.90. Found: C, 63.33; H, 5.90; N, 3.89.

20c. (N-(((2-Hydroxyethyl)oxycarbonyl)methyl)-N-methylcarbamoyl)methyl(2S)-2-(6-methoxy(2-naphthyl))propanoate To a solution of the product of Example 20b (0.5 g, 1.4 mmol), N,N-dimethyl aminopyridine (DMAP, 84.9 mg, 0.69 mmol) and ethylene glycol (1.6 g, 27.8 mmol) in CH$_2$Cl$_2$ (4 mL) was added drop-wise a solution of DCC (0.36 g, 1.7 mmol) in CH$_2$Cl$_2$ (2 mL). The reaction mixture was stirred at room temperature for 16 hours. The precipitate was filtered. The residue after evaporation of the solvent was redissolved in EtOAc, washed with water, brine and dried over Na$_2$SO$_4$. The residue after filtration and evaporation was chromatographed on silica gel eluting with 1:1:0.1 EtOAc:hexane:MeOH to give the title product (0.4 g, 71% yield) as a white solid. Mp 113-114° C. $^1$H NMR (300 MHz, CDCl$_3$) δ 7.67-7.73 (m, 3H), 7.44 (dd, J=1.6 and 8.6 Hz, 1H), 7.11-7.15 (m, 2H), 4.74 (ABq, J$_{AB}$=14.6 Hz, Δν$_{AB}$=55.9 Hz, 2H), 4.22-4.31 (m, 2H), 4.09-4.12 (bs, 2H), 4.01 (q, J=7.2 Hz, 1H), 3.90 (s, 3H), 3.74-3.83 (m, 2H), 2.99 (s, 3H), 2.40 (bs, 1H), 1.64 (d, J=7.2 Hz, 3H). $^{13}$C NMR (75 MHz, CDCl$_3$) δ 174.6, 168.9, 167.6, 157.8, 135.3, 133.9, 129.4, 129.0, 127.3, 126.5, 126.3, 119.1, 105.8, 67.1, 61.6, 60.9, 55.4, 50.2, 45.3, 35.5, 18.6. Mass spectrum (API-TIS) m/z 404 (MH$^+$), 421 (MNH$_4^+$). Anal. calcd. for C$_{21}$H$_{25}$NO$_7$•1 mol H$_2$O: C, 59.85; H, 6.46; N, 3.32. Found: C, 59.94; H, 6.15; N, 3.39.

20d. (N-Methyl-N-(((2-(nitrooxy)ethyl)oxycarbonyl)methyl)carbamoyl)methyl(2S)-2-(6-methoxy(2-naphthyl))propanoate A suspension of the product of Example 20c (0.26 g, 0.64 mmol) in EtOAc (0.28 mL) was added drop-wise to a mixture of fuming HNO$_3$ (61.3 mg, 41 μL, 0.97 mmol) and Ac$_2$O (148 mg, 137 μL, 1.45 mmol) at 0° C. The reaction mixture was stirred at 0° C. for 3 hours. Then an additional ice cold mixture of fuming HNO$_3$ (61.3 mg, 41 μL, 0.97 mmol) and Ac$_2$O (148 mg, 137 μL, 1.45 mmol) was added drop-wise to the reaction mixture at 0° C. The stirring was continued for another 2 hours. The reaction mixture was diluted with EtOAc and washed with ice cold saturated NaHCO$_3$, water and dried over Na$_2$SO$_4$. The residue after filtration and evaporation was chromatographed on silica gel eluting with 1:1:0.1 EtOAc:hexane:MeOH to give the title compound (0.2 g, 69% yield) as a white solid. Mp 71-73° C. $^1$H NMR (300 MHz, CDCl$_3$) δ 7.66-7.75 (m, 3H), 7.44 (dd, J=1.6 and 8.5 Hz, 1H), 7.08-7.17 (m, 2H), 4.76 (ABq, J$_{AB}$=14.6 Hz, Δν$_{AB}$=59.7 Hz, 2H), 4.64-4.69 (m, 2H), 4.39-4.42 (m, 2H), 4.14 (ABq, J$_{AB}$=17.4 Hz, Δν$_{AB}$=32.0 Hz, 2H), 3.93-4.07 (m, 1H), 3.91 (s, 3H), 2.98 (s, 3H), 1.64 (d, J=7.2 Hz, 3H). $^{13}$C NMR (75 MHz, CDCl$_3$) δ 174.3, 168.6, 167.4, 157.8, 135.4, 133.9, 129.5, 129.0, 127.3, 126.5, 126.3, 119.1, 105.7, 70.2, 61.5, 61.1, 55.4, 49.5, 45.3, 35.3, 18.7. Mass spectrum (API-TIS) m/z 449 (MH$^+$), 466 (MNH$_4^+$). Anal. calcd. for C$_{21}$H$_{24}$N$_2$O$_9$: C, 56.25; H, 5.39; N, 6.25. Found: C, 56.00; H, 5.17; N, 6.09.

Example 21

(N-Methyl-N-(((3-(nitrooxy)propyl)oxycarbonyl)methyl)carbamoyl)methyl(2S)-2-(6-methoxy(2-naphthyl))propanoate

21a. (N-(((3-Hydroxypropyl)oxycarbonyl)methyl)-N-methylcarbamoyl)methyl(2S)-2-(6-methoxy(2-naphthyl))propanoate To a solution of the product of Example 20b (0.5 g, 1.4 mmol), N,N-dimethylaminopyridine (DMAP, 84.9 mg, 0.69 mmol) and 1,3-propanediol (2.1 g, 27.8 mmol) in CH$_2$Cl$_2$ (4 mL) was added drop-wise a solution of DCC (0.36 g, 1.7 mmol) in CH$_2$Cl$_2$ (2 mL). The reaction mixture was stirred at room temperature for 16 hours. The precipitate was filtered. The residue after evaporation of the solvent was redissolved in EtOAc, washed with water, brine and dried over Na$_2$SO$_4$, filtered and evaporated. The residue was chromatographed on silica gel eluting with 1:1:0.1 EtOAc:hexane:MeOH to give the product (0.35 g, 60% yield) as a white solid. Mp 80-82° C. $^1$H NMR (300 MHz, CDCl$_3$) δ 7.40-7.73 (m, 3H), 7.43 (dd, J=1.5 and 8.6 Hz, 1H), 7.07-7.15 (m, 2H), 4.75 (ABq, J$_{AB}$=14.6 Hz, Δν$_{AB}$=57.7 Hz, 2H), 4.28 (t, J=5.9 Hz, 2H), 3.95-4.20 (m, 3H), 3.90 (s, 3H), 3.61-3.72 (m, 2H), 2.97 (s, 3H), 1.78-2.00 (m, 3H), 1.63 (d, J=7.2 Hz, 3H). $^{13}$C NMR (75 MHz, CDCl$_3$) δ 174.4, 169.1, 167.3, 157.8, 135.3, 133.8, 129.4, 129.0, 127.2, 126.4, 126.2, 119.0, 105.7, 62.4, 61.5, 59.0, 55.4, 49.8, 45.2, 35.3, 31.6, 18.7. Mass spectrum (API-TIS) m/z 418 (MH$^+$), 435 (MNH$_4^+$), 440 (MNa$^+$). Anal. calcd. for C$_{22}$H$_{27}$NO$_7$•¼ mol H$_2$O: C, 62.62; H, 6.58; N, 3.32. Found: C, 62.35; H, 6.47; N, 3.44.

21b. (N-Methyl-N-(((3-(nitrooxy)propyl)oxycarbonyl)methyl)carbamoyl)methyl(2S)-2-(6-methoxy(2-naphthyl))propanoate A suspension of the product of Example 21a (355 mg, 0.85 mmol) in EtOAc (7.6 mL) was added drop-wise to a mixture of fuming HNO$_3$ (80.9 mg, 54 μL, 1.28 mmol) and Ac$_2$O (196 mg, 181 μL, 1.92 mmol) at 0° C. The reaction mixture was stirred at 0° C. for 1.5 hours. Then an additional ice cold mixture of fuming HNO$_3$ (80.9 mg, 54 μL, 1.28 mmol) and Ac$_2$O (196 mg, 181 μL, 1.92 mmol) was added drop-wise to the reaction mixture at 0° C. The stirring was continued for an additional hour. The reaction mixture was diluted with EtOAc and washed with ice cold saturated NaHCO$_3$, water and dried over Na$_2$SO$_4$. The residue after filtration and evaporation was chromatographed on silica gel eluting with 1:1:0.1 EtOAc:hexane:MeOH to give the title compound (0.34 g, 86% yield) as a white solid. Mp 41-43° C. $^1$H NMR (300 MHz, CDCl$_3$) δ 7.60-7.73 (m, 3H), 7.45 (dd, J=1.7 and 8.6 Hz, 1H), 7.09-7.17 (m, 2H), 4.76 (ABq, J$_{AB}$=14.6 Hz, Δν$_{AB}$=59.0 Hz, 2H), 4.52 (t, J=6.2 Hz, 2H), 4.24 (t, J=6.0 Hz, 2H), 4.10 (ABq, $J_{AB}$=17.4 Hz, $\Delta v_{AB}$=30.4 Hz, 2H), 3.93-4.04 (m, 1H), 3.91 (s, 3H), 2.98 (s, 3H), 2.02-2.11 (m, 2H), 1.64 (d, J=7.2 Hz, 3H). $^{13}$C NMR (75 MHz, CDCl$_3$) δ 174.3, 168.8, 167.4, 157.7, 135.4, 133.8, 129.4, 129.0, 127.3, 126.5, 126.3, 119.1, 105.7, 69.9, 61.5, 61.3, 55.4, 49.7, 45.3, 35.3, 26.4, 18.7. Mass spectrum (API-TIS) m/z 463 (MH$^+$), 480 (MNH$_4^+$). Anal. calcd. for C$_{22}$H$_{26}$N$_2$O$_9$: C, 57.14; H, 5.67; N, 6.06. Found: C, 56.91; H, 5.86; N, 6.02.

Example 22

(N-Methyl-N-((N-(2-(nitrooxy)ethyl)carbamoyl)methyl)carbamoyl)methyl(2S)-2-(6-methoxy(2-naphthyl))propanoate 22a. 2-(Nitrooxy)ethylammonium nitrate 2-Hydroxyethylamine (5 g, 81.9 mmol) in EtOAc (40 mL) was added drop-wise to a mixture of fuming HNO$_3$ (18 g, 12 mL, 0.29 mol) and Ac$_2$O (54 g, 50 mL, 0.53 mol) at −10° C. The reaction mixture was stirred at 0° C. for 10 minutes and at room temperature for 10 minutes. The solvent was evaporated in high vacuo at 40° C. The residue was sonicated with ether. The solid was filtered and washed with hexane to give the title compound as a white solid. Mp 92-94° C. $^1$H NMR (300 MHz, d$_6$-DMSO) δ 7.71-8.25 (bs, 3H), 4.72 (t, J=5.0 Hz, 2H), 3.23 (d, J=5.0 Hz, 2H). $^{13}$C NMR (75 MHz, d$_6$-DMSO) δ 70.9, 37.4.

22b. (N-Methyl-N-((N-(2-(nitrooxy)ethyl)carbamoyl)methyl)carbamoyl)methyl(2S)-2-(6-methoxy(2-naphthyl))propanoate A mixture of the product of Example 20b (0.5 g, 1.39 mmol), the product of Example 22a (0.26 g, 1.53 mmol) and N,N-dimethylaminopyridine (DMAP, 0.17 g, 1.39 mmol) in CH$_2$Cl$_2$ (8 mL) at 0° C. was treated with 1-(3-(dimethylamino)propyl)-3-ethylcarbodiimide hydrochloride (0.29 g, 1.53 mmol). The reaction mixture was stirred at 0° C. for 3 hours, diluted with CH$_2$Cl$_2$, washed with water, brine and dried over Na$_2$SO$_4$. The residue after filtration and evaporation was chromatographed on silica gel eluting with 1:2 EtOAc:hexane to 1:1:0.1 EtOAc:hexane:MeOH to give the title compound (0.61 g, 89% yield) as a white solid. Mp 79-81° C. $^1$H NMR (300 MHz, CDCl$_3$) δ 7.67-7.75 (m, 3H), 7.35-7.45 (m, 1H), 7.07-7.17 (m, 2H), 6.53-6.60 (bs, 1H), 4.68 (ABq, $J_{AB}$=14.3 Hz, $\Delta v_{AB}$=39.6 Hz, 2H), 4.47 (t, J=5.3 HZ, 2H), 3.93-4.07 (m, 3H), 3.91 (s, 3H), 3.46-3.58 (m, 2H), 3.01 (bs, 3H), 1.63 (d, J=7.1 Hz, 3H). $^{13}$C NMR (75 MHz, CDCl$_3$) δ 175.0, 168.9, 167.9, 157.9, 135.2, 133.9, 129.4, 129.0, 127.3, 126.4, 126.3, 119.2, 105.8, 71.3, 61.6, 55.4, 52.3, 45.2, 37.0, 35.8, 18.6. Mass spectrum (API-TIS) m/z 448 (MH$^+$), 465 (MNH$_4$).

Example 23

((2-(Nitrooxy)ethyl)oxycarbonyl)methyl 2-(6-methoxy-2-naphthyl)propanoate 23a. ((2-Hydroxyethyl)oxycarbonyl)methyl 2-(6-methoxy-2-naphthyl)propanoate The product of Example 17b (1.48 g, 5.1 mmol), ethylene glycol (1.52 mL, 25.7 mmol), and N,N-dimethylaminopyridine (DMAP, 124.1 mg, 1.0 mmol) were dissolved in 20 mL of CH$_2$Cl$_2$ and a solution of 1-(3-(dimethylamino)propyl)-3-ethylcarbodiimide hydrochloride (EDAC, 1.17 g, 6.2 mmol) in 10 mL of CH$_2$Cl$_2$ was added. The mixture was stirred at room temperature for 4.5 hours. Aqueous work-up followed by drying over MgSO$_4$ and removal of the solvent under reduced pressure gave a white solid (1.7 g) which was purified via column chromatography on silica gel eluting with 2:1 hexanes/EtOAc. Recrystallization from CH$_2$Cl$_2$/hexanes gave the title compound (1.2 g, 68% yield) as a white solid. Mp 87-90° C. $^1$H NMR (300 MHz, CDCl$_3$); δ7.73-7.70 (m, 3H), 7.43 (dd, J=1.8 Hz, 8.5), 1H), 7.41-7.16 (m, 2H), 4.63 (d, J=2.3 Hz, 2H), 4.24-4.21 (m, 2H), 3.98 (q, J=7.2 Hz, 1H), 3.91 (s, 3H), 3.71-3.69 (m, 2H), 1.63 (d, J=7.2 Hz, 3H); Mass spectrum (API-TIS) m/z 350 (M+18)

23b. ((2-(Nitrooxy)ethyl)oxycarbonyl)methyl 2-(6-methoxy-2-naphthyl)propanoate

Acetic anhydride (742.2 μl, 8.0 mmol) was cooled to 0° C. and fuming nitric acid (90%, 244.2 μL, 5.2 mmol) was added. The mixture was stirred for 20 minutes at 0° C. The fuming nitric acid/acetic anhydride mixture was rapidly added drop-wise to a solution of the product of Example 23a (1.2 g, 3.5 mmol) dissolved in EtOAc (15 mL) at 0° C. and the resulting mixture was stirred at 0° C. for 3 hours. The mixture was allowed to warm to room temperature and saturated NaHCO$_3$ was added. The organics were separated and the aqueous portion extracted with EtOAc. The combined organic extracts were washed with brine, and dried over MgSO$_4$. The sample was filtered through a silica gel plug eluting with 2:1 hexanes/EtOAc to give the title compound (882.6 mg, 74% yield) as a yellow oil which solidified on standing. Mp 44-45° C. $^1$H NMR (300 MHz, CDCl$_3$); δ 7.72-7.69 (m, 3H), 7.42 (dd, J=1.8, 8.5 Hz, 1H), 7.16-7.10 (m, 2H), 4.62 (d, J=5.8 Hz, 2H), 4.57-4.53 (m, 2H), 4.38-4.43 (m, 2H), 3.98 (q, J=7.2 Hz, 1H), 3.91 (s, 3H), 1.63 (d, J=7.2 Hz, 3H). Mass spectrum (API-TIS) m/z 378 (MH$^+$)

Example 24

(N-(3-(Nitrooxy)propyl)carbamoyl)methyl 2-(6-methoxy-2-naphthyl)propanoate

The product of Example 17b (1.7 g, 5.9 mmol), the product of Example 7c (1.3 g, 7.1 mmol), Et$_3$N (2.6 mL, 18.9 mmol) and N,N-dimethylaminopyridine (DMAP, 142.7 mg, 1.2 mmol) were dissolved in CH$_2$Cl$_2$ (30 mL) and a solution of 1-(3-(dimethylamino) propyl)-3-ethylcarbodiimide hydrochloride (EDAC, 1.4 g, 7.1 mmol) in 5 mL CH$_2$Cl$_2$ was added drop-wise. The mixture was stirred at room temperature overnight. The sample was washed with H$_2$O (35 mL), 1N HCl (3 mL), and brine, and dried over MgSO$_4$. The solvent was removed under reduced pressure to give a yellow oil (2.1 g). The oil was purified via column chromatography on silica gel eluting with 1:1 hexanes/EtOAc to give a beige solid. Trituration in Et$_2$O gave the title compound as a beige solid (861.3 mg, 37% yield). Mp 51-53° C. $^1$H NMR (300 MHz, CDCl$_3$); δ 7.77-7.71 (m, 3H), 7.41 (dd, J=1.8, 8.5 Hz, 1H), 7.19 (dd, J=2.5, 8.9, 1H), 7.14 (d, J=2.5 Hz, 2H), 5.29-5.24 (m, 1H), 4.80 (d, J=15.6 Hz, 1H), 4.33 (d, J=15.6 Hz, 1H), 4.36-4.05 (m, 2H), 3.96 (q, J=7.1 Hz, 1H), 3.93 (s, 3H), 2.95-2.78 (m, 2H), 1.64 (d, J=7.1 Hz, 3H), 1.39-1.31 (m, 2H). Mass spectrum (API-TIS) m/z 391 (MH$^+$)

Example 25

((2-((2-(nitrooxy)ethyl)sulfonyl)ethyl)oxycarbonyl)methyl 2-(6-methoxy-2-naphthyl)propanoate 25a. ((2-(2-Hydroxyethylthio)ethyl)oxycarbonyl)methyl 2-(6-methoxy-2-naphthyl)propanoate The product of Example 17b (1.02 g, 66.4 mmol), 2,2'-thiodiethanol (1.76 mL, 17.7 mmol) and N,N-dimethylaminopyridine (DMAP, 85.5 mg, 0.71 mmol) were dissolved in 10 mL CH$_2$Cl$_2$ and a solution of 1-(3-(dimethylamino)propyl)-3-ethylcarbodiimide hydrochloride (EDAC, 810.4 mg, 4.24 mmol) in 5 mL of CH$_2$Cl$_2$ was added. The mixture was allowed to stir overnight. Aqueous work-up followed by drying over MgSO$_4$ and removal of the solvent under reduced pressure gave a yellow oil (1.65 g) which was purified via column chromatography on silica gel eluting with 2:1 hexanes/EtOAc to give the product as a white solid (1.0 g, 75% yield). $^1$H NMR (300 MHz, CDCl$_3$); δ 7.72-7.69 (m, 3H), 7.43 (dd, J=1.6, 8.4 Hz, 1H), 7.16-7.11 (m, 2H), 4.61 (d, J=6.0 Hz, 2H), 4.24 (t, J=6.9 Hz, 2H), 3.98 (q, J=7.1 Hz, 1H), 3.90 (s, 3H), 3.69 (t, J=6.0 Hz, 2H), 2.69-2.09 (m, 2H), 1.62 (d, J=7.1 Hz, 3H). Mass spectrum (API-TIS) m/z 391 (MH$^+$).

25b. ((2-((2-Hydroxyethyl)sulfonyl)ethyl)oxycarbonyl)methyl 2-(6-methoxy-2-naphthyl)propanoate The product of Example 25a (1.03 g, 2.62 mmol) was dissolved in CH$_2$Cl$_2$ (25 mL) and cooled to 0° C. OXONE® (3.23 g, 5.25 mmol) was added and the mixture was stirred at 0° C. for 3 hours and warmed to room temperature. Additional OXONE® was added (6.05 g, 2.3 μmol) and the mixture stirred at room temperature for 6 hours. Aqueous work-up followed by removal of the solvent under reduced pressure and recrystallization of the residue from CH$_2$Cl$_2$/hexanes gave the title compound as off-white crystals (43.9 mg, 40% yield). $^1$H NMR (300 MHz, CDCl$_3$); δ 7.74-7.68 (m, 3H), 7.41 (dd, J=1.8, 8.5 Hz, 1H), 7.17-7.12 (m, 2H), 4.62 (br s, 2H), 4.57, (t, J=5.7 Hz, 2H), 4.03 (t, J=5.1 Hz, 2H), 3.96 (q, J=7.1 Hz, 1H), 3.91 (s, 3H), 3.37-3.33 (br t, 2H), 2.11 (t, J=5.1 Hz, 2H), 1.62 (d, J=7.1 Hz, 3H); Mass spectrum (API-TIS) m/z 442 (M+18)

25c. ((2-((2-(nitrooxy)ethyl)sulfonyl)ethyl)oxycarbonyl)methyl 2-(6-methoxy-2-naphthyl)propanoate Acetic anhydride (1.00 g, 11.5 mmol) was cooled to 0° C. and fuming nitric acid (90%, 351.2 μL, 7.52 mmol) was added. The fuming nitric acid/acetic anhydride mixture was added drop-wise rapidly to a solution of the product of Example 25b (2.13 g, 5.02 mmol) in EtOAc (10 mL) at 0° C. and the resulting mixture stirred for 3 hours at 0° C. CH$_2$Cl$_2$ (7 mL) and NaHCO$_3$ (3 mL) were cooled to 0° C. and the reaction mixture was added to it. The aqueous portion was separated and extracted with additional CH$_2$Cl$_2$ (10 mL) and the combined organic extracts were washed with brine, and dried over MgSO$_4$. The solvent was removed under reduced pressure and the resulting residue purified via column chromatography on silica gel eluting with 2:1 hexanes/EtOAc followed by 1:1 hexanes/EtOAc to give the title compound (29.7 mg, 1.3% yield) as a white solid. $^1$H NMR (300 MHz, CDCl$_3$); δ 7.74-7.68 (m, 3H), 7.41 (dd, J=1.7, 8.5 Hz, 1H), 7.17-7.12 (m, 2H), 4.74 (t, J=5.9 Hz, 2H), 4.61 (s, 3H), 4.53 (t, J=5.5 Hz 2H), 3.97 (q, J=7.2 Hz, 1H), 3.91 (s, 3H), 3.25-3.17 (m, 4H), 1.61 (d, J=7.2 Hz, 3H); Mass spectrum (API-TIS) m/z 488 (M+18)

Example 26

(1S,5S,2R,6R)-6-(Nitrooxy)-4,8-dioxabicyclo(3.3.0)oct-2-yl)oxycarbonyl)methyl (2S)-2-(6-methoxy(2-naphthyl))propanoate To a solution of the product of Example 17b (1.11 g, 3.85 mmol) and (2S)-7-(nitrooxy)-4,8-dioxabicyclo(3.3.0)octan-2-ol (773 mg, 4.04 mmol) in anhydrous dichloromethane (25 mL) were added 1-ethyl-3-(3-dimethylaminopropyl)carbamide hydrochloride (EDAC) (812 mg (4.24 mmol) and a catalytic amount of N,N-dimethylaminopyridine (DMAP) at room temperature under nitrogen atmosphere. The reaction mixture was stirred at room temperature overnight, then diluted with CH$_2$Cl$_2$, washed with H$_2$O, brine, dried over sodium sulfate, filtered, and the organic extracts were evaporated in vacuo to give a white foam. The solid was recrystallized from boiling EtOAc/hexanes to give the title compound (1.26 g, 71% yield) as a white crystalline solid: Mp 104-106° C. $^1$H NMR (CDCl$_3$) δ 7.73 (m, 3H), 7.45 (m, 1H), 7.15 (m, 2H), 5.15 (m, 1H), 5.02 (m, 1H), 4.60 (ABq, 2H, J$_{AB}$=16.0 Hz, Δν$_{AB}$=29.9 Hz), 4.39 (t, 1H, J=5.2 Hz), 3.99-3.61 (m, 6H), 3.91 (s, 3H), 1.62 (d, 3H, J=7.2 Hz); LRMS (APIMS) m/z 462 (M+1)$^+$.

Example 27

(2S)-2,3-Bis(nitrooxy)propyl(2S)-2-(6-methoxy-5-nitro(2-naphthyl)) propanoate and (2S)-2-Hydroxy-3-(nitrooxy)propyl(2S)-2-(6-methoxy(2-naphthyl)) propanoate 27a. ((4R)-2,2,4-Trimethyl-1,3-dioxolan-4-yl)methyl (2S)-2-(6-methoxy(2-naphthyl)) propanoate To a solution of (2S)-2-(6-methoxy(2-naphthyl))propanoic acid (naproxen, 32.2 g, 0.14 mol) and ((4S)-2,2,4-trimethyl-1,3-dioxolan-4-yl)methan-1-ol (15 g, 0.113 mol) in anhydrous dichloromethane (750 mL) were added 1-ethyl-3-(3-dimethylaminopropyl)carbamide hydrochloride (EDAC) (23 g, 0.12 mol) and N,N-dimethylaminopyridine (DMAP, 7.5 g, 61 mmol) at room temperature under nitrogen atmosphere. The reaction mixture was stirred at room temperature overnight, then quenched with water. The organic layer was washed with brine, dried over sodium sulfate, filtered, and solvent was evaporated under reduced pressure. The product was purified by column chromatography over silica gel eluting with 20% ethyl acetate in hexane to give the title compound (37.5 g, 96.5% yield) as a white solid, mp 65-66° C. $^1$H NMR (CDCl$_3$) δ 7.75 (d, J=8.7 Hz, 1H), 7.73 (d, J=1.2 Hz, 1H), 7.46 (dd, J=8.4 and 1.7 Hz, 1H), 7.15 (m, 2H), 4.27 (m, 1H), 4.19 (m, 2H), 4.03-3.92 (m, 2H), 3.96 (s, H), 3.69 (dd, J=8.4 and 6.0 Hz, 1H), 1.64 (d, J=7.1 Hz, 3H), 1.40 (s, 3H), 1.37 (s, 3H); $^{13}$C NMR (75 MHz, CDCl$_3$) δ 174.4, 157.6, 135.3, 133.7, 129.2, 128.8, 127.1, 126.1, 125.9, 119.0, 109.7, 105.5, 73.4, 66.2, 64.8, 55.2, 45.2, 26.5, 25.3, 18.4; LRMS (APIMS) m/z 362 (M+NH$_4$)$^+$.

27b. (2R)-2,3-Dihydroxy-2-methylpropyl(2S)-2-(6-methoxy(2-naphthyl))propanoate

A solution of the product of Example 27a (25 g, 72.6 mmol) in tetrahydrofuran (250 mL), water (25 mL), and trifluoroacetic acid (2.5 mL) was refluxed for 24 hours. The reaction mixture was cooled to room temperature and the solvent was removed. The residue was dissolved in dichloromethane, dried over sodium sulfate, filtered, and evaporated in vacuo. The product was purified by column chromatography over silica gel eluting with ethyl acetate:hexane (50:50) to give the title compound (19.5 g, 89% yield) as a white solid. Mp 65-66° C. $^1$H NMR (CDCl$_3$) δ 7.75 (m, 3H), 7.42 (dd, J=8.4 and 1.2 Hz, 1H), 7.2-7.1 (m, 2H), 4.15 (d, J=6.5 Hz, 1H), 3.96 (s, 3H), 3.9 (m, 1H), 3.82 (m, 1H), 3.56 (dd, J=11.5 and 4.7 Hz, 1H), 3.44 (dd, J=11.5 and 4.8 Hz, 1H), 2.85 (br s, 2H), 1.61 (d, J=7.1 Hz, 3H); $^{13}$C NMR (75 MHz, CDCl$_3$) δ 175.1, 157.6, 135.2, 133.6, 129.2, 128.8, 127.2, 125.94, 125.9, 119.1, 105.5, 69.9, 65.4, 63.1, 55.2, 45.3, 18.3; LRMS (APIMS) m/z 322 (M+NH$_4$)$^+$.

27c. (2S)-2,3-Bis(nitrooxy)propyl(2S)-2-(6-methoxy (2-naphthyl))propanoate and (2S)-2-Hydroxy-3-(nitrooxy)propyl(2S)-2-(6-methoxy(2-naphthyl))propanoate)

Acetic anhydride (3.1 mL) was added to fuming nitric acid (90%, 0.9 mL) at 0° C. This mixture was then added to a solution of the product of Example 27b (1.84 g, 6.05 mmol) in anhydrous ethyl acetate (40 mL) at 0° C. The reaction mixture was stirred at 0° C. for 45 minutes, treated with ice cold water and extracted with ethyl acetate. The combined organic extracts were washed with water, brine, dried over sodium sulfate, and solvent was evaporated to give the crude product that was purified by flash column chromatography on silica gel eluting with EtOAc:hexane (1:9). The less polar product (2S)-2,3-bis(nitrooxy)propyl(2S)-2-(6-methoxy(2-naphthyl))propanoate was obtained as a white solid (480 mg, 20% yield). Mp 55-57° C. $^1$H NMR (CDCl$_3$) δ 7.76 (d, J=6.8 Hz, 2H), 7.7 (s, 1H), 7.42 (d, J=6.5 Hz, 1H), 7.23-7.17 (m, 2H), 5.41 (s, 1H), 4.8-4.2 (m, 4H), 3.97 (s, 3H), 3.93 (m, 1H), 1.66 (d, J=6.9 Hz, 3H); $^{13}$C NMR (75 MHz, CDCl$_3$) δ 173.8, 157.8, 134.6, 133.8, 129.2, 128.8, 127.4, 126.0, 125.8, 119.3, 105.5, 76.1, 66.4, 60.4, 55.3, 45.1, 18.0; LRMS (APIMS) m/z 395 (MH)$^+$. The more polar product (2S)-2-hydroxy-3-(nitrooxy)propyl(2S)-2-(6-methoxy(2-naphthyl))propanoate) was isolated as a white solid (1.1 g, 53% yield). Mp 50-53° C. $^1$H NMR (CDCl$_3$) δ 7.77 (d, J=3.7 Hz, 1H), 7.74 (d, J=4.0 Hz, 1H), 7.71 (s, 1H), 7.43 (dd, J=8.4 and 1.4 Hz, 1H), 7.21 (dd, J=9.0 and 2.5 Hz, 1H), 7.16 (d, J=2.3 Hz, 1H), 4.41-4.32 (m, 2H), 4.21-4.1 (m, 2H), 4.05 (m, 1H), 3.96 (s, 3H), 3.95 (m, 1H), 3.20 (br s, 1H, OH), 1.64 (d, J=7.2 Hz, 3H); $^{13}$C NMR (75 MHz, CDCl$_3$) δ 174.7, 157.7, 135.0, 133.7, 129.2, 128.85, 127.3, 125.94, 125.9, 119.2, 105.6, 72.9, 66.5, 64.8, 55.3, 45.2, 18.2; LRMS (APIMS) m/z 350 (MH)$^+$.

Example 28

(2R)-2-hydroxy-3-(nitrooxy)propyl(2S)-2-(6-methoxy(2-naphthyl)) propanoate 28a. ((4R)-2,2,4-Trimethyl-1,3-dioxolan-4-yl)methyl (2S)-2-(6-methoxy(2-naphthyl))propanoate To a solution of (2S)-2-(6-methoxy(2-naphthyl))propanoic acid (naproxen, 33.5 g, 0.145 mol) and ((4R)-2,2-dimethyl-1,3-dioxolan-4-yl)methan-1-ol (15 g, 0.113 mol) in anhydrous dichloromethane (750 mL) were added 1-ethyl-3-(3-dimethylaminopropyl)carbamide hydrochloride (EDAC, 23 g, 0.12 mol) and N,N-dimethylaminopyridine (DMAP, 7.5 g, 61 mmol) at room temperature under nitrogen atmosphere. The reaction mixture was stirred at room temperature overnight, then quenched with water. The organic layer was washed with brine, dried over sodium sulfate, filtered, and solvent evaporated under reduced temperature. The product was purified by column chromatography on silica gel eluting with EtOAc:hexane (2:8) to give the title compound (35.8 g, 92% yield) as a white solid. Mp 79-80° C. $^1$H NMR (CDCl$_3$) δ 7.76 (d, J=9.1 Hz, 2H), 7.46 (dd, J=8.7, 1.8 Hz, 1H), 7.19 (m, 2H), 7.0 (s, 1H), 4.28 (m, 1H), 4.18 (m, 2H), 4.0 (m, 2H), 3.94 (s, 3H), 3.68 (m, 1H), 1.65 (d, J=7.1 Hz, 3H), 1.41 (s, 3H), 1.38 (s, 3H); $^{13}$C NMR (75 MHz, CDCl$_3$) δ 174.4, 157.6, 135.3, 133.7, 129.2, 128.9, 127.1, 126.1, 126.0, 119.0, 109.6, 105.5, 73.4, 66.1, 64.4, 55.2, 45.2, 26.5, 25.3, 18.4; LRMS (APIMS) m/z 345 (MH)$^+$.

28b. (2R)-2,3-Dihydroxy-2-methylpropyl(2S)-2-(6-methoxy(2-naphthyl))propanoate

A solution of the product of Example 28a (38 g, 110 mmol) in tetrahydrofuran (360 mL), water (40 mL) and trifluoroacetic acid (4 mL) was refluxed for 24 hours. The reaction mixture was cooled to room temperature and solvent was evaporated. The residue was dissolved in dichloromethane, dried over sodium sulfate, filtered, and solvent was evaporated. The product was purified by column chromatography on silica gel eluting with EtOAc:hexane (1:1) to give the title compound (27.5 g, 81% yield) as a white solid. Mp 65-71° C. $^1$H NMR (CDCl$_3$) δ 7.75 (dd, J=8.3, 1.5 Hz, 2H), 7.70 (s, 1H), 7.41 (dd, J=8.5, 1.7 Hz, 1H), 7.18 (m, 2H), 4.17 (dd, J=6.2 and 3.5 Hz, 2H), 3.96 (s, 3H), 3.95-3.84 (m, 2H), 3.60 (m, 1H), 3.49 (m, 1H), 2.51 (br s, 2H, 2×OH), 1.62 (d, J=7.2 Hz, 3H); $^{13}$C NMR (75 MHz, CDCl$_3$) δ 175.1, 157.7, 135.2, 133.7, 129.2, 128.8, 127.26, 125.93, 125.9, 119.1, 105.5, 70.0, 65.4, 63.1, 55.3, 45.3, 18.3; LRMS (APIMS) m/z 305 (MH)$^+$, 322 (M+NH$_4$)$^+$.

28c. (2R)-2-Hydroxy-3-(nitrooxy)propyl(2S)-2-(6-methoxy(2-naphthyl))propanoate

The product of Example 28b was nitrated following the procedure for Example 27d to give a mixture of the product of Example 5 (29% yield) and the title compound (34% yield) as white solids. $^1$H NMR (CDCl$_3$) δ 7.78 (d, J=3.4 Hz, 1H), 7.74 (d, J=3.7 Hz, 1H), 7.71 (s, 1H), 7.42 (dd, J=7.5 and 1.5 Hz, 1H), 7.21 (dd, J=8.8 and 2.4 Hz, 1H), 7.17 (d, J=2.3 Hz, 1H), 4.4 (m, 2H), 4.3-4.1 (m, 3H), 3.96 (s, 3H), 3.95 (m, 1H), 3.20 (br s, 1H, OH), 1.65 (d, J=7.1 Hz, 3H); LRMS (APIMS) m/z 350 (MH)$^+$.

Example 29

(2S)-2-(6-Methoxy(2-naphthyl))-N—((N-(2-(nitrooxy)ethyl)carbamoyl)methoxy)propanamide 29a. tert-Butyl 2-(1,3-dioxobenzo(c)azolin-2-yloxy)acetate A mixture of N-hydroxyphthalimide (10 g, 61.3 mmol), K$_2$CO$_3$ (16.9 g, 122 mmol) and tert-butyl bromoacetate (12 g, 9 mL, 61.3 mmol) in DMF (60 mL) was stirred at room temperature for 3 hours and the solvent was evaporated under high vacuum. The residue was dissolved in EtOAc, washed with brine, dried over Na$_2$SO$_4$ and filtered. The residue after evaporation of the solvent was recrystallized from a mixture of CH$_2$Cl$_2$/EtOAc/hexane to give the title compound (12 g, 71% yield) as a white solid. Mp 140-141° C. $^1$H NMR (300 MHz, CDCl$_3$) δ 7.80-7.90 (m, 2H), 7.74-7.77 (m, 2H), 4.71 (s, 2H), 1.49 (s, 9H). $^{13}$C NMR (75 MHz, CDCl$_3$) δ 166.0, 163.0, 134.7, 128.9, 123.7, 83.0, 73.5, 28.1. Mass spectrum (API-TIS) m/z 278 (MH$^+$), 295 (MNH$_4^+$). Anal. calcd. for C$_{14}$H$_{15}$NO$_5$: C, 60.64; H, 5.45; N, 5.05. Found: C, 60.47; H, 5.31; N, 4.96.

29b. tert-Butyl 2-aminooxyacetate

Hydrazine monohydrate (2.1 g, 2.1 mL, 67.3 mmol) was added drop-wise to a solution of the product of Example 29a (4.65 g, 16.8 mmol) in CH$_2$Cl$_2$ (25 mL) and methanol (3 mL) at room temperature. The resultant suspension was stirred at room temperature for 30 minutes. The residue, after evaporation of the solvent, was dissolved in 5% Na$_2$CO$_3$ and extracted with EtOAc. The organic layer was washed with water, brine, dried over anhydrous Na$_2$SO$_4$, filtered and evaporated in vacuo to give the title compound (2.36 g, 96% yield) as a colorless oil. $^1$H NMR (300 MHz, CDCl$_3$) δ 5.80-5.90 (bs, 2H), 4.13 (s, 2H), 1.50 (s, 9H). Mass spectrum (API-TIS) m/z 148 (MH$^+$).

29c. tert-Butyl 2-((2S)-2-(6-methoxy(2-naphthyl)) propanoylaminooxy)acetate

A mixture of (2S)-2-(6-methoxy(2-naphthyl))propanoic acid (naproxen, 1.6 g, 7.0 mmol), the product of Example 29b (1 g, 7.0 mmol) and N,N-dimethylaminopyridine (DMAP, 0.85 g, 7.0 mmol) in CH$_2$Cl$_2$ (20 mL) at 0° C. was treated with 1-(3-(dimethylamino)propyl)-3-ethylcarbodiimide hydrochloride (1.34 g, 7.0 mmol). The reaction mixture was stirred at room temperature for 3 days, diluted with CH$_2$Cl$_2$, washed with water, brine and dried over Na$_2$SO$_4$. The residue after filtration and evaporation was chromatographed on silica gel eluting with EtOAc:hexane (1:3 to 1:2) to give the title compound (1.9 g, 74% yield) as a white solid. Mp 82-84° C. $^1$H NMR (300 MHz, CDCl$_3$) δ 8.72-8.85 (bs, 1H), 7.63-7.70 (m, 3H), 7.34 (dd, J=1.6 and 8.5 Hz, 1H), 7.02-7.16 (m, 2H), 4.15-4.37 (bs, 2H), 3.89 (s, 3H), 3.49-3.64 (bs, 1H), 1.56 (d, J=7.0 Hz, 3H), 1.30 (s, 9H). $^{13}$C NMR (75 MHz, CDCl$_3$) δ 171.9, 168.8, 157.8, 135.4, 133.8, 129.3, 129.0, 127.5, 126.0, 119.2, 105.6, 82.7, 72.5, 55.3, 44.0, 27.9, 18.3. Mass spectrum (API-TIS) m/z 360 (MH$^+$). Anal. calcd. for C$_{20}$H$_{25}$NO$_5$: C, 66.84; H, 7.01; N, 3.90. Found: C, 66.85; H, 6.99; N, 3.84.

29d. 2-((2S)-2-(6-Methoxy(2-naphthyl))propanoylaminooxy)acetic acid

Trifluoroacetic acid (4 mL) was added drop-wise to a solution of the product of Example 29c (1.8 g, 5.0 mmol) in CH$_2$Cl$_2$ (8 mL). The reaction mixture was stirred at room temperature for 16 hours and the volatile material removed in vacuo. The residue after evaporation was recrystallized from EtOAc/hexane to give the title compound (1.32 g, 87% yield) as a white solid. Mp 152-153° C. $^1$H NMR (300 MHz, d$_6$-DMSO) δ 8.98-9.10 (bs, 1H), 7.60-7.90 (m, 3H), 7.42 (dd, J=1.5 and 8.7 Hz, 1H), 7.25-7.29 (m, 1H), 7.15 (dd, J=2.7 and 9.0 Hz, 1H), 4.32 (ABq, J$_{AB}$=16.9 Hz, Δν$_{AB}$=23.7 Hz, 2H), 3.86 (s, 3H), 3.64 (q, J=7.8 Hz, 1H), 1.40 (d, J=7.0 Hz, 3H). $^{13}$C NMR (75 MHz, d$_6$-DMSO) δ 171.0, 170.3, 157.1, 136.3, 133.2, 129.2, 128.4, 126.7, 126.3, 125.4, 118.7, 105.7, 71.6, 55.2, 41.5, 18.1. Mass spectrum (API-TIS) m/z 304 (MH$^+$). Anal. calcd. for C$_{16}$H$_{17}$NO$_5$: C, 63.36; H, 5.65; N, 4.62. Found: C, 63.42; H, 5.44; N, 4.42.

29e. (2S)-2-(6-Methoxy(2-naphthyl))-N—((N-(2-(nitrooxy)ethyl)carbamoyl)methoxy)propanamide A mixture of the product of Example 29d (0.5 g, 1.65 mmol), the product of Example 22a (0.28 g, 1.65 mmol) and N,N-dimethylaminopyridine (DMAP, 0.20 g, 1.65 mmol) in CH$_2$Cl$_2$ (5 mL) at 0° C. was treated with 1-(3-(dimethylamino)propyl)-3-ethylcarbodiimide hydrochloride (0.35 g, 1.65 mmol) in CH$_2$Cl$_2$ (5 mL). The reaction mixture was stirred at 0° C. for 3 hours, diluted with CH$_2$Cl$_2$, washed with water, brine and dried over Na$_2$SO$_4$. The residue after filtration and evaporation was chromatographed on silica gel eluting with EtOAc:hexane (1:2) to MeOH:EtOAc:hexane (0.1:1:1) to give the title compound (0.33 g, 51% yield) as a white solid. Mp 40-44° C. $^1$H NMR (300 MHz, CDCl$_3$) δ 8.79-8.90 (bs, 1H), 8.48-8.51 (bs, 1H), 7.60-7.76 (m, 3H), 7.32 (dd, J=1.7 and 8.4 Hz, 1H), 7.11-7.20 (m, 2H), 4.54 (t, J=5.0 Hz, 2H), 4.23 (s, 2H), 3.92 (s, 3H), 3.59-3.67 (m, 1H), 1.59 (d, J=7.1 Hz, 3H). $^{13}$C NMR (75 MHz, CDCl$_3$) δ 175.1, 169.4, 158.1, 134.5, 134.1, 129.3, 129.0, 127.9, 126.3, 125.8, 119.6, 105.7, 76.0, 71.1, 55.5, 44.0, 36.6, 18.2. Mass spectrum (API-TIS) m/z 392 (MH$^+$). Anal. calcd. for C$_{18}$H$_{21}$N$_3$O$_7$: C, 55.24; H, 5.41; N, 10.74. Found: C, 54.97; H, 5.42; N, 10.52.

Example 30

3-(2-(4-((Nitrooxy)methyl)phenyl)acetyloxy)-2-oxopropyl(2S)-2-(6-methoxy(2-naphthyl))propanoate

30a. 2-(4-((Nitrooxy)methyl)phenyl)acetic acid

A solution of silver nitrate (7.78 g, 45.8 mmol) and 4-(bromomethyl)phenylacetic acid (5.18 g, 22.6 mmol) in THF (100 mL) and acetonitrile (50 mL) was stirred at ambient temperature overnight and then at 50° C. for 1 hour. The reaction mixture was then cooled to ambient temperature and stirred with brine (100 mL) for 1 hour. The resulted mixture was filtered through Celite and washed with water. The filtrate was concentrated and then extracted with ethyl acetate. The combined organic extracts were washed with water, brine, dried over Na$_2$SO$_4$, filtered, concentrated and dried under vacuum. The product was purified by silica gel column chromatography eluting with EtOAc/hexane (2:3, Rf=0.13) to obtained the title compound as a white solid (3.2 g, 67% yield). Mp 109-110° C. $^1$H NMR (300 MHz, d$_4$-methanol) δ 8.23 (d, J=8.0 Hz, 2H), 8.14 (d, J=8.0 Hz, 2H), 6.34 (s, 2H), 4.43 (s, 2H). $^{13}$C NMR (75 MHz, d$_4$-methanol) δ 172.6, 136.5, 130.7, 129.9, 129.5, 75.1, 40.5. Mass spectrum (API-TIS) m/z 210 (M–H)$^-$.

30b. 3-(2-(4-((Nitrooxy)methyl)phenyl)acetyloxy)-2-oxopropyl(2S)-2-(6-methoxy(2-naphthyl))propanoate 1,3-Dicyclohexylcarbodiimide (1.55 g, 7.5 mmol) was added to a solution of the product of Example 11b (2.13 g, 7.1 mmol), the product of Example 30a (1.49 g, 7.1 mmol) and N,N-dimethylaminopyridine (DMAP, 0.93 g, 7.6 mmol) in CH$_2$Cl$_2$ (100 mL) and stirred at ambient temperature overnight. The byproduct, dicyclohexyl urea, was removed by filtration. The filtrate was concentrated and the residue was dissolved in CH$_2$Cl$_2$ (150 mL), washed with 3N HCl (100 mL), water (100 mL), brine, and dried over Na$_2$SO$_4$, filtered and concentrated. The product was purified by silica gel column chromatography eluting with EtOAc/hexane (1:2, Rf=0.15) to obtained the title compound as a oil (1.25 g, 36% yield). The oil solidified after standing for 3 months at ambient temperature. Mp 92-95° C. $^1$H NMR (300 MHz, CDCl$_3$) δ 7.7-7.1 (m, 10H), 5.35 (s, 2H), 4.7-4.6 (m, 4H), 3.95 (q, J=7.1 Hz, 1H), 3.89 (s, 3H), 3.69 (s, 2H), 1.59 (d, J=7.1 Hz, 3H). $^{13}$C NMR (75 MHz, CDCl$_3$) δ 197.5, 173.7, 170.2, 157.7, 134.7, 134.6, 133.7, 131.2, 129.8, 129.3, 129.2, 128.8, 127.2, 126.03, 126.0, 119.1, 105.5, 74.3, 66.4, 55.2, 44.9, 40.2, 18.3. Mass spectrum (API-TIS) m/z 496 (MH)$^+$.

Example 31

2-(4-(2-(nitrooxy)ethyl)piperidyl)-2-oxoethyl(2S)-2-(6-methoxy(2-naphthyl))propanoate

31a. Nitrooxy(2-(4-piperidyl)ethyl)hydrogennitrate

4-Piperidylethan-1-ol (10 g, 77.3 mmol) in a mixture of EtOAc (90 mL) and CH$_2$Cl$_2$ (5 mL) was added drop-wise to a mixture of fuming HNO$_3$ (24.4 g, 16.3 mL, 387 mmol) and Ac$_2$O (63.2 g, 58.4 mL, 619 mmol) at –10° C. The reaction mixture was stirred at −10° C. for 30 minutes and then diluted with EtOAc and hexane. The precipitate was collected by filtration and washed with hexane to give the title compound (7.5 g, 41% yield) as a white solid. Mp 86-88° C. $^1$H NMR (300 MHz, $d_6$-DMSO) δ 8.20-8.30 (bs, 1H), 8.05-8.20 (bs, 1H), 4.57 (t, J=6.2 Hz, 2H), 3.15-3.30 (m, 2H), 2.70-2.90 (m, 2H), 1.75-1.90 (m, 2H), 1.55-1.72 (m, 3H), 1.19-1.37 (m, 2H). $^{13}$C NMR (75 MHz, $d_6$-DMSO) δ 71.6, 43.2, 31.9, 30.0, 28.1. Mass spectrum (API-TIS) m/z 175 (MH$^+$). Anal. calcd. for $C_7H_{15}N_3O_6$: C, 35.44; H, 6.37; N, 17.71. Found: C, 35.62; H, 6.39; N, 17.65.

31b. 2-(4-(2-(Nitrooxy)ethyl)piperidyl)-2-oxoethyl (2S)-2-(6-methoxy(2-naphthyl))propanoate A mixture of the product of Example 17b (1.5 g, 5.21 mmol), the product of Example 31a (1.2 g, 5.21 mmol) and N,N-dimethylaminopyridine (DMAP, 0.63 g, 5.21 mmol) in $CH_2Cl_2$ (30 mL) at 0° C. was treated with 1-(3-(dimethylamino)propyl)-3-ethylcarbodiimide hydrochloride (1.0 g, 5.21 mmol). The reaction mixture was stirred at 0° C. for 3 hours, diluted with $CH_2Cl_2$, washed with water, brine and dried over $Na_2SO_4$. The residue after filtration and evaporation was chromatographed on silica gel eluting with EtOAc:Hexane (1:3 to 1:2 to 1:1) to give the title compound (1.0 g, 43% yield) as a white solid. Mp 83-85° C. $^1$H NMR (300 MHz, $d_6$-DMSO) δ 7.65-7.75 (m, 3H), 7.44 (d, J=8.5 Hz, 1H), 7.07-7.18 (m, 2H), 4.46-4.81 (m, 3H), 4.30-4.44 (m, 2H), 3.99 (q, J=6.9 Hz, 1H), 3.91 (s, 3H), 3.50-3.59 (m, 1H), 2.75-2.93 (m, 1H), 2.41-2.60 (m, 1H), 1.63 (d, J=7.9 Hz, 3H), 1.32-1.74 (m, 5H), 0.69-1.20 (m, 2H). $^{13}$C NMR (75 MHz, $d_6$-DMSO) δ 174.3, 164.8, 157.8, 135.5, 133.9, 129.4, 129.0, 127.3, 126.5, 126.4, 119.1, 105.7, 70.7, 62.3, 55.4, 45.4, 44.8, 42.2, 33.0, 32.6, 32.0, 31.4, 18.4. Mass spectrum (API-TIS) m/z 445 (MH$^+$), 462 (MNH$_4^+$). Anal. calcd. for $C_{23}H_{28}N_2O_7$: C, 62.15; H, 6.35; N, 6.30. Found: C, 62.21; H, 6.42; N, 6.26.

Example 32

4-((2-(Nitrooxy)ethyl)oxycarbonyl)phenyl(2S)-2-(6-methoxy(2-naphthyl))propanoate

32a. 2-(Nitrooxy)ethyl 4-hydroxybenzoate

To 4-hydroxybenzoic acid (1.2918 g, 9.347 mmol) in DMF (10 mL) was added potassium carbonate (1.60 g, 11.6 mmol) and the product of Example 15a (1.44 g, 8.48 mmol). The reaction mixture was stirred at room temperature for 48 hours, filtered, and concentrated to dryness. The product was dissolved in EtOAc, washed with $H_2O$, brine, dried over magnesium sulfate, filtered, and concentrated. The product was chromatographed on silica gel eluting with MeOH:$CH_2Cl_2$ (0:100, then 2:98) to give the title compound (430.2 mg, 22% yield). $^1$H NMR (300 MHz, CDCl$_3$) δ 7.95 (d, J=7.4 Hz, 2H), 6.89 (d, J=7.4 Hz, 2H), 6.24 (s, 1H), 4.80 (m, 2H), 4.59 (m, 2H). $^{13}$C NMR (75 MHz, CDCl$_3$) δ166.1, 160.5, 132.2, 121.5, 115.4, 70.6, 60.6. Mass spectrum APIMS (IS, NH$_4$OAc) m/z 228 (M+H$^+$), 245 (M+NH$_4^+$), 250 (M+Na$^+$).

32b. 4-((2-(Nitrooxy)ethyl)oxycarbonyl)phenyl(2S)-2-(6-methoxy(2-naphthyl))propanoate To (2S)-2-(6-methoxy(2-naphthyl))propanoic acid (naproxen, 456.0 mg, 1.980 mmol) and the product of Example 32a (399.1 mg, 1.757 mmol) in $CH_2Cl_2$ (20 mL) was added N,N-dicyclohexylcarbodiimide (418.4 mg, 2.028 mmol). The reaction mixture was stirred for 15 minutes and then N,N-dimethylaminopyridine (185.0 mg, 1.51 mmol) was added. The reaction mixture was stirred at room temperature for 3 hours and filtered to remove the solid. The solid was washed with dichloromethane. The filtrate was washed with citric acid (0.2 M), brine, sodium bicarbonate solution, brine, dried over magnesium sulfate, filtered, and concentrated. The product was chromatographed on silica gel eluting with $CH_2Cl_2$ to give the title compound (0.62 g, 81% yield). $^1$H NMR (300 MHz, CDCl$_3$) δ 8.03-7.98 (m, 2H), 7.77-7.72 (m, 3H), 7.49 (dd, J=8.6 Hz & 1.7 Hz, 1H), 7.19-7.14 (m, 2H), 7.10-7.06 (m, 2H), 4.78-4.75 (m, 2H), 4.58-4.55 (m, 2H), 4.11 (q, J=7.1 Hz, 1H), 3.92 (s, 3H), 1.70 (d, J=7.1 Hz, 3H). $^{13}$C NMR (75 MHz, CDCl$_3$) δ 172.6, 165.3, 157.8, 154.9, 134.7, 133.9, 131.3, 129.3, 128.9, 127.5, 126.7, 126.2, 125.9, 121.6, 119.2, 105.6, 70.4, 60.8, 55.3, 45.6, 18.4. Mass spectrum APIMS (IS, NH$_4$OAc) m/z 440 (M+H$^+$), 457 (M+NH$_4^+$), 462 (M+Na$^+$), 896 (2M+NH$_4^+$).

Example 33

2-((2-(Nitrooxy)ethyl)oxycarbonyl)phenyl(2S)-2-(6-methoxy(2-naphthyl)propanoate

33a. 2-(Nitrooxy)ethyl 2-hydroxybenzoate

To the product of Example 15a (1.80 g, 10.6 mmol) in N,N-dimethylfomamide (10 mL) was added salicylic acid (1.4620 g, 10.6 mmol) and potassium carbonate (1.4827 g, 10.7 mmol). The reaction mixture was stirred at room temperature for two hours then at 65° C. overnight, and concentrated to dryness. The product was treated with EtOAc and filtered. The filtrate was washed with sodium bicarbonate, brine, dried over magnesium sulfate, filtered, and concentrated. The product was chromatographed on silica gel eluting with EtOAc:hexane (3:97, 1:9, 1:5, 2:3) to give the title compound (0.35 g, 14% yield). $^1$H NMR (300 MHz, CDCl$_3$) δ 10.5 (s, 1H), 7.84-7.81 (m, 1H), 7.51-7.45 (m, 1H), 7.00-6.97 (m, 1H), 6.92-6.87 (m, 1H), 4.86-4.79 (m, 2H), 4.64-4.61 (m, 2H). $^{13}$C NMR (75 MHz, CDCl$_3$) δ169.6, 161.7, 136.3, 129.9, 119.4, 117.7, 111.6, 70.1, 60.9.

33b. 2-((2-(nitrooxy)ethyl)oxycarbonyl)phenyl(2S)-2-(6-methoxy(2-naphthyl)propanoate To a mixture of (2S)-2-(6-methoxy(2-naphthyl))propanoic acid (naproxen, 324.5 mg, 1.409 mmol), the product of Example 33a (292.6 mg, 1.288 mmol), and N,N-dicyclohexylcarbodiimide (153.2 mg, 1.254 mmol) was added $CH_2Cl_2$ (15 mL) and N,N-dimethylaminopyridine (284.4 mg, 1.378 mmol). The reaction mixture was stirred at room temperature for 3 hours, and filtered. The filtrate was washed with citric acid (0.2 M), brine, sodium bicarbonate solution, brine, dried over magnesium sulfate, filtered, and concentrated. The product was chromatographed on silica gel eluting with $CH_2Cl_2$ to give the title compound (355.8 mg, 63% yield). $^1$H NMR (300 MHz, CDCl$_3$) δ 7.96-7.94 (m, 1H), 7.79-7.72 (m, 3H), 7.54-7.46 (m, 2H), 7.29-7.24 (m, 1H), 7.17-7.14 (m, 2H), 6.93-6.91 (m, 1H), 4.60-4.57 (m, 2H), 4.43-4.30 (m, 2H), 4.19 (q, J=7.1 Hz, 1H), 3.91 (s, 3H), 1.72 (d, J=7.1 Hz, 3H). $^{13}$C NMR (75 MHz, CDCl$_3$) δ 173.1, 164.0, 157.7, 150.7, 135.0, 134.1, 133.8, 131.6, 129.3, 128.9, 127.2, 126.34, 126.31, 126.0, 123.6, 122.7, 119.1, 105.5, 70.3, 60.6, 55.3, 45.4, 18.6. Mass spectrum APIMS (IS, NH$_4$OAc) m/z 440 (M+H$^+$), 457 (M+NH$_4^+$), 462 (M+Na$^+$), 896 (2M+NH$_4^+$).

Example 34

(N-methyl-N-(3-(nitrooxy)propyl)carbamoyl)methyl (2S)-2-(6-methoxy(2-naphthyl))propanoate

34a. N-(3-Hydroxypropyl)carboxamide

3-Amino-1-propanol (10.0 mL, 130.7 mmol) and ethyl formate (31.7 mL, 392.2 mmol) were combined together and stirred at room temperature for 24 hours. The excess ethyl formate was removed under reduced pressure to give the title compound (8.6 g, 64% yield) as a yellow oil. $^1$H NMR (300 MHz, CDCl$_3$); δ 8.11-8.04 (m, 1H), 3.63-3.61 (m, 2H), 3.37-3.33 (m, 2H), 1.87-1.85 (m, 2H).

34b. 3-(Methylamino)propan-1-ol

A solution of the product of Example 34a (8.60 g, 83.3 mmol) in 10 mL of THF was added to LAH in THF (1M, 100 mL) at 0° C. The mixture was heated reflux for 3 hours. Water was added (3.79 mL) followed by NaOH solution (10%, 11.4 mL) and water (3.79 mL). The resulting solid was removed via filtration and the solid washed with additional THF (10 mL). The filtrate was collected and the solvent removed under reduced pressure to give the title compound (4.40 g, 59% yield) as a yellow oil which was used without further purification. $^1$H NMR (300 MHz, CDCl$_3$); δ 3.74 (m, 2H), 2.78 (m, 2H), 2.38 (s, 3H), 1.66 (q, J=5.0, 2H).

34c. Methyl(3-(nitrooxy)propyl)amine

The product of Example 34b (750.0 mg, 4.28 mmol) dissolved in EtOH was cooled to 0° C. One equivalent of fuming nitric acid (90%, 199.8 μL, 4.28 mmol) was added and the mixture stirred for 15 minutes. The resulting solution was added drop-wise to a mixture of fuming nitric acid (90%, 300 μL, 6.42 mmol) and acetic anhydride (913 μL, 9.84 mmol) at 0° C. and the solution mixture stirred for 3 hours The excess solvent was removed under reduced pressure. Ether was added and the sample sonicated for 15 minutes. The excess ether was decanted off and the sample dried under vacuum overnight to give a yellow oil (1.29 g) that was used without further purification. $^1$H NMR (300 MHz, CDCl$_3$); δ 4.60-4.56 (m, 2H), 3.23-3.16 9M, 2H), 2.80 (br s, 3H), 2.28-2.19 (m, 2H).

34d. (N-methyl-N-(3-(nitrooxy)propyl)carbamoyl) methyl(2S)-2-(6-methoxy(2-naphthyl))propanoate A solution of EDC (1.10 g, 5.77 mmol) in CH$_2$Cl$_2$ (7 mL) was added drop-wise to a mixture of the product of Example 17b (1.38 g, 4.81 mmol) and the product of Example 34c (1.29 g, 9.61 mmol) in CH$_2$Cl$_2$ (5 mL). The mixture was stirred at room temperature for 5 hours. Water was added (15 mL) and the organic phase separated. The water layer was extracted with additional CH$_2$Cl$_2$ and the combined organic extracts were dried over MgSO$_4$, and evaporated to give a yellow oil (1.96 g). The oil was chromatographed on silica gel plug eluting with hexanes/EtOAc (3:1) and the eluant concentrated and dried under vacuum overnight. The resulting solid was trituration in Et$_2$O followed by recrystallization from CH$_2$Cl$_2$/hexanes to give the title compound as a white solid (535.5 mg, 28% yield). Mp 104-105° C. $^1$H NMR (300 MHz, CDCl$_3$); δ 7.72 (br s, 1H), 7.69 (br s, 2H), 7.44 (dd, J=8.6, 1.5 Hz, 1H), 7.11-7.15 (m, 2H), 4.76 (d, J=14.4 Hz, 1H), 4.57 (d, J=14.4 Hz, 1H), 4.44 (t, J=6.4 Hz, 2H), 4.01 (q, J=7.2 Hz, 1H), 3.91 (s, 3H), 3.46 (dt, J=2.7, 6.9 Hz, 2H), 2.89 (s, 3H), 1.95 (q, J=6.7 Hz, 2H), 1.63 (d, 3H, J=7.2). Mass spectrum (API-TIS) m/z 405 (M+1).

Example 35

(2S)-2-(6-Methoxy(2-naphthyl))-N-(2-(4-((nitrooxy) methyl)piperidyl)-2-oxoethoxy)propanamide

35a. (2S)-2-(6-Methoxy(2-naphthyl))-N-(2-(4-((nitrooxy)methyl)piperidyl)-2-oxoethoxy)propanamide A mixture of the product of Example 29d (1 g, 3.33 mmol), the product of Example 19a (0.73 g, 3.33 mmol) and N,N-dimethylaminopyridine (DMAP, 0.40 g, 3.33 mmol) in CH$_2$Cl$_2$ (10 mL) at 0° C. was treated with 1-(3-(dimethylamino)propyl)-3-ethylcarbodiimide hydrochloride (0.70 g, 3.63 mmol) in CH$_2$Cl$_2$ (10 mL). The reaction mixture was stirred at 0° C. for 3 hours, diluted with CH$_2$Cl$_2$, washed with water, brine and dried over Na$_2$SO$_4$. The residue after filtration and evaporation was chromatographed on silica gel eluting with EtOAc:hexane (1:2) to MeOH:EtOAc:hexane (0.1:1:1) to give the title compound (0.93 g, 63% yield) as a white foam solid. Mp 45-47° C. $^1$H NMR (300 MHz, CDCl$_3$) δ 8.70-8.80 (bs, 1H), 7.62-7.71 (m, 3H), 7.36-7.43 (m, 1H), 7.06-7.17 (m, 2H), 4.35-4.51 (m, 3H), 4.20-4.30 (m, 1H), 4.02-4.16 (m, 1H), 3.90 (s, 3H), 3.40-3.62 (m, 2H), 2.71-2.95 (m, 1H), 2.32-2.55 (m, 1H), 1.80-2.00 (m, 1H), 1.60-1.80 (m, 2H), 1.57 (d, J=7.0 Hz, 3H), 1.02-1.20 (m, 1H), 0.80-1.00 (m, 1H). $^{13}$C NMR (75 MHz, CDCl$_3$) δ 166.6, 157.7, 135.8, 133.7, 129.3, 128.9, 127.3, 126.2, 125.9, 119.1, 105.5, 72.7, 72.5, 55.4, 44.0, 43.6, 41.2, 34.1, 28.7, 28.0, 18.5. Mass spectrum (API-TIS) m/z 446 (MH$^+$). Anal. calcd. for C$_{22}$H$_{27}$N$_3$O$_7$: C, 59.32; H, 6.11; N, 9.43. Found: C, 59.54; H, 6.20; N, 9.55.

Example 36

3-((2-(Nitrooxy)ethyl)oxycarbonyl)phenyl(2S)-2-(6-methoxy(2-naphthyl)propanoate

36a. 2-(Nitrooxy)ethyl 3-hydroxybenzoate

To the product of Example 15a (2.1042 g, 12.380 mmol) and 3-hydroxybenzoic acid (1.95 g, 14.12 mmol) in DMF (10 mL) was added potassium carbonate (1.98 g, 14.33 mmol). The reaction mixture was stirred at room temperature overnight, and filtered. The filtrate was concentrated to dryness, dissolved in EtOAc, washed with water, sodium bicarbonate solution, brine, dried over magnesium sulfate, filtered, and concentrated. The product was chromatographed on silica gel eluting with MeOH:CH$_2$Cl$_2$ (0:100, 2:98, 3:97) to give the title compound (1.51 g, 53% yield). $^1$H NMR (CDCl$_3$) δ 7.60-7.54 (m, 2H), 7.34-7.26 (m, 1H), 7.12-7.08 (m, 1H), 6.60 (s, 1H), 4.79-4.77 (m, 2H), 4.60-4.57 (m, 2H). $^{13}$C NMR (CDCl$_3$) δ166.6, 155.9, 130.2, 129.9, 122.0, 120.9, 116.3, 70.3, 61.1. Mass spectrum APIMS (IS, NH$_4$OAc) m/z 245 (M+NH$_4^+$), 250 (M+Na$^+$), 472 (2M+NH$_4^+$).

36b. 3-((2-(Nitrooxy)ethyl)oxycarbonyl)phenyl(2S)-2-(6-methoxy(2-naphthyl)propanoate To a mixture of (2S)-2-(6-methoxy(2-naphthyl))propanoic acid (naproxen, 1.67 g, 7.25 mmol), the product of Example 36a (1.4492 g, 6.379 mmol), and N,N-dimethylaminopyridine (DMAP, 752.7 mg, 6.161 mmol) in CH$_2$Cl$_2$ (40 mL) was added N,N-dicyclohexylcarbodiimide (1.61 g, 7.80 mmol). The reaction mixture was stirred at room temperature overnight, and filtered. The filtrate was diluted with CH$_2$Cl$_2$, washed with citric acid (0.2M), brine, sodium bicarbonate solution, brine, dried over magnesium sulfate, filtered, and concentrated. The product was chromatoghraphed on silica gel eluting with CH$_2$Cl$_2$ to give the title compound (2.32 g, 83% yield). $^1$H NMR (300 MHz, CDCl$_3$) δ 7.89-7.86 (m, 1H), 7.79-7.73 (m, 3H), 7.67-7.66 (m, 1H), 7.52-7.48 (m, 1H), 7.44-7.38 (m, 1H), 7.26-7.15 (m, 3H), 4.78-4.75 (m, 2H), 4.59-4.56 (m, 2H), 4.12 (q, J=7.1 Hz, 1H), 3.92 (s, 3H), 1.71 (d, J=7.1 Hz, 3H). $^{13}$C NMR (75 MHz, CDCl$_3$) δ 172.9, 165.1, 157.7, 150.8, 134.8, 133.8, 130.6, 129.4, 129.3, 128.9, 127.4, 127.1, 126.7, 126.1, 125.9, 122.8, 119.1, 105.5, 70.3, 60.9, 55.3, 45.5, 18.4. Mass spectrum APIMS (IS, NH$_4$OAc) m/z 440 (M+H$^+$), 457 (M+NH$_4^+$), 462 (M+Na$^+$), 896 (2M+NH$_4^+$).

Example 37

2-(4-(2-(Nitrooxy)ethyl)piperazinyl)-2-oxoethyl(2S)-2-(6-methoxy(2-naphthyl))propanoate hydrogen chloride 37a. Nitrooxy(2-piperazinylethyl)dihydrogennitrate 2-piperazinylethan-1-ol (15 g, 115 mmol) in a mixture of EtOAc (132 mL) and CH$_2$Cl$_2$ (5 mL) was added drop-wise to a mixture of fuming HNO$_3$ (36.3 g, 24.2 mL, 576 mmol) and Ac$_2$O (94.1 g, 87 mL, 921 mmol) at −10° C. The reaction mixture was stirred at −10° C. for 30 minutes and diluted with EtOAc and hexane. The oil was separated and dried under vacuum to give the title compound (5.1 g, 19% yield) as a sticky oil. The crude product was used without further purification. Mass spectrum (API-TIS) m/z 176 (MH$^+$).

37b. 2-(4-(2-(Nitrooxy)ethyl)piperazinyl)-2-oxoethyl (2S)-2-(6-methoxy(2-naphthyl))propanoate A mixture of the product of Example 17b (2.67 g, 9.27 mmol), the product of Example 37a (2.2 g, 9.27 mmol) and N,N-dimethylaminopyridine (DMAP, 3.39 g, 27.8 mmol) in CH$_2$Cl$_2$ (20 mL) and DMF (9.3 mL) at 0° C. was treated with 1-(3-(dimethylamino)propyl)-3-ethylcarbodiimide hydrochloride (1.78 g, 9.27 mmol). The reaction mixture was stirred at 0° C. for 3 hours, diluted with CH$_2$Cl$_2$, washed with saturated NaHCO$_3$, dried over Na$_2$SO$_4$. The residue after filtration and evaporation was chromatographed on silica gel eluting with MeOH:EtOAc:CH$_2$Cl$_2$ (1:25:25) to give the title compound (1.2 g, 29% yield) as an oil. $^1$H NMR (300 MHz, d$_6$-DMSO) δ 7.65-7.72 (m, 3H), 7.43 (dd, J=1.6 and 8.5 Hz, 1H), 7.07-7.16 (m, 2H), 4.66 (ABq, J$_{AB}$=14.0 Hz, Δv$_{AB}$=28.0 Hz, 2H), 4.43 (t, J=5.5 Hz, 2H), 3.98 (q, J=7.1 Hz, 1H), 3.89 (s, 3H), 3.46-3.61 (m, 2H), 3.14-3.23 (m, 2H), 2.49-2.56 (m, 2H), 2.32-2.44 (m, 2H), 2.12-2.20 (m, 2H), 1.63 (d, J=7.2 Hz, 3H). $^{13}$C NMR (75 MHz, d$_6$-DMSO) δ 174.2, 172.2, 164.9, 157.8, 135.4, 135.8, 129.4, 129.0, 127.3, 126.4, 126.3, 119.1, 105.7, 70.1, 62.1, 55.4, 54.8, 52.9, 45.3, 44.6, 41.9, 18.7. Mass spectrum (API-TIS) m/z 446 (MH$^+$). Anal. calcd. for C$_{22}$H$_{27}$N$_3$O$_7$: C, 59.32; H, 6.11; N, 9.43. Found: C, 59.11; H, 5.86; N, 9.24.

37c. 2-(4-(2-(Nitrooxy)ethyl)piperazinyl)-2-oxoethyl (2S)-2-(6-methoxy(2-naphthyl))propanoate hydrogen chloride To a solution of the product of Example 37b (0.3 g, 0.67 mmol) in EtOAc (4.3 mL) at 0° C. was added drop-wise a solution of HCl gas in Et$_2$O (24 mg, 0.33 mL, 2M solution, 0.67 mmol). The cloudy solution was dissolved in excess EtOAc and hexane was added. The solvent was evaporated to a small volume. The precipitate was filtered, washed with hexane to give the title compound (0.3 g, 92% yield) as a white solid. Mp 129-131° C. $^1$H NMR (300 MHz, d$_6$-DMSO) δ 11.65-12.00 (bs, 1H), 7.73-7.82 (m, 3H), 7.44 (dd, J=1.4 and 8.6 Hz, 1H), 7.28-7.32 (m, 1H), 7.16 (dd, J=2.5 and 8.9 Hz, 1H), 4.78-4.97 (m, 4H), 4.22-4.45 (m, 1H), 4.03 (q, J=7.1 Hz, 1H), 3.87 (s, 3H), 3.80-4.05 (m, 1H), 3.35-3.67 (m, 5H), 2.90-3.30 (m, 3H), 1.52 (d, J=7.1 Hz, 3H). $^{13}$C NMR (75 MHz, d$_6$-DMSO) δ 173.5, 165.0, 157.2, 135.5, 133.3, 129.1, 128.4, 126.9, 126.5, 125.8, 118.7, 105.7, 67.4, 61.4, 55.2, 50.8, 18.7. Mass spectrum (API-TIS) m/z 446 (MH$^+$). Anal. calcd. for C$_{22}$H$_{28}$ClN$_3$O$_7$: C, 54.83; H, 5.86; N, 8.72. Found: C, 54.78; H, 5.89; N, 8.65.

Example 38

3-((2S)-2-(6-Methoxy(2-naphthyl)propanoyloxy)-2-methyl-2-((nitrooxy)methyl)propyl(2S)-2-(6-methoxy(2-naphthyl)propanoate 38a. 2-(((2S)-2-(6-Methoxy(2-naphthyl)propanoyloxy)methyl)-3-hydroxy-2-methylpropyl (2S)-2-(6-methoxy(2-naphthyl))propanoate To a stirred solution of 1,1,1-tris(hydroxymethyl)ethane (1.32 g, 11 mmol), (2S)-2-(6-methoxy(2-naphthyl))propanoic acid (naproxen, 5.07 g, 22 mmol) and 1,3-dicyclohexylcarbodiimide (4.54 g, 22 mmol) in acetonitrile (100 mL) was added N,N-dimethylaminopyridine (DMAP, 10 mg). The reaction mixture was stirred at ambient temperature for 15 hours, filtered, and the filtrate was concentrated. The crude product was purified by chromatography on silica gel eluting with EtOAc:hexane (1:1) to give the title compound (4.36 g, 72% yield) as a white solid. Mp 96° C. $^1$H NMR (300 MHz, CDCl$_3$) δ 7.71-7.63 (m, 6H), 7.37-7.33 (m, 2H), 7.17-7.10 (m, 4H), 3.99-3.82 (m, 12H), 3.11 (t, J=6.7 Hz, 2H), 2.26 (t, J=6.7 Hz, 1H), 1.58-1.54 (m, 6H), 0.70 (s, 3H). $^{13}$C NMR (75 MHz, CDCl$_3$) δ 174.72, 174.66, 157.57, 135.24, 135.20, 133.62, 129.16, 128.77, 127.13, 125.97, 125.84, 118.98, 105.49, 66.01, 65.97, 64.35, 55.17, 45.35, 40.35, 18.04, 16.45. Mass spectrum (API-TIS) m/z 562.4 ((M+NH$_4$)$^+$).

38b. 3-((2S)-2-(6-Methoxy(2-naphthyl)propanoyloxy)-2-methyl-2-((nitrooxy)methyl)propyl (2S)-2-(6-methoxy(2-naphthyl)propanoate Fuming nitric acid (90%, 1.00 mL, 21 mmol) was added drop-wise to acetic anhydride (3 mL) at 0° C. with stirring. After 15 min, a precooled solution of the product of Example 38a (2.72 g, 5.00 mmol) in THF (30 mL) was added. The mixture was stirred at the same temperature for 20 minutes, EtOAc added, washed with aqueous NaHCO$_3$ (2×), dried over Na$_2$SO$_4$, filtered, and concentrated. The residue was purified by chromatography on silica gel eluting with EtOAc: hexane (1:2) to give the title compound (2.55 g, 87% yield) as a white solid. Mp 88-89° C. $^1$H NMR (300 MHz, CDCl$_3$) δ 7.68-7.59 (m, 6H), 7.31-7.27 (m, 2H), 7.15-7.08 (m, 4H), 4.02-3.77 (m, 14H, 1.54 (d, J=2.5 Hz, 3H), 1.51 (d, J=2.5 Hz, 3H), 0.74 (s, 3H). $^{13}$C NMR (75 MHz, CDCl$_3$) δ 173.88, 173.85, 157.65, 135.09, 133.69, 129.18, 128.81, 127.21, 125.91, 125.86, 119.07, 105.53, 65.39, 65.24, 55.23, 45.28, 38.69, 17.93, 16.77. Mass spectrum (API-TIS) m/z 607.4 ((M+NH$_4$)$^+$).

Example 39

2-(4-(2-(Nitrooxy)ethoxy)phenoxy)ethyl(2S)-2-(6-methoxy(2-naphthyl))propanoate

39a. 2-(4-(2-Hydroxyethoxy)phenoxy)ethyl(2S)-2-(6-methoxy(2-naphthyl))propanoate A solution of (2S)-2-(6-methoxy(2-naphthyl))propanoic acid (naproxen, 4.27 g, 18.5 mmol), hydroquinone bis(2-hydroxyethyl)ether (10.6 g, 53.3 mmol), N,N-dimethylaminopyridine (DMAP, 2.71 g, 22.2 mmol), 1-(3-dimethylaminopropyl)-3-ethylcarbodiimide hydrochloride (9.34 g, 48.7 mmol) and $NEt_3$ (13 mL, 93.3 mmol) in DMF (100 mL) was stirred at ambient temperature overnight. The reaction mixture was evaporated to dryness under vacuum and the residue was partitioned between HCl (3N, 100 mL) and $CH_2Cl_2$ (200 mL). The organic layer was washed with water, brine, dried over $Na_2SO_4$, filtered and concentrated. The product was separated by silica gel column chromatography eluting with EtOAc/hexane (1:1, Rf=0.15) and then recrystallized from ethyl ether and hexane to give the title compound as a white solid (6.01 g, 31% yield). Mp 76-78° C. $^1$H NMR ($CDCl_3$) δ 7.7-7.64 (m, 3H), 7.42-7.38 (m, 1H), 7.15-7.08 (m, 2H), 6.74-6.72 (m, 4H), 4.45-4.36 (m, 2H), 4.1-3.85 (m, 7H), 3.90 (s, 3H), 2.13 (br. t, 1H), 1.58 (d, J=7.2 Hz, 3H). $^{13}$C NMR ($CDCl_3$) δ 174.6, 157.5, 153.0, 152.8, 135.4, 133.6, 129.2, 128.8, 127.1, 126.1, 125.9, 118.8, 115.7, 115.3, 105.5, 69.7, 66.6, 63.1, 61.4, 55.2, 45.2, 18.4. MS (API) m/z 428 $(M+NH_4)^+$. Anal. calcd. for $C_{24}H_{26}O_6$: C, 70.23; H, 6.38. Found: C, 70.01; H, 6.39.

39b. 2-(4-(2-(Nitrooxy)ethoxy)phenoxy)ethyl(2S)-2-(6-methoxy(2-naphthyl))-propanoate To a solution of Example 39a (3.76 g, 9.2 mmol) in $CH_2Cl_2$ (50 mL) was added $NEt_3$ (1.4 mL, 10.0 mmol) and methanesulfonyl chloride (0.9 mL, 11.6 mmol) and stirred at ambient temperature for 2 hours. The reaction was quenched with HCl (3N, 50 mL) and extracted with $CH_2Cl_2$ (50 mL×2). The combined extracts were washed with HCl (3N), water, brine, dried over $Na_2SO_4$, filtered, concentrated and dry under vacuum to give a crude product, (methanesulfonate, that was used without purification). Tetrabutylammonium nitrate (5.61 g, 18.4 mmoL) was added to the crude product and the mixture heated to reflux in toluene (100 mL) overnight. The reaction was cooled to ambient temperature and partitioned between ethyl acetate (100 mL) and water (100 mL×4), dried over $Na_2SO_4$, filtered and concentrated. The product was separated by silica gel column chromatography eluted with EtOAc/hexane (1:3, Rf=0.25) and then recrystallized from ethyl ether and hexane to obtained the title compound as a white solid (2.17 g, 52% yield for 2 steps). Mp 67-69° C. $^1$H NMR (300 MHz, $CDCl_3$) δ 7.7-7.64 (m, 3H), 7.42-7.38 (m, 1H), 7.14-7.08 (m, 2H), 6.73-6.72 (m 4H), 4.79-4.75 (m, 2H), 4.41-4.37 (m, 2H), 4.17-4.01 (m, 4H), 3.90 (s, 3H), 3.89 (q, J=7.2 Hz, 1H), 1.58 (d, J=7.2 Hz, 3H). $^{13}$C NMR (75 MHz, $CDCl_3$) δ 174.5, 157.6, 153.2, 152.3, 135.4, 133.6, 129.2, 128.8, 127.1, 126.2, 125.9, 118.9, 115.8, 115.5, 105.5, 71.1, 66.6, 64.6, 63.1, 55.2, 45.2, 18.5. Mass spectrum (API-TIS) m/z 473 $(M+NH_4)^+$. Anal. calcd. for $C_{24}H_{25}NO_8$: C, 63.29; H, 5.53; N, 3.08. Found: C, 63.08; H, 5.38; N, 2.78.

Example 40

2-((2S)-2-(6-Methoxy(2-naphthyl))propanoyloxy)ethyl 3-(nitrooxy)-propyl ethane-1,2-dioate

40a. 3-(Nitrooxy)propan-1-ol

A solution of 3-bromo-1-propanol (5.42 g, 39.0 mmol) in acetonitrile (20 mL) was added to a solution of $AgNO_3$ (10.16 g, 59.8 mmol) in acetonitrile (50 mL) and stirred at room temperature for 24 hours. To the reaction mixture was added brine (350 mL) and stirred for 1 hour. The silver salts were filtered off through Celite and the filtrate was extracted with $Et_2O$ (200 mL×3). The organic layer was washed with brine, dried over $Na_2SO_4$, filtered, concentrated and dried under vacuum to give the title compound (4.08 g, 86% yield, >95% purity) that was used in the next step without purification. $^1$H NMR (300 MHz, $CDCl_3$) δ 4.61 (t, J=6.4 Hz, 2H), 3.78 (t, J=6.4 Hz, 2H), 1.99 (m, 2H). $^{13}$C NMR (75 MHz, $CDCl_3$) δ 70.3, 58.5, 29.5.

40b. 2-Hydroxyethyl(2S)-2-(6-methoxy(2-naphthyl))-propanoate

A solution of (2S)-2-(6-methoxy(2-naphthyl))propanoic acid sodium salt (10.9 g, 43.2 mmol) and 2-bromoethanol (27.11 g, 0.22 mol) in DMF (150 mL) was heated to 80° C. for 3.5 hours. The excess 2-bromoethanol and DMF were evaporated under vacuum at 60° C. The resulted crude material was dissolved in $CH_2Cl_2$ (400 mL) and washed with water (400 mL), saturated $NaHCO_3$ (100 mL), 3N HCl (100 mL), brine and dried over $Na_2SO_4$, filtered and concentrated. Trituration of the residue with ether/hexane gave the title compound as a white solid (9.97 g, 84% yield). m.p. 72-73° C. $^1$H NMR (300 MHz, $CDCl_3$) δ 8.0-7.68 (m, 3H), 7.66-7.61 (m, 1H), 7.16-7.1 (m, 2H), 4.25-4.15 (m, 2H), 3.93 (s, 3H), 3.92 (q, J=7.2 Hz, 1H), 3.75-3.70 (m, 2H), 1.78 (br. t, 1H), 1.59 (d, J=7.2 Hz, 3H). $^{13}$C NMR (75 MHz, $CDCl_3$) δ 174.7, 157.3, 135.2, 133.4, 129.9, 128.6, 126.9, 125.8, 125.6, 118.6, 105.3, 65.9, 60.3, 54.8, 45.0, 18.2. MS (API) m/z 275 $(M+NH_4)^+$.

40c. 2-((2S)-2-(6-Methoxy(2-naphthyl))propanoyloxy)ethyl 3-(nitrooxy)propyl ethane-1,2-dioate A solution of the product of Example 40a (1.36 g, 11.2 mmol) was added to a mixture of oxalyl chloride (3 mL, 34.4 mmol) and $Na_2CO_3$ (2.86 g, 27.0 mmol) in $CH_2Cl_2$ (50 mL) and stirred at ambient temperature for 3 hours. The resulting mixture was evaporated to dryness under reduced pressure. A solution the product of Example 40b (2.78 g, 10.1 mmol) in $CH_2Cl_2$ (50 mL) was added to the resulted mixture and then heated to reflux for 2 hours. After cooled to ambient temperature, $Na_2CO_3$ was removed by filtration and washed with $CH_2Cl_2$ (100 mL). The filtrate was washed with 3N HCl, water and brine, dried over $Na_2SO_4$, filtered, and concentrated. The product was purified by silica gel column chromatography eluting with EtOAc/hexane (2:3, Rf=0.25) to give the title compound as an oil (2.49 g, 55% yield). The oil solidified after standing for 2 weeks at ambient temperature. Mp 55-58° C. $^1$H NMR (300 MHz, $CDCl_3$) δ 7.7-7.64 (m, 3H), 7.4-7.35 (m, 1H), 7.15-7.08 (m, 2H), 4.6-4.2 (m, 8H), 3.87 (s, 3H), 3.86 (q, J=7.2 Hz, 1H), 2.01 (m, 2H), 1.56 (d, J=7.2 Hz, 3H). $^{13}$C NMR (75 MHz, $CDCl_3$) δ 174.1, 157.5, 156.8, 135.1, 133.5, 129.1, 128.6, 127.0, 126.0, 125.8, 118.8, 105.3, 69.1, 64.3, 62.7, 61.4, 55.1, 45.0, 25.7, 18.2. Mass spectrum (API-TIS) m/z 467 $(M+NH_4)^+$.

Example 41

N-((2S)-2-(6-Methoxy(2-naphthyl))propanoylamino)-4 (nitrooxy)butanamide

41a. 1,3-Dioxobenzo(c)azolidin-2-yl(2S)-2-(6-methoxy(2-naphthyl))propanoate A mixture of N-hydroxyphthalimide (7.1 g, 43.4 mmol), (2S)-2-(6-methoxy(2-naphthyl))propanoic acid (naproxen, 10 g, 43.4 mmol) and N,N-dimethylaminopyridine (DMAP, 5.3 g, 43.4 mmol) in $CH_2Cl_2$ (70 mL) and DMF (30 mL) at 0° C. was treated with 1-(3-(dimethylamino)propyl)-3-ethylcarbodiimide hydrochloride (8.3 g, 43.4 mmol) in $CH_2Cl_2$ (50 mL). The reaction mixture was stirred at room temperature for 16 hours and the solvent was evaporated under vacuum. The residue was then dissolved in EtOAc, washed with brine, dried over $Na_2SO_4$ and filtered. The residue after evaporation of the solvent was chromatographed on silica gel eluting with EtOAc:hexane (1:1) to give the title compound (7.6 g, 47% yield) as a white solid. Mp 110-112° C. $^1$H NMR (300 MHz, $d_6$-DMSO) δ 7.80-8.06 (m, 7H), 7.50 (dd, J=1.7 and 8.5 Hz, 1H), 7.32-7.37 (m, 1H), 7.20 (dd, J=2.5 and 9.0 Hz, 1H), 4.50 (q, J=7.1 Hz, 1H), 3.89 (s, 3H), 1.64 (d, J=7.1 Hz, 3H). $^{13}$C NMR (75 MHz, $d_6$-DMSO) δ 171.2, 161.8, 157.5, 153.0, 135.5, 133.6, 133.5, 129.3, 128.4, 128.2, 127.3, 126.1, 126.0, 124.0, 119.0, 105.8, 55.2, 41.8, 18.6. Mass spectrum (API-TIS) m/z 376 ($MH^+$), 393 ($MNH_4^+$).

41b. (2S)-2-(6-Methoxy(2-naphthyl))propanohydrazide

Hydrazine monohydrate (1.7 g, 1.7 mL, 53.3 mmol) was added drop-wise to a solution of the product of Example 41a (5 g, 13.3 mmol) in $CH_2Cl_2$ (30 mL) and methanol (2.4 mL) at room temperature. The resultant suspension was stirred at room temperature for 30 minutes. The residue after evaporation of the solvent was dissolved in 5% $Na_2CO_3$, extracted with EtOAc. The organic layer was washed with brine, dried over anhydrous $Na_2SO_4$ and filtered. The residue after evaporation of the solvent was chromatographed on silica gel eluting with MeOH:EtOAc:hexane (0.1:1:1) to give the title compound (1.7 g, 52% yield) as a white solid. Mp 106-108° C. $^1$H NMR (300 MHz, $d_6$-DMSO) δ 7.69-7.78 (m, 3H), 7.45 (dd, J=1.6 and 8.4 Hz, 1H), 7.24-7.28 (m, 1H), 7.13 (dd, J=2.5 and 8.9 Hz, 1H), 4.15-4.24 (bs, 2H), 3.85 (s, 3H), 3.65 (q, J=7.1 Hz, 1H), 1.41 (d, J=7.0 Hz, 3H). $^{13}$C NMR (75 MHz, $d_6$-DMSO) δ 172.9, 157.0, 137.2, 133.1, 129.1, 128.3, 126.5, 125.3, 118.6, 105.6, 55.1, 43.2, 18.3. Mass spectrum (API-TIS) m/z 245 ($MH^+$).

41c. N-((2S)-2-(6-Methoxy(2-naphthyl))propanoylamino)-4-hydroxybutanamide

A mixture of γ-butyrolactone (0.78 g, 0.7 mL, 9.1 mmol) and the product of Example 41b (1.12 g, 4.57 mmol) in THF (3 mL) was heated at 120° C. for 3 hours. The precipitate was filtered. The residue after evaporation of the filtrate was chromatographed on silica gel eluting with MeOH:EtOAc:hexane (0.1:1:1) to give the title compound (0.25 g, 17% yield) as a white solid. Mp 149-151° C. $^1$H NMR (300 MHz, $d_6$-DMSO) δ 9.82-9.95 (bs, 1H), 9.45-9.60 (bs, 1H), 7.71-7.82 (m, 3H), 7.47 (d, J=8.6 Hz, 1H), 7.24-7.29 (m, 1H), 7.14 (dd, J=2.5 and 8.9 Hz, 1H), 4.45 (t, J=5.2 Hz, 1H), 3.86 (s, 3H), 3.80 (q, J=7.0 Hz, 1H), 3.31-3.41 (m, 2H), 2.12 (t, J=7.3 Hz, 2H), 1.56-1.70 (m, 2H), 1.43 (d, J=7.0 Hz, 3H). $^{13}$C NMR (75 MHz, $d_6$-DMSO) δ 172.3, 171.1, 157.0, 136.7, 133.2, 129.1, 128.3, 126.6, 125.4, 118.6, 105.7, 60.1, 55.2, 42.9, 29.9, 28.4, 18.4. Mass spectrum (API-TIS) m/z 329 (M–H), 331 ($MH^+$), 313 (M–OH), 353 ($MNa^+$).

41d. N-((2S)-2-(6-Methoxy(2-naphthyl))propanoylamino)-4-(nitrooxy)butanamide A suspension of the product of Example 41c (0.23 g, 0.69 mmol) in EtOAc (6.5 mL) was added drop-wise to a mixture of fuming $HNO_3$ (0.22 g, 146 μL, 3.48 mmol) and $Ac_2O$ (0.56 g, 0.53 mL, 5.56 mmol) at 0° C. The reaction mixture was stirred at 0° C. for 1 hour, diluted with EtOAc and washed with ice cold saturated $NaHCO_3$, water and dried over $Na_2SO_4$. The residue after filtration and evaporation was chromatographed on silica gel eluting with MeOH:EtOAc:hexane (0.1:1:1) to give the title compound (0.1 g, 38% yield) as a pale yellow solid. Mp 117-119° C. $^1$H NMR (300 MHz, $CDCl_3$) δ 8.95-9.11 (bs, 1H), 8.55-8.67 (bs, 1H), 7.62-7.74 (m, 3H), 7.36 (dd, J=1.7 and 8.5 Hz, 1H), 7.06-7.18 (m, 2H), 4.38 (t, J=6.3 Hz, 2H), 3.90 (s, 3H), 3.79 (q, J=7.1 Hz, 1H), 2.26 (t, J=6.9 Hz, 2H), 1.95 (p, J=6.6 Hz, 2H), 1.60 (d, J=7.1 Hz, 3H). $^{13}$C NMR (75 MHz, $CDCl_3$) δ 171.4, 168.5, 158.0, 135.0, 134.1, 129.4, 129.1, 127.8, 126.4, 126.1, 119.5, 105.8, 72.1, 55.5, 44.9, 29.6, 22.5, 18.4. Mass spectrum (API-TIS) m/z 376 ($MH^+$), 398 ($MNa^+$).

Example 42

4-((2S)-2-(6-Methoxy(2-naphthyl))propanoyloxy) (2S,3S)-2,3-bis(nitrooxy)butyl(2S)-2-(6-methoxy(2-naphthyl))propanoate and (2S,3S)-2,3-Bis(nitrooxy)-4-hydroxybutyl(2S)-2-(6-methyoxy(2-naphthyl))propanoate

42a. (2S,3S)-1,4-Bis(1,1,2,2-tetramethyl-1-silapropoxy)butane-2,3-diol

To L-threitol (4.8958 g, 40.090 mmol) and triethylamine (8.93 g, 88 mmol) in DMF (100 mL) was added t-butyldimethylsilyl chloride (12.0851 g, 80.177 mmol) at 0° C. The reaction mixture was stirred at room temperature for 0.5 hour, and filtered. The filtrate was concentrated to dryness. The resultant product was dissolved in EtOAc, washed with water, and brine. The organic phase was dried over magnesium sulfate, filtered, and concentrated. The product was chromatographed on silica gel eluting with MeOH:$CH_2Cl_2$ (0:100, 0.5:99.5, 1:99, 2:98, 3:97) to give the title compound (8.592 g, 61% yield). $^1$H NMR (300 MHz, $CDCl_3$) δ 3.77-3.70 (m, 6H), 2.87-2.84 (m, 2H), 0.90 (s, 18H), 0.08 (s, 12H). $^{13}$C NMR (75 MHz, $CDCl_3$) δ71.4, 65.0, 25.8, 18.2, −5.47. APIMS (IS, $NH_4OAc$) m/z 351 ($M+H^+$), 368 ($M+NH_4^+$), 373 ($M+Na^+$), 718 ($2M+NH_4^+$).

42b. (2S,3S)-(1,4-Bis(1,1,2,2-tetramethyl-1-silapropoxy))-(2,3-bis(nitrooxy))butane-2,3-diol To acetic anhydride (22.7 g, 222 mmol) at 0° C. was slowly added fuming nitric acid (100%, 11.9 g, 189 mmol) over a period of 10 minutes. The resultant solution was stirred at 0° C. for 0.5 hour. The product of Example 42a (5.4119 g, 15.434 mmol) in THF (25 mL) was added. The reaction mixture was stirred at room temperature for 50 minutes, concentrated. The product was treated with EtOAc, and washed with water. The organic phase was dried over magnesium sulfate, filtered, and concentrated. The product was chromatographed on silica gel eluting with $CH_2Cl_2$:hexane (1:4) to give the title compound (6.40 g, 94% yield). $^1$H NMR (300

MHz, CDCl$_3$) δ 5.41-5.39 (m, 2H), 3.90-3.89 (m, 4H), 0.89 (s, 18H), 0.07 (s, 12H). $^{13}$C NMR (75 MHz, CDCl$_3$) δ79.5, 60.2, 25.6, 18.1, −5.68. APIMS (IS, NH$_4$OAc) m/z 441 (M+H$^+$), 458 (M+NH$_4^+$), 898 (2M+NH$_4^+$).

42c. (2S,3S)-2,3-Bis(nitrooxy)butane-1,4-diol

To the product of Example 42b (5.82 g, 13.21 mmol) in THF (150 mL) under argon at 0° C. was added acetic acid (2.99 mg, 49.8 mmol) and then tetrabutylammonium fluoride (1.0 M, 26.6 mmol). The reaction mixture was stirred at room temperature for 1.5 hours, and concentrated to dryness. The resultant product was dissolved in EtOAc and washed with water, and brine. The organic phase was dried over magnesium sulfate, filtered, and concentrated. The resultant product was chromatographed on silica gel eluting with MeOH: CH$_2$Cl$_2$ (1.5:98.5, 3:97) to give the title compound (2.28 g, 81% yield). $^1$H NMR (300 MHz, CDCl$_3$) δ 5.46-5.36 (m, 2H), 4.07-3.96 (m, 4H). $^{13}$C NMR (75 MHz, CDCl$_3$) δ 79.6, 60.2. APIMS (IS, NH$_4$OAc) m/z 230 (M+NH$_4^+$). APIMS (IS, NH$_4$OAc) m/z 211 (M−H$^−$).

42d. 4-((2S)-2-(6-Methoxy(2-naphthyl))propanoyloxy)(2S,3S)-2,3-bis(nitrooxy)butyl(2S)-2-(6-methoxy(2-naphthyl))propanoate and (2S,3S)-2,3-Bis(nitrooxy)-4-hydroxybutyl(2S)-2-(6-methyoxy(2-naphthyl))propanoate To the product of Example 42c (1.8502 g, 8.7224 mmol) in THF (50 mL) was added (2S)-2-(6-methoxy(2-naphthyl)) propanoic acid (naproxen, 2.305 g, 10.010 mmol), N,N-dimethylaminopyridine (DMAP, 1.01 g, 8.21 mmol). To the resulting solution was added N,N-dicyclohexylcarbodiimide (2.07 g, 10.02 mmol) in CH$_2$Cl$_2$ (10 mL). The reaction mixture was stirred at room temperature overnight and filtered. The filtrate was concentrated to dryness. The resultant product was dissolved in EtOAc, washed with citric acid (0.2 M), brine, dried over magnesium sulfate, filtered, and concentrated. The resultant product was chromatographed on silica gel eluting with MeOH:CH$_2$Cl$_2$ (0:100, 0.5:99.5, 1:99, 1.5: 98.5, 2:98) to give 4-((2S)-2-(6-methoxy(2-naphthyl))propanoyloxy)(2S,3S)-2,3-bis(nitrooxy)butyl(2S)-2-(6-methoxy(2-naphthyl))propanoate (2.01 g, 36% yield) and (2S,3S)-2,3-bis(nitrooxy)-4-hydroxybutyl(2S)-2-(6-methyoxy(2-naphthyl))propanoate (1.25 g, 34% yield). $^1$H NMR (300 MHz, CDCl$_3$) δ 7.70-7.67 (m, 4H), 7.60-7.59 (m, 2H), 7.31-7.26 (m, 2H), 7.16-7.10 (m, 4H), 5.07-5.01 (m, 2H), 4.39-4.33 (m, 2H), 4.03-3.97 (m, 2H), 3.91 (s, 6H), 3.80 (q, J=7.1 Hz, 2H), 1.59 (d, J=7.2 Hz, 6H). $^{13}$C NMR (75 MHz, CDCl$_3$) δ 173.67, 157.8, 134.4, 133.8, 129.2, 128.8, 127.4, 126.0, 125.8, 119.2, 105.6, 76.5, 60.2, 55.3, 45.1, 17.9. APIMS (IS, NH$_4$OAc) m/z 637 (M+H$^+$), 654 (M+NH$_4^+$), 659 (M+Na$^+$).

$^1$H NMR (300 MHz, CDCl$_3$) δ 7.73-7.69 (m, 2H), 7.64-7.63 (m, 1H), 7.37-7.33 (m, 1H), 7.17-7.11 (m, 2H), 5.48-5.42 (m, 1H), 5.02-4.97 (m, 1H), 4.59 (dd, J=12.8 Hz & 3.6 Hz, 1H), 4.22 (dd, J=12.8 Hz & 5.2 Hz, 1H), 3.91 (s, 3H), 3.91-3.84 (m, 1H), 3.77-3.64 (m, 2H), 1.99 (s, 1H), 1.54 (d, J=7.1 Hz, 3H). $^{13}$C NMR (75 MHz, CDCl$_3$) 6174.0, 157.8, 134.5, 133.8, 129.2, 128.8, 127.4, 126.0, 125.8, 119.2, 105.6, 79.2, 76.9, 60.8, 59.7, 55.3, 45.3, 17.9. APIMS (IS, NH$_4$OAc) m/z 425 (M+H$^+$), 442 (M+NH$_4^+$), 447 (M+Na$^+$).

Example 43

2-((3-((Nitrooxy)methyl)phenyl)carbonylamino) ethyl(2S)-2-(6-methoxy(2-napthyl propanoate 43a. 3-((Nitrooxy)methyl)benzoic acid A solution of silver nitrate (12.98 g, 76.4 mmol) and 3-(chloromethyl)benzoic acid (6.53 g, 76.4 mmol) in acetonitrile (160 mL) was heated to 75° C. overnight. The reaction mixture was then cooled to ambient temperature and stirred with brine (100 mL) for 1 hour. The resulting mixture was filtered through Celite and washed with water. The filtrate was concentrated and then extracted with CH$_2$Cl$_2$. The combined organic extracts were washed with water, brine, dried over Na$_2$SO$_4$, filtered, concentrated and dried under vacuum. The crude product was washed with Et$_2$O/hexane (15:85) and then dried under vacuum to obtain the title compound as a white solid (6.08 g, 80% yield). Mp 123-125° C. $^1$H NMR (300 MHz, CDCl$_3$) δ 8.18-8.14 (m, 2H), 7.68-7.57 (m, 1H), 7.55 (t, J=8.1 Hz, 1H), 5.50 (s, 2H). $^{13}$C NMR (75 MHz, CDCl$_3$) δ 166.9, 133.6, 133.0, 131.3, 130.1, 74.5. Mass spectrum (API-TIS) m/z 196 (M−H)$^−$. Anal. calcd. for C$_8$H$_7$NO$_5$: C, 48.74; H, 3.58; N, 7.10. Found: C, 48.84; H, 3.54; N, 6.85.

43b. 2-((tert-Butoxy)carbonylamino)ethyl(2S)-2-(6-methoxy(2-naphthyl))propanoate A solution of (2S)-2-(6-methoxy(2-naphthyl))propanoic acid (naproxen, 7.60 g, 33.0 mmol), tert-butyl N-(2-hydroxyethyl)carbamate (5.30 g, 32.9 mmol), N,N-dimethylaminopyridine (DMAP, 0.35 g, 2.86 mmol) and 1,3-dicyclohexylcarbodiimide (6.80 g, 33.0 mmol) in CH$_2$Cl$_2$ (200 mL) was stirred at ambient temperature overnight. The byproduct, dicyclohexyl urea, was removed by filtration. The filtrate was concentrated, dissolved in EtOAc (50 mL) and then cooled in a dry-ice bath to precipitate the remaining dicyclohexyl urea and then filtered. The filtrate was concentrated, dissolved in CH$_2$Cl$_2$ (15 mL) and hexane (200 mL) and then stirred until the product precipitated. The solid was dried under vacuum to give the title compound (10.12 g, 82% yield). Mp 82-84° C. $^1$H NMR (300 MHz, CDCl$_3$) δ 7.72-7.65 (m, 3H), 7.42-7.38 (m, 1H), 7.16-7.11 (m, 2H), 5.05 (br, 1H), 4.13 (t, J=5.3 Hz, 2H), 3.91 (s, 3H), 3.87 (q, J=7.1 Hz, 1H), 3.30 (br. q, 2H), 1.58 (d, J=7.1 Hz, 3H), 1.45 (s, 9H). $^{13}$C NMR (75 MHz, CDCl$_3$) δ 174.4, 157.6, 155.6, 135.4, 133.6, 129.2, 128.8, 127.1, 126.0, 125.8, 119.0, 105.5, 79.3, 63.7, 55.2, 45.2, 39.5, 28.2, 18.3. Mass spectrum (API-TIS) m/z 374 (MH)$^+$. Anal. calcd. for C$_{21}$H$_{27}$NO$_5$: C, 67.54; H, 7.29; N, 3.75. Found: C, 67.43; H, 7.16; N, 3.66.

43c. 2-Aminoethyl(2S)-2-(6-methoxy(2-naphthyl)) propanoate hydrochloride

A solution of HCl/Et$_2$O (9.4 g/50 mL) was added to the product of Example 43b (4.85 g, 13.0 mmol) and stirred at ambient temperature overnight. The resulted white solid was filtered and washed with Et$_2$O and then dried under vacuum to give the title compound (3.79 g, 94% yield). Mp 184-186° C. $^1$H NMR (300 MHz, d$_6$-DMSO) δ 8.28 (br, 3H), 7.83-7.74 (m, 3H), 7.44 (dd, J=8.7, 1.8 Hz, 1H), 7.30 (d, J=2.7 Hz, 1H), 7.16 (dd, J=9.0, 2.7 Hz, 1H), 4.31 (m, 1H), 4.13 (m, 1H), 3.99 (q, J=7.2 Hz, 1H), 3.87 (s, 3H), 3.05 (br. q, 2H), 1.51 (d, J=7.2 Hz, 3H). $^{13}$C NMR (75 MHz, d$_6$-DMSO) δ 173.9, 157.2, 135.5, 133.4, 129.2, 128.4, 127.0, 126.4, 125.8, 118.8, 105.7, 60.9, 55.2, 44.3, 37.6, 18.4. Mass spectrum (API-TIS) m/z 274 (MH)$^+$.

43d. 2-((3-((Nitrooxy)methyl)phenyl)carbonylamino)ethyl(2S)-2-(6-methoxy(2-naphthyl))propanoate A solution of the product of Example 43c (1.76 g, 5.7 mmol), the product of Example 43a (1.06 g, 5.4 mmol), N,N-dimethylaminopyridine (DMAP, 0.14 g, 1.1 mmol), 1-(3-dimethylaminopropyl)-3-ethylcarbodiimide hydrochloride (1.27 g, 6.6 mmol) and NEt$_3$ (2.5 mL, 17.9 mmol) in CH$_2$Cl$_2$ (50 mL) was stirred at ambient temperature overnight. The reaction mixture was partitioned between 3N HCl (100 mL) and CH$_2$Cl$_2$ (200 mL×2). The combined organic extracts were back washed with water, brine, dried over Na$_2$SO$_4$, filtered, concentrated and dried under vacuum. The product was separated by silica gel column chromatography eluting with EtOAc:hexane (1:1, Rf=0.22) to give the title compound as a white solid (0.46 g, 19% yield). Mp 92-94° C. $^1$H NMR (300 MHz, CDCl$_3$) δ 7.63-7.58 (m, 4H), 7.41-7.03 (m, 6H), 6.40 (br, 1H), 5.27 (s, 2H), 4.32-4.21 (m, 2H), 3.88 (s, 3H), 3.87 (q, J=7.2 Hz, 1H), 3.29 (br. q, 2H), 1.56 (d, J=7.2 Hz, 3H). $^{13}$C NMR (75 MHz, CDCl$_3$) δ 174.8, 166.5, 157.6, 135.4, 134.5, 133.5, 132.6, 131.5, 129.1, 128.8, 128.7, 127.6, 127.3, 127.2, 126.3, 125.8, 125.7, 119.0, 105.5, 73.9, 63.1, 55.2, 45.2, 39.2, 18.1. Mass spectrum (API-TIS) m/z 453 (MH)$^+$.

Example 44

(2R)-2-(nitrooxy)-3-(phenylmethoxy)propyl(2S)-2-(6-methoxy(2-naphthyl))propanoate 44a. (2R)-2-hydroxy-3-(phenylmethoxy)propyl(2S)-2-(6-methoxy(2-naphthyl))propanoate A solution of (2S)-2-(6-methoxy(2-naphthyl))propanoic acid (naproxen, 3.70 g, 16.1 mmol), (R)-(+)-3-benzyloxy-1,2-propanediol (2.92 g, 19.0 mmol), N,N-dimethylaminopyridine (DMAP, 0.40 g, 3.3 mmol) and 1,3-dicyclohexylcarbodiimide (3.61 g, 17.5 mmol) in CH$_2$Cl$_2$ (120 mL) was stirred at ambient temperature overnight. The byproduct, dicyclohexyl urea, was removed by filtration. The reaction mixture was partitioned between HCl (3N, 50 mL) and CH$_2$Cl$_2$ (50 mL×2). The combined organic extracts were back washed with water, brine, dried over Na$_2$SO$_4$, filtered, concentrated and dried under vacuum. The product was separated by silica gel column chromatography eluting with EtOAc:hexane (1:2, Rf=0.23) to give a mixture of the 1- and 2-glycerol ester isomers (88:12, 3.87 g). $^1$H NMR (300 MHz, CDCl$_3$) δ 7.69-7.64 (m, 3H), 7.40-7.03 (m, 8H), 5.34 (s, 2H), 4.17-4.14 (m, 2H), 3.88 (s, 3H), 3.9-3.85 (m, 2H), 3.33-3.28 (m, 2H), 2.45 (br. d, 1H), 1.56 (d, J=7.2 Hz, 3H). $^{13}$C NMR (75 MHz, CDCl$_3$) δ 174.6, 157.6, 137.6, 135.4, 133.6, 129.6, 129.2, 128.8, 128.3, 127.7, 127.61, 127.55, 127.1, 126.1, 125.9, 119.0, 105.5, 73.3, 70.6, 68.8, 65.5, 62.2, 55.2, 45.3, 18.3. Mass spectrum (API-TIS) m/z 412 (M+NH$_4$)$^+$.

44b. (2R)-2-(nitrooxy)-3-(phenylmethoxy)propyl (2S)-2-(6-methoxy(2-naphthyl))propanoate The title compound can be prepared following the procedure for Example 12.

Example 45

2-(N-Methyl(4-((nitrooxy)methyl)phenyl)carbonylamino)ethyl(2S)-2-(6-methoxy(2-naphthyl))propanoate 45a. (tert-Butoxy)-N-(2-hydroxyethyl)-N-methylcarboxamide 2-(Methylamino)ethanol (7.5 g, 0.1 mol) was dissolved in anhydrous THF (250 mL) and to this solution at room temperature was added di-t-butyldicarbonate (19.5 g, 0.1 mol) in THF (50 mL). The reaction mixture was stirred at room temperature overnight. The solvent was evaporated and the residue was extracted with EtOAc. The combined organic extracts were washed with water, brine, dried over sodium sulfate, and filtered. The filtrate was evaporated to give the title compound (16.5 g) as a colorless thick oil, $^1$HNMR (300 MHz, CDCl$_3$) δ 3.66 (m, 2H), 3.31 (br t, J=4.4 Hz, 2H), 2.85 (s, 3H), 1.39 (s, 9H).

45b. 2-((tert-Butoxy)-N-methylcarbonylamino)ethyl (2S)-2-(6-methoxy(2 naphthyl))propanoate To a solution of (2S)-2-(6-methoxy(2-naphthyl))propanoic acid (naproxen, 11.51 g, 50 mmol) and the product of Example 45a (7.5 g, 50 mmol) in anhydrous CH$_2$Cl$_2$ (300 mL) were added 1-ethyl-3-(3-dimethylaminopropyl)carbamide hydrochloride (EDAC, 9.55 g, 50 mmol) and N,N-dimethylaminopyridine (DMAP, 6.1 g, 50 mmol) at 0° C. under nitrogen atmosphere. The reaction mixture was stirred at room temperature for 24 hours. The solvent was removed and the residue was extracted with EtOAc, washed with water, brine, dried over sodium sulfate, filtered and evaporated. The product was purified by column chromatography on silica gel eluting with MeOH:CH$_2$Cl$_2$ (5:95) to give the title compound (17.1 g, 99% yield) as colorless thick oil. $^1$HNMR (300 MHz, CDCl$_3$) δ 7.69 (d, J=8.6 Hz, 2H), 7.64 (d, J=1.2 Hz, 1H), 7.05 (dd, J=8.5 and 1.2 Hz, 1H), 7.15 (m, 2H), 4.2 (m, 2H), 3.82 (s, 3H), 3.65 (q, J=7.2 Hz, 1H), 2.8 (m, 2H), 1.57 (d, J=7.2 Hz, 3H), 1.42 (s, 9H).

45c. 2-(Methylamino)ethyl(2S)-2-(6-methoxy(2-naphthyl))propanoate

The product of the Example 45b (17.1 g, 50 mmol) was dissolved in CH$_2$Cl$_2$ (400 mL). The solution was cooled to 0° C. and TFA (80 mL) was added drop-wise. The ice bath was removed and the reaction mixture was stirred at room temperature overnight, then the solvent. was evaporated. The residue was treated with aqueous sodium carbonate (10%) and extracted with EtOAc. The combined organic extracts were washed with water, brine, dried over sodium sulfate, and the solvent was evaporated. Trituration of the resulting solid with hexane gave the pure product as a white solid. Mp 64-68° C. $^1$HNMR (300 MHz, CDCl$_3$) δ 7.67 (d, J=8.5 Hz, 2H), 7.66 (d, J=1.3, 1H), 7.4 (dd, J=8.5 and 1.8 Hz, 1H), 7.18-7.08 (m, 2H), 4.18 (t, J=5.4 Hz, 2H), 3.89 (s, 3H), 3.80 (q, J=7.1 Hz, 1H), 2.73 (t, J=5.4 Hz, 2H), 2.31 (s, 3H), 1.56 (d, J=7.1 Hz, 3H); $^{13}$C NMR (75 MHz, CDCl$_3$) δ 174.5, 157.6, 135.6, 133.6, 129.2, 128.8, 127.1, 126.1, 125.8, 118.9, 105.5, 63.9, 55.2, 50.0, 45.3, 36.0, 18.4.

45d. 2-(N-methyl(4-((nitrooxy)methyl)phenyl)carbonylamino)ethyl(2S)-2-(6-methoxy(2-naphthyl))propanoate To a solution of the product of Example 45c (1.0 g, 3.50 mmol) and the product of the Example 11a (1.03 g, 5.25 mmol) in anhydrous CH$_2$Cl$_2$ (17 mL) N,N-dimethylaminopyridine (DMAP, 430 mg, 3.50 mmol) and 1-(3-(dimethylamino)propyl)-3-ethylcarbodiimide hydrochloride (EDAC, 670 mg, 3.50 mmol) were added successively and the reaction mixture was stirred under an inert nitrogen atmosphere at room temperature for 5 hours. The reaction mixture was diluted with CH$_2$Cl$_2$ then washed with saturated aqueous NaHCO$_3$, aqueous KHSO$_4$ (5%), water, brine, dried over anhydrous Na$_2$SO$_4$, filtered and concentrated under reduced pressure. The residue was purified by silica gel column chromatography eluting with EtOAC:hexane (2:8, 1:1) to give the title compound (490 mg, 30% yield) as a white solid. Mp 108-115° C. $^1$HNMR (300 MHz, CDCl$_3$) δ 7.97 (d, J=8.1 Hz, 1H), 7.84 (d, J=8.2, 1H), 7.69-7.58 (m, 3H), 7.42 (d, J=8.4, 1H), 7.36-7.26 (m, 2H), 7.13-7.07 (m, 2H) 5.41 (s, 2H), 4.49-4.45 (m, 2H), 4.06-3.95 (m, 1H), 3.90 (s, 3H), 3.69-3.41 (m, 2H), 2.98 (s, 3H), 1.50-1.46 (m, 3H); $^{13}$C NMR (75 MHz, CDCl$_3$) δ 174.1, 165.6, 157.6, 137.2, 136.7, 133.5, 130.8, 130.0, 129.1, 129.1, 128.3, 127.5, 126.1, 125.7, 118.9, 105.7, 73.6, 62.6, 55.3, 47.5, 43.5, 36.8, 20.6; LRMS (APIMS) m/z 467 (M+H)$^+$.

Example 46

(1S,2S,5S,6R)-6-(Nitrooxy)-4,8-dioxabicyclo(3.3.0) oct-2-yl 2-(1-((4 chlorophenyl)carbonyl)-5-methoxy-2-methylindol-3-yl)acetate To a slurry of indomethacin (2.16 g, 6.04 mmol) and (2S)-7-(nitrooxy)-4,8-dioxabicyclo(3.3.0)octan-2-ol (isosorbide 5-mononitrate, 1.21 g, 6.34 mmol, 1.05 eq) in CH$_2$Cl$_2$ (20 mL) at 0° C. were added were added 1-(3-(dimethylamino)propyl)-3-ethylcarbodiimide hydrochloride (EDAC, 1.27 g, 1.1 eq) and a catalytic amount of N,N-dimethylaminopyridine (DMAP). The reaction mixture was stirred at 0° C. for 30 minutes, and then at room temperature overnight, diluted with CH$_2$Cl$_2$ and washed H$_2$O, brine, dried over sodium sulfate, filtered and evaporated to give an off-white solid. The solid was recrystallized from CH$_2$Cl$_2$/EtOAc to give the title compound (2.0 g, 62% yield) as a white solid. Mp 159-160° C.; $^1$H NMR (300 MHz, CDCl$_3$) δ 7.66 (m, 2H), 7.48 (m, 2H), 6.93 (m, 1H), 6.88 (m, 1H), 6.68 (m, 1H), 5.33 (m, 1H), 5.23 (m, 1H), 4.91 (m, 1H), 4.41 (m, 1H), 3.95 (m, 4H), 3.83 (s, 3H), 3.68 (s, 2H), 2.37 (s, 3H); LRMS (APIMS) m/z 531 (M+1)$^+$, 548 (M+18)$^+$.

Example 47

(1S,2S,5S,6R)-6-(Nitrooxy)-4,8-dioxabicyclo(3.3.0) oct-2-yl 2-(2-((2,6-dichlorophenyl)amino)phenyl) acetate To a slurry of diclofenac (1.01 g, 3.41 mmol) and (2S)-7-(nitrooxy)-4,8-dioxabicyclo(3.3.0)octan-2-ol (isosorbide 5-mononitrate, 658 mg, 3.44 mmol, 1.01 eq) in CH$_2$Cl$_2$ (20 mL) at 0° C. were added dicyclohexylcarbodiimide (DCC, 3.58 mmol, 1.05 eq, 3.58 mL of a 1M solution in methylene chloride) and a catalytic amount of N,N-dimethylaminopyridine (DMAP). Dicyclohexylurea (DCU) precipitated almost immediately and the reaction mixture was stirred at room temperature for 3 hours. The reaction mixture was filtration through a small pad of Celite and the solid washed with CH$_2$Cl$_2$. The organic filtrate was washed with HCl (1N), sodium bicarbonate, water, brine, dried over sodium sulfate, filtered and the solvent removed in vacuo to give a sticky yellow oil. The oil was purified by flash chromatography on silica gel column eluted with CH$_2$Cl$_2$ to give the title compound (268 mg, 17% yield) as a white foam: $^1$H NMR (300 MHz, CDCl$_3$) δ 7.34 (m, 2H), 7.15 (m, 2H), 6.99 (m, 2H), 6.71 (bs, 1H), 6.57 (m, 1H), 5.35 (m, 1H), 5.28 (m, 1H), 4.95 (m, 1H), 4.47 (m, 1H), 4.04 (m, 3H), 3.88 (m, 1H), 3.83 (s, 2H); LRMS (APIMS) m/z 469 (M+1)$^+$.

Example 48

2-(((4-Methylphenyl)sulfonyl)(2-(nitrooxy)ethyl) amino)ethyl(2S)-2-(6-methoxy(2-naphthyl))propanoate 48a. 2-((2-Hydroxyethyl)((4-methylphenyl)sulfonyl) amino)ethyl(2S)-2-(6-methoxy(2-naphthyl))propanoate To a solution of (2S)-2-(6-methoxy(2-naphthyl))propanoic acid (naproxen, 5.0 g, 21.7 mmol), N,N-bis(2-hydroxyethyl)-p-toluenesulfonamide (16.89 g, 65.1 mmol) and N,N-dimethylaminopyridine (DMAP, 0.530 g, 4.34 mmol) in CH$_2$Cl$_2$ (250 mL) and DMF (3 mL) at room temperature was added 1-(3-(dimethylamino)propyl)-3-ethylcarbodiimide hydrochloride (EDAC, 4.99 g, 26.05 mmol). The reaction mixture was stirred overnight at room temperature, and then partitioned between CH$_2$Cl$_2$ and HCl (1N). The aqueous layer was washed with CH$_2$Cl$_2$ and the combined organic extracts were washed with water, brine, dried over magnesium sulfate and concentrated in vacuo. The residue was purified by column chromatography on silica gel eluting with EtOAC/hexane (1:1) to give the title compound as a thick oil (7.15 g, 15.16 mmol, 70% yield): $^1$H NMR (300 MHz, CDCl$_3$) δ 7.73 (d, J=8.6 Hz, 2H), 7.66 (m, 1H), 7.67 (d, J=8.6 Hz, 2H), 7.40 (dd, J=1.7, 8.5 Hz, 1H), 7.29 (d, J=8.1 Hz, 2H), 7.18 (dd, J=2.5, 8.8 Hz, 1H), 7.14 (d, J=2.4 Hz, 1H), 4.28 (m, 2H), 3.95 (s, 3H), 3.88 (q, J=7.2 Hz, 1H), 3.38 (m, 2H), 3.09 (t, J=5.1 Hz, 2H), 2.44 (s, 3H), 2.18 (t, J=6.0 Hz, 1H), 1.61 (d, J=7.2 Hz, 3H). Mass spectrum (API-TIS) m/z 472 (MH$^+$), 489 (M+18$^+$).

48b: 2-(((4-Methylphenyl)sulfonyl)(2-(nitrooxy) ethyl)amino)ethyl(2S)-2-(6-methoxy(2-naphthyl)) propanoate To acetic anhydride (5.6 mL, 60.6 mmol) at 0° C. was added fuming nitric acid (90%, 1.77 mL, 37.9 mmol) with stirring. The resulting mixture was stirred at room temperature for 25 min., then added drop-wise to a solution of the product of Example 48a, (7.15 g, 15.16 mmol) in EtOAc (20 mL) at 0° C. and was then stirred at 0° C. for 1 hour, and then poured into a 0° C. mixture of ethyl acetate (25 mL) and sodium bicarbonate (50 mL). The mixture was stirred at 0° C. for 20 min., then warmed to room temperature for 1 hour, partitioned between ethyl acetate and water, washed with sodium bicarbonate, water, brine and dried over sodium sulfate. The solvent was removed in vacuo, and the residue was purified by column chromatography on silica, eluting with EtOAc/hexane (1:1) to give the title compound as a pale yellow oil (6.92 g, 13.4 mmol, 88% yield). The oil solidified, and was recrystallized from dichloromethane/petroleum ether to give pale yellow needles. Mp 92-95° C. $^1$H NMR (300 MHz, CDCl$_3$) δ 7.69 (d, J=8.9 Hz, 2H), 7.63 (m, 1H), 7.62 (d, J=8.2 Hz, 2H), 7.34 (dd, J=1.8, 8.5 Hz, 1H), 7.28 (d, J=8.0 Hz, 1H), 7.27 (s, 1H), 7.15 (dd, J=2.5, 8.8 Hz, 1H), 7.11 (d, J=2.4 Hz, 1H), 4.21 (m, 4H), 3.93 (s, 3H), 3.82 (q, J=7.1 Hz, 1H), 3.38 (m, 2H), 3.14 (t, J=5.9 Hz, 2H), 2.42 (s, 3H), 1.57 (d, J=7.2 Hz, 3H). Mass spectrum (API-TIS) m/z 471 (M−NO2+H), 534 (M+18).

Example 49

2-(N-Methyl-2-(4-((nitrooxy)methyl)phenyl)acetylamino)ethyl(2S)-2-(6-methoxy(2-naphthyl))propanoate The title compound was prepared as a colorless oil (660 mg, 40% yield) from the product of Example 30a (1.10 g, 5.25 mmol) and the product of Example 45c (1 g, 3.5 mmol) following the procedure for Example 48. $^1$H NMR (300 MHz, CDCl$_3$) δ 7.72-7.65 (m, 4H), 7.57 (s, 2H), 7.25 (s, 1H), 7.16-7.06 (m, 3H), 5.32 (s, 2H), 4.22-4.09 (m, 2H), 4.01-3.98 (m, 1H), 3.90 (s, 3H), 3.75-3.69 (m, 2H), 3.54-3.45 (m, 2H), 2.68 (s, 3H), 1.49-1.45 (m, 3H); $^{13}$C NMR (75 MHz, CDCl$_3$) δ 174.0, 170.7, 157.7, 136.8, 135.2, 133.5, 131.0, 129.7, 129.4, 129.1, 128.3, 127.5, 126.2, 125.6, 119.0, 105.7, 74.4, 62.9, 55.3, 47.5, 43.5, 40.9, 36.4, 20.6; LRMS (APIMS) m/z 481 (M+H)$^+$.

Example 50

(2R)-2,3-Bis(nitrooxy)propyl 2-(1-((4-chlorophenyl)carbonyl)-5-methoxy-2-methylindol-3-yl)acetate To a solution of indomethacin (1.789 g, 5 mmol) and the product of Example 5d (0.91 g, 5 mmol) in anhydrous CH$_2$Cl$_2$ (25 mL) were added 1-ethyl-3-(3-dimethylaminopropyl) carbamide hydrochloride (EDAC) (0.96 g, 5 mmol) and N,N-dimethylaminopyridine (DMAP, 0.61 g, 5 mmol) at room temperature under nitrogen atmosphere. The reaction mixture was stirred at room temperature overnight. The solvent was evaporated and the residue was extracted with EtOAc, washed with water, brine, dried over sodium sulfate, filtered, and the organic extracts were evaporated. The product was purified by column chromatography on silica gel eluting with EtOAc:hexane (1:4) to give the title compound (1.6 g, 62% yield) as a colorless thick oil. $^1$H NMR (300 MHz, CDCl$_3$) δ 7.66 (d, J=8.2 Hz, 2H), 7.48 (d, J=8.2 Hz, 2H), 6.93 (s, 1H), 6.88 (d, J=9.0 Hz, 1H), 6.69 (d, J=8.9 Hz, 1H), 5.41 (s, 1H), 4.60 (dd, J=12.7 and 3.2 Hz, 1H), 4.48 (m, 2H), 4.25 (dd, J=12.3 and 5.9 Hz, 1H), 3.83 (s, 3H), 3.59 (s, 2H), 2.38 (s, 3H); $^{13}$C NMR (75 MHz, CDCl$_3$) δ 169.9, 168.2, 156.0, 139.3, 136.1, 133.6, 131.1, 130.7, 130.1, 129.1, 128.2, 114.9, 111.6, 111.3, 100.9, 75.9, 68.3, 60.8, 55.5, 29.8, 13.1; LRMS (APIMS) m/z 522 (MH$^+$).

Example 51

(2S)-2,3-Bis(nitrooxy)propyl 2-(1-((4-chlorophenyl)carbonyl)-5-methoxy-2-methylindol-3-yl)acetate 51a. (2S)-2,3-Bis(nitrooxy)propan-1-ol The title compound was prepared in four steps from ((4S)-2,2-dimethyl-1,3-dioxolan-4-yl)methan-1-ol following the procedures for Examples 5a, 5b, 5c, and 5d.

51b. (2S)-2,3-Bis(nitrooxy)propyl 2-(1-((4-chlorophenyl)carbonyl)-5-methoxy-2-methylindol-3-yl)acetate To a solution of indomethacin (1.789 g, 5 mmol) and the product of Example 51a (0.91 g, 5 mmol) in anhydrous CH$_2$Cl$_2$ (25 mL) were added 1-ethyl-3-(3-dimethylaminopropyl) carbamide hydrochloride (EDAC, 0.955 g, 5 mmol) and N,N-dimethylaminopyridine (DMAP, 0.61 g, 5 mmol) at room temperature under nitrogen atmosphere. The reaction mixture was stirred at room temperature overnight. The solvent was evaporated and the residue was extracted with EtOAc, washed with water, brine, dried over sodium sulfate, filtered, and the organic extracts were evaporated. The product was purified by column chromatography on silica gel eluting with EtOAc:hexane (1:4) to give the title compound (1.6 g, 62% yield) as a colorless thick oil. $^1$H NMR (300 MHz, CDCl$_3$) δ 7.99 (d, J=8.5 Hz, 2H), 7.46 (d, J=8.5 Hz, 2H), 6.91 (d, J=2.2 Hz, 1H), 6.85 (d, J=9.1 Hz, 1H), 6.63 (dd, J=9.0 and 2.5 Hz, 1H), 5.45 (m, 1H), 4.60 (dd, J=12.6 and 3.7 Hz, 1H), 4.45 (m, 2H), 4.25 (dd, J=12.6 and 5.6 Hz, 1H), 3.83 (s, 3H), 3.65 (s, 2H), 2.38 (s, 3H); $^{13}$C NMR (75 MHz, CDCl$_3$) δ 170.0, 168.2, 156.1, 139.4, 136.2, 133.6, 131.1, 130.7, 130.2, 129.1, 128.2, 115.0, 111.6, 111.4, 100.9, 75.9, 68.3, 60.9, 55.6, 29.9, 13.2; LRMS (APIMS) m/z 522 (MH$^+$).

Example 52

(2S)-2,3-Bis(nitrooxy)propyl 2-(2-((2,6-dichlorophenyl)amino)phenyl)acetate

To a solution of diclofenac (1.47 g, 5 mmol) and the product of Example 51a (0.91 g, 5 mmol) in anhydrous CH$_2$Cl$_2$ (25 mL) were added 1-ethyl-3-(3-dimethylaminopropyl) carbamide hydrochloride (EDAC, 0.955 g, 5 mmol) and N,N-dimethylaminopyridine (DMAP, 0.61 g, 5 mmol) at room temperature under nitrogen atmosphere. The reaction mixture was stirred at room temperature overnight. The solvent was evaporated and the residue was extracted with ethyl acetate, washed with water, brine, dried over sodium sulfate, filtered, and the organic extracts were evaporated. The product was purified by column chromatography on silica gel eluting with EtOAc:hexane (1:9) to give the title compound (1 g, 43% yield) as colorless thick oil. $^1$H NMR (300 MHz, CDCl$_3$) δ 7.35 (d, J=9.2 Hz, 2H), 7.2 (m, 2H), 7.0 (m, 2H), 6.6 (m, 2H), 5.5 (m, 1H), 4.75 (dd, J=12.2 and 3.9 Hz, 1H), 4.65-4.5 (m, 2H), 4.35 (dd, J=12.3 and 5.9 Hz, 1H), 3.87 (s, 2H); $^{13}$C NMR (75 MHz, CDCl$_3$) δ 171.5, 142.5, 137.5, 130.7, 129.3, 128.8, 128.3, 124.2, 123.3, 118.5, 76.0, 68.4, 61.1, 37.8; LRMS (APIMS) m/z 460 (MH$^+$).

Example 53

(2R)-2,3-bis(nitrooxy)propyl 2-(2-((2,6-dichlorophenyl)amino)phenyl)acetate

To a solution of diclofenac (1.47 g, 5 mmol) and the product of Example 5d (0.91 g, 5 mmol) in anhydrous CH$_2$Cl$_2$ (25 mL) were added 1-ethyl-3-(3-dimethylaminopropyl) carbamide hydrochloride (EDAC) (0.955 g, 5 mmol) and N,N-dimethylaminopyridine (DMAP, 0.61 g, 5 mmol) at room temperature under nitrogen atmosphere. The reaction mixture was stirred at room temperature overnight. The solvent was evaporated in vacuo and the residue was extracted with ethyl acetate, washed with water, brine, dried over sodium sulfate, filtered, and the organic extracts were evaporated. The product was purified by column chromatography on silica gel eluting with EtOAc:hexane (1:9) to give the title compound (0.5 g, 22% yield) as colorless thick oil. $^1$H NMR (300 MHz, CDCl$_3$) δ 7.4 (d, J=9.2 Hz, 2H), 7.25 (d, J=7.4 Hz, 2H), 7.18 (t, J=7.6 Hz, 1H), 7.03 (t, J=8.1 Hz, 1H), 6.6 (s, 1H), 6.61 (d, J=8.0 Hz, 1H), 5.5 (m, 1H), 4.72 (dd, J=12.9 and 3.4 Hz, 1H), 4.5 (m, 2H), 4.35 (dd, J=12.6 and 3.6 Hz, 1H), 3.89 (s, 2H); $^{13}$C NMR (75 MHz, CDCl$_3$) δ 171.5, 142.5, 137.5, 130.7, 129.3, 128.8, 128.3, 124.2, 123.5, 122.3, 118.5, 76.0, 68.4, 61.1, 37.8; LRMS (APIMS) m/z 460 (MH$^+$).

Example 54

(2S)-2-(6-methoxy(2-naphthyl))-1-(4-(nitrooxy)butylthio)propan-1-one 54a. (2S)-1-(4-Hydroxybutylthio)-2-(6-methoxy(2-naphthyl))propan-1-one To a solution of naproxen (5.03 g, 21.9 mmol), 4-mercapto-1-butanol (2.32 g, 21.9 mmol) and N,N-dimethylaminopyridine (DMAP) (0.534 g, 4.37 mmol) in dichloromethane (200 mL) at room temperature was added 1-(3-(dimethylamino)propyl)-3-ethylcarbodiimide hydrochloride (EDAC) (5.03 g, 26.2 mmol) as a solid, in portions. The reaction mixture was stirred for 3 hours at room temperature, then partitioned between dichloromethane and water, and the water layer was washed with more dichloromethane. The combined organic layer was washed with water and brine, then dried over magnesium sulfate. The solution was concentrated under vacuum, and the residue was purified via column chromatography, 50% ethyl acetate/hexane. The appropriate fractions were combined, and the solvent removed by rotary evaporation to give an oil, 2.647 g, which contained 19% 4-mercapto-1-butanol by weight (product weight 2.07 g, 6.5 mmol, 30% yield): $^1$H NMR (300 MHz, CDCl$_3$) δ 7.73 (d, J=2.7 Hz, 1H), 7.71 (d, J=2.3 Hz, 1H), 7.69 (d, J=1.0 Hz, 1H), 7.40 (dd, J=1.8, 8.5 Hz, 1H), 7.15 (dd, J=2.5, 8.8 Hz, 1H), 7.12 (d, J=2.3 Hz, 1H), 4.02 (q, J=7.1 Hz, 1H), 3.92 (s, 3H), 3.61-3.64 (m, 2H), 2.87 (m, 2H), 1.61 (d, J=7.1 Hz, 3H), 1.59 (m, 2H), 1.41 (m, 2H); mass spectrum (API-TIS) m/z 319 (M+H$^+$), 336 (M+18$^+$).

54b. (2S)-2-(6-methoxy(2-naphthyl))-1-(4-(nitrooxy)butylthio)propan-1-one

To acetic anhydride (3.45 mL, 37.2 mmol) at 0° C. was added fuming nitric acid (90%, 1.01 mL, 23.3 mmol) with stirring. After addition was complete, the mixture was stirred at room temperature for 25 min., then added dropwise to a solution of the product of Example 54a, (2.547 g, 15.5 mmol) in ethyl acetate (20 mL) at −10° C. The reaction mixture was stirred at −10° C. for 15 min., then quenched with 5 mL of saturated sodium bicarbonate. The mixture was stirred cold for 20 min., then warmed to room temperature for 1 h. The reaction mixture was partitioned between ethyl acetate and water, washed with sodium bicarbonate, water, and brine, and dried over sodium sulfate. The solvent was removed by rotary evaporation, and the residue was purified by column chromatography on silica, eluting with 25% ethyl acetate/hexane to give the nitrate as a pale yellow oil (1.17 g, 50% yield). The oil slowly solidified in the freezer. M.p. 30-35° C.; $^1$H NMR (300 MHz, CDCl$_3$) δ 7.73 (s, 1H), 7.70 (s, 1H), 7.68 (s, 1H), 7.38 (dd, J=1.7, 8.5 Hz, 1H), 7.15 (dd, J=2.5, 8.9 Hz, 1H), 7.11 (d, J=2.2 Hz, 1H), 4.39 (t, J=6.7 Hz, 2H), 4.01 (q, J=7.1 Hz, 1H), 3.91 (s, 3H), 2.86 (t, J=6.7 Hz, 2H), 1.65-1.74 (m, 4H), 1.61 (d, J=7.1 Hz, 3H); mass spectrum (API-TIS) m/z 318 (M−NO$_2^+$), 364 (M+H$^+$), 381 (M+18$^+$).

Example 55

(N-Methyl-N-(2-(nitrooxy)ethyl)carbamoyl)methyl 2-((4-chlorophenyl)carbonyl)-5-methoxy-2-methylindol-3-yl)acetate

55a. ((tert-Butyl)oxycarbonyl)methyl 2-(1-((4-chlorophenyl)carbonyl)-5-methoxy-2-methylindol-3-yl)acetate To a solution of indomethacin (6.388 g, 18 mmol) in anhydrous DMF (45 mL) were successively added NaHCO$_3$ (1.4 g, 16.7 mmol) and tert-butylbromoacetate (2.95 g, 15 mmol) at room temperature under nitrogen atmosphere. The reaction mixture was stirred at room temperature for 2 days. The reaction mixture was then poured over ice-cold water, stirred, and the white solid obtained was filtered off, washed with water and dried. The product was recrystallized from EtOAc:hexane (1:4) to give the title compound (7.06 g, 88% yield) as a white solid. Mp 96-97° C. $^1$H NMR (300 MHz, CDCl$_3$) δ 7.66 (d, J=8.5 Hz, 2H), 7.45 (d, J=8.5 Hz, 2H), 7.0 (d, J=2.4 Hz, 1H), 6.88 (d, J=9.0 Hz, 1H), 6.6 (dd, J=9.0 and 2.4 Hz, 1H), 4.52 (s, 2H), 3.83 (s, 3H), 3.77 (s, 2H), 2.37 (s, 3H), 1.44 (s, 9H); $^{13}$C NMR (75 MHz, CDCl$_3$) δ 170.1, 168.2, 166.6, 156.2, 139.2, 136.0, 133.8, 131.1 (2×C), 130.7, 130.5, 129.0 (2×C), 114.9, 112.1, 111.9, 101.1, 82.4, 61.5, 55.6, 29.7, 27.9, 13.4; LRMS (APIMS) m/z 472 (MH$^+$)

55b. 2-(2-(1-((4-Chlorophenyl)carbonyl)-5-methoxy-2-methylindol-3-yl)acetyloxy)acetic acid The product of Example 55a (6.12 g, 13 mmol) was dissolved in CH$_2$Cl$_2$ (50 mL) and TFA (15 mL) was added. The reaction mixture was stirred at room temperature for 2 days. The solvent and TFA were evaporated in vacuo and the residue obtained was dissolved in EtOAc (50 mL) and the solvent evaporated again to remove traces of trifluoroacetic acid. The residue obtained was recrystallized from EtOAc:hexane (1:4) to give the title compound (4.3 g, 80% yield) as a gray colored solid. Mp 137-138° C. $^1$H NMR (300 MHz, CDCl$_3$) δ 8.93 (br s, 1H), 7.65 (d, J=8.4 Hz, 2H), 7.45 (d, J=8.4 Hz, 2H), 6.96 (d, J=2.3 Hz, 1H), 6.87 (d, J=9.0 Hz, 1H), 6.6 (dd, J=9.0 and 2.4 Hz, 1H), 4.67 (s, 2H), 3.81 (s, 3H), 3.78 (s, 2H), 2.36 (s, 3H); $^{13}$C NMR (75 MHz, CDCl$_3$) δ 172.6, 170.3, 168.4, 155.9, 139.2, 136.1, 133.7, 131.1 (2×C), 130.7, 130.4, 129.1 (2×C), 114.9, 111.8, 111.7, 101.2, 60.5, 55.6, 29.6, 13.4; LRMS (APIMS) m/z 416 (MH$^+$).

55c. (N-Methyl-N-(2-(nitrooxy)ethyl)carbamoyl)methyl 2-(1-((4-chlorophenyl)carbonyl)-5-methoxy-2-methylindol-3-yl)acetate The product of Example 17c (457 mg, 2.5 mmol) was stirred in CH$_2$Cl$_2$ (10 mL) and Et$_3$N (0.25 mL) was added at room temperature and the reaction mixture was stirred for 10 minutes. Then the product of Example 55b (1.04 g, 2.5 mmol) in CH$_2$Cl$_2$ (10 mL) was added followed by 1-ethyl-3-(3-dimethylaminopropyl)carbamide hydrochloride (EDAC, 0.483 g, 2.5 mmol) and N,N-dimethylaminopyridine (DMAP, 0.305 g, 2.5 mmol). The resulting solution was stirred under nitrogen atmosphere at room temperature overnight. The reaction mixture was diluted with EtOAc, washed with water, aqueous NaHCO$_3$, water, 0.5 N HCl, brine, dried over sodium sulfate, filtered, and the organic extracts were evaporated. The product was purified by column chromatography on silica gel eluting with EtOAc:hexane (1:1) to give the title compound (1.1 g, 85% yield) as white foam. Mp 118-122° C. $^1$H NMR (300 MHz, CDCl$_3$) δ 7.65 (d, J=8.4 Hz, 2H), 7.45 (d, J=8.5 Hz, 2H), 7.0 (d, J=2.2 Hz, 1H), 6.87 (d, J=9.0 Hz, 1H), 6.65 (dd, J=9.0 and 2.3 Hz, 1H), 4.73 (s, 2H), 4.58 (t, J=5.1 Hz, 2H), 3.83 (s, 3H), 3.81 (s, 2H), 3.67 (t, J=5.1 Hz, 2H), 2.99 (s, 3H), 2.36 (s, 3H); $^{13}$C NMR (75 MHz, CDCl$_3$) δ 170.4, 168.2, 166.7, 156.0, 139.1, 136.0, 133.8, 131.1 (2×C), 130.6, 130.5, 129.0 (2×C), 114.8, 112.0, 111.8, 101.1, 70.9, 61.5, 55.6, 46.0, 35.6, 29.7, 13.3; LRMS (APIMS) m/z 534 (MH$^+$).

Example 56

(N-(2-(Nitrooxy)ethyl)carbamoyl)methyl 2-(1-((4-chlorophenyl)carbonyl)-5-methoxy-2-methylindol-3-yl)acetate The product of Example 22a., 2-(nitrooxy)ethylammonium nitrate (850 mgs, 5 mmol) and the product of Example 55b. (1.68 g, 4 mmol) were reacted with 1-ethyl-3-(3-dimethylaminopropyl)carbamide hydrochloride (EDAC, 4 mmol) and N,N-dimethylaminopyridine (DMAP, following the procedure for Example 55c. The product was purified by column chromatography on silica gel eluting with EtOAc: hexane (1:1) to give the title compound (1.22 g, 60% yield) as white solid. Mp 128-129° C. $^1$H NMR (300 MHz, CDCl$_3$) δ 7.65 (d, J=8.4 Hz, 2H), 7.45 (d, J=8.4 Hz, 2H), 6.96 (d, J=2.2 Hz, 1H), 6.87 (d, J=9.0 Hz, 1H), 6.7 (dd, J=9.0 and 2.3 Hz, 1H), 6.1 (t, J=5.1 Hz, 2H), 4.56 (s, 2H), 4.32 (t, J=5.1 Hz, 2H), 3.81 (s, 3H), 3.77 (s, 2H), 3.37 (q, J=5.2 Hz, 2H), 2.38 (s, 3H); $^{13}$C NMR (75 MHz, CDCl$_3$) δ 168.9, 168.2, 167.3, 156.1, 139.5, 136.3, 133.5, 131.1 (2×C), 130.8, 130.1, 129.1 (2×C), 115.3, 111.4, 101.0, 70.9, 62.8, 55.7, 36.4, 30.1, 13.3; LRMS (APIMS) m/z 504 (MH$^+$) and 521 (MNH$_4^+$).

Example 57

(N-(2-(Nitrooxy)ethyl)carbamoyl)methyl 2-(2-((2,6-dichlorophenyl)amino)phenyl)acetate 57a. Oxycarbonylmethyl 2-(2-((2,6-dichlorophenyl)amino)phenyl)acetate To a solution of diclofenac (7.7 g, 26 mmol) in anhydrous DMF (60 mL) were successively added NaHCO$_3$ (2.8 g, 33.4 mmol) and tert-butylbromoacetate (5.07 g, 26 mmol) at room temperature under nitrogen atmosphere, and the reaction mixture was stirred at room temperature overnight. The solvent was evaporated under reduced pressure and the residue obtained was triturated with a mixture of 20% ethylacetate in hexane to give the title compound (10.1 g) as a white solid in quantitative yield. Mp 83-84° C. $^1$H NMR (300 MHz, CDCl$_3$) δ 7.33 (d, J=8.5 Hz, 2H), 7.25 (m, 1H), 7.12 (t, J=5.5 Hz, 1H), 6.96 (m, 2H), 6.78 (br s, 1H), 6.54 (d, J=8.4 Hz, 1H), 4.56 (s, 2H), 3.92 (s, 2H), 1.35 (s, 9H); $^{13}$C NMR (75 MHz, CDCl$_3$) δ 171.3, 166.4, 142.7, 137.8, 130.9, 129.5, 128.8, 128.0, 124.0, 123.9, 122.0, 118.3, 82.6, 61.7, 38.1, 27.8.

57b. Oxycarbonylmethyl 2-(2-((2,6-dichlorophenyl)amino)phenyl)acetate

The product of Example 57a (0.3 g, 0.73 mmol) was dissolved in dichloromethane (4 mL) and trifluoroacetic acid (1 mL) was added. The reaction mixture was stirred at room temperature for 7 h. The solvent and trifluoroacetic acid were evaporated in vacuo and the residue obtained was purified by flash column chromatography over silica gel using 40% ethylacetate in hexane to give the title compound (0.15 g, 57% yield) as a white solid. Mp 107-111° C. $^1$H NMR (300 MHz, CDCl$_3$) δ 7.33 (d, J=8.4 Hz, 2H), 7.24 (d, J=8.4 Hz, 1H), 7.13 (t, J=5.5 Hz, 1H), 6.95 (m, 2H), 6.6 (br s, 1H), 6.53 (d, J=8.5 Hz, 1H), 4.71 (s, 2H), 3.80 (s, 2H); LRMS (APIMS) m/z 354 (MH$^+$).

57c. (N-(2-(Nitrooxy)ethyl)carbamoyl)methyl 2-(2-((2,6-dichlorophenyl)amino) phenyl)acetate The product of Example 22a., 2-(nitrooxy)ethylammonium nitrate (132 mgs, 0.84 mmol) and the product of example 57b. (150 mg, 0.42 mmol) were reacted using EDAC (80 mg, 0.42 mmol) and DMAP (51 mg, 0.42 mmoL) following the procedure as described in example 55c. The product was purified by column chromatography over silica gel using 20% ethyl acetate in hexane to give the title compound (23 mg, 13% yield) as a white solid, mp 81-83° C. $^1$H NMR (300 MHz, CDCl$_3$) δ 7.35 (d, J=8.5 Hz, 2H), 7.28 (dd, J=8.4 and 2.2 Hz, 1H), 7.18 (dt, J=5.5 and 2.2 Hz, 1H), 7.1-7.0 (m, 2H), 6.54 (d, J=8.4 Hz, 1H), 6.41 (br s, 1H), 6.08 (m, 1H), 4.60 (s, 2H), 4.41 (t, J=5.5 Hz, 2H), 3.91 (s, 2H), 3.48 (q, J=5.5 Hz, 2H); $^{13}$C NMR (75 MHz, CDCl$_3$) δ 170.2, 167.2, 142.4, 137.2, 130.8, 129.7, 128.9, 128.5, 124.5, 124.6, 123.0, 122.2, 118.2, 71.1, 63.0, 38.1, 36.4; LRMS (APIMS) m/z 442 (MH Example 58

Comparative In Vivo Antiinflammatory and Gastric Lesion Activities

The rat paw edema test was used to measure the antiinflammatory activity. The rat paw edema test was performed according to the method of Winter et al, *Proc. Soc. Exp. Biol. Med.* 111: 544-547, 1962. Male Sprague-Dawley rats (250-275 g) were fasted overnight and dosed by oral gavage with vehicle or suspensions of compound one hour prior to the subplantar injection of 50 μl of 1% suspension of carrageenan. Three hours later, the paw volume was measured and compared with the initial volume measured immediately after carrageenan injection.

The rat gastric lesion test, described by Kitagawa et al, *J. Pharmacol. Exp. Ther.*, 253:1133-1137 (1990), and Al-Ghamdi et al, *J. Int. Med. Res.*, 19:2242 (1991), was used to evaluate the activity of compounds to produce gastric lesion. Male Sprague Dawley rats (Charles River Laboratories, Wilmington, Mass.) weighing 230-250 g were used for the experiments. The rats were housed with laboratory chow and water ad libitum prior to the study. The rats were fasted for 24 hours with free access to water and then dosed by oral gavage with vehicle or with test compounds given at a volume of 0.5 mL/100 g. Food was withheld after the initial dosing. Rats were euthanized by $CO_2$ three hours after dosing. The stomachs were dissected along the greater curvature, washed with a directed stream of 0.9% saline and pinned open on a sylgard based petri dish for examination of the hemorrhagic lesion. Gastric lesion score was expressed in mm and calculated by summing the length of each lesion.

Table 1 shows the relative activities of compounds in the analgesic, antiinflammatory and gastric lesion tests, and are expressed as the ratio of activity relative to the parent NSAID. The results show that the nitrosated NSAIDs have either comparable antiinflammatory activities compared to their parent NSAID molecule. Table 1 also shows that the nitrosated NSAIDs of the invention have significantly and unexpectedly decreased gastric lesion activities.

TABLE 1

| Compound | Relative Activity Antiinflammation | Gastric Lesion |
|---|---|---|
| Vehicle | 1 | <0.01 |
| Naproxen | 0.55 | 1 |
| Example 1 | 0.46 | 0.32 |
| Example 2 | 0.49 | 0.11 |
| Example 4 | 0.92 | 0.04 |
| Example 5 | 0.45 | 0.21 |
| Example 6 | 0.45 | 0.09 |
| Example 7 | 0.85 | Not determined |
| Example 9 | 0.69 | 0.02 |
| Example 11 | 0.82 | Not determined |
| Example 12 | 0.47 | 0.18 |
| Example 13 | 0.51 | 0.55 |
| Example 14 | 0.78 | 0.15 |
| Example 18 | 0.60 | 0.25 |
| Example 19 | 0.60 | 0.30 |
| Example 20 | 0.63 | 0.03 |
| Example 21 | 0.48 | 0.19 |
| Example 23 | 0.87 | Not determined |

TABLE 1-continued

| Compound | Relative Activity Antiinflammation | Gastric Lesion |
|---|---|---|
| Example 26 | 0.75 | 0.07 |
| Example 27c | 0.57 | 0.20 |
| Example 27d | 0.72 | Not determined |
| Example 28 | 0.57 | Not determined |
| Example 31 | 0.61 | 0.06 |
| Example 32 | 0.58 | 0.06 |
| Example 33 | 0.60 | 0.07 |
| Example 34 | 0.60 | 0.02 |
| Example 35 | 0.06 | Not determined |
| Example 36 | 0.65 | 0.57 |
| Example 37 | 0.56 | 0.72 |
| Example 39 | 0.70 | 0.04 |
| Example 41 | 0.86 | Not determined |

The disclosure of each patent, patent application and publication cited or described in the specification is hereby incorporated by reference herein in its entirety.

Although the invention has been set forth in detail, one skilled in the art will appreciate that numerous changes and modifications can be made to the invention, and that such changes and modifications may be made without departing from the spirit and scope of the present invention.

What is claimed is:

1. A method for treating an inflammatory disease in a patient in need thereof comprising administering to the patient a therapeutically effective amount of a composition comprising a pharmaceutically acceptable carrier and at least one compound of Formula (I), or a pharmaceutically acceptable salt thereof;

wherein the compound of Formula (I) is:

$$R_n-\underset{H}{\overset{R_m}{\underset{|}{C}}}-\overset{O}{\underset{\|}{C}}-X \quad (I)$$

wherein:

$R_m$ is a hydrogen or a lower alkyl group;

$R_n$ is:

(i) [structure: 6-methoxynaphthalen-2-yl];

(ii) [structure: 2-((2,6-dichlorophenyl)amino)phenyl];

(iii) [structure: 5-methoxy-2-methyl-1-(4-chlorobenzoyl)-1H-indol-3-yl];

X is —Y—$(CR_4R_4')_o$—$(W)_q$—$(CR_4R_4')_o$—$(CH_2)$—$ONO_2$;

$R_4$ and $R_4'$ at each occurrence are independently a hydrogen, lower alkyl group, —OH, —$CH_2OH$, —$ONO_2$, —$NO_2$ or —$CH_2ONO_2$; or $R_4$ and $R_4'$ taken together with the carbon atom to which they are attached are a cycloalkyl group or a heterocyclic ring; and with the proviso that at least one $R_4$ or $R_4'$ must be —OH, —$ONO_2$, —$NO_2$ or —$CH_2ONO_2$;

W is a covalent bond;

q is an integer of 1;

o at one occurrence is an integer of 1 or 2; and o at the other occurrence is an integer from 0 to 2; and Y is oxygen or sulfur (—S—).

2. The method of claim 1, wherein the compound of Formula (I) is:

$$R_n-\underset{H}{\overset{R_m}{\underset{|}{C}}}-\overset{O}{\underset{\|}{C}}-X \quad (I)$$

wherein:

$R_m$ is a hydrogen or a lower alkyl group;

$R_n$ is:

(i) [structure: 6-methoxynaphthalen-2-yl];

(ii) [structure: 2-((2,6-dichlorophenyl)amino)phenyl]; or

-continued

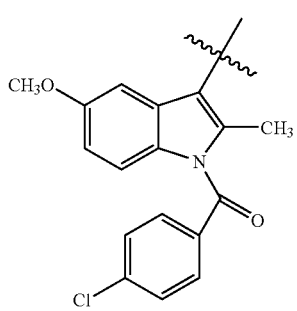

(iii)

X is:

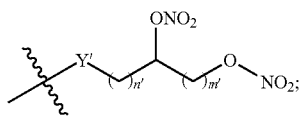

Y' is oxygen or sulfur; and n' and m' are each independently an integer from 0 to 6.

3. The method of claim 1, wherein the compound of Formula (I) is a nitrosated diclofenac, a nitrosated indomethacin or a nitrosated naproxen.

4. The method of claim 1, wherein the inflammatory disease is arthritis tendinitis, bursitis, or an inflammatory process in a disease.

5. A method for treating an inflammatory disease in a patient in need thereof comprising administering to the patient a therapeutically effective amount of a composition comprising a pharmaceutically acceptable carrier and at least one compound selected from the group consisting of:

(2R)-2,3-bis(nitrooxy)propyl(2S)-2(6-methoxy(2-naphthyl)propanoate or a pharmaceutically acceptable salt thereof;

2,2-bis(nitrooxy)propyl (2S)-2-(6-methoxy(2-naphthyl)) propanoate or a pharmaceutically acceptable salt thereof;

2-methyl-2-nitro-3-(nitrooxy)propyl (2S)-2-(6-methoxy (2-naphthyl))propanoate or a pharmaceutically acceptable salt thereof;

2-nitro-3-(nitrooxy)-2-((nitrooxy)methyl)propyl (2S)-2-(6-methoxy(2-naphthyl)) propanoate or a pharmaceutically acceptable salt thereof;

(2S)-2,3-bis(nitrooxy)propyl(2S)-2-(6-methoxy-5-nitro (2-naphthyl)) propanoate or a pharmaceutically acceptable salt thereof;

(2S)-2-hydroxy-3-(nitrooxy)propyl (2S)-2-(6-methoxy(2-naphthyl))propanoate or a pharmaceutically acceptable salt thereof;

(2R)-2-hydroxy-3-(nitrooxy)propyl (2S)-2-(6-methoxy (2-naphthyl)) propanoate or a pharmaceutically acceptable salt thereof;

(2R)-2,3-bis(nitrooxy)propyl 2-(1-((4-chlorophenyl)carbonyl)-5-methoxy-2-methylindol-3-yl)acetate or a pharmaceutically acceptable salt thereof;

(2S)-2,3-bis(nitrooxy)propyl 2-(1-((4-chlorophenyl)carbonyl)-5-methoxy-2-methylindol-3-yl)acetate or a pharmaceutically acceptable salt thereof;

(2S)-2,3-bis(nitrooxy)propyl 2-(2-((2,6-dichlorophenyl) amino)phenyl)acetate or a pharmaceutically acceptable salt thereof; and (2R)-2,3-bis(nitrooxy)propyl 2-(2-((2,6-dichlorophenyl) amino)phenyl)acetate or a pharmaceutically acceptable salt thereof.

6. The method of claim 5, wherein the inflammatory disease is arthritis tendinitis, bursitis or an inflammatory process in a disease.

* * * * *